US010034928B2

(12) United States Patent
Møller et al.

(10) Patent No.: US 10,034,928 B2
(45) Date of Patent: Jul. 31, 2018

(54) **PROTEINS AND NUCLEIC ACIDS USEFUL IN VACCINES TARGETING *STAPHYLOCOCCUS AUREUS***

(71) Applicant: Evaxion Biotech ApS, Copenhagen N (DK)

(72) Inventors: Niels Iversen Møller, Gilleleje (DK); Andreas Holm Mattsson, Copenhagen Ø (DK)

(73) Assignee: Evaxion Biotech ApS, Copenhagen K (DK)

( * ) Notice: Subject to any disclaimer, the term of this patent is extended or adjusted under 35 U.S.C. 154(b) by 0 days.

(21) Appl. No.: 15/387,814

(22) Filed: Dec. 22, 2016

(65) Prior Publication Data

US 2017/0100470 A1    Apr. 13, 2017

Related U.S. Application Data

(60) Continuation of application No. 14/802,602, filed on Jul. 17, 2015, now Pat. No. 9,534,022, which is a division of application No. 14/110,475, filed as application No. PCT/EP2012/056069 on Apr. 3, 2012, now Pat. No. 9,085,631.

(60) Provisional application No. 61/473,376, filed on Apr. 8, 2011.

(30) Foreign Application Priority Data

Apr. 8, 2011   (DK) .................. 2011 70167

(51) Int. Cl.
| | |
|---|---|
| *A61K 39/085* | (2006.01) |
| *C07K 14/31* | (2006.01) |
| *C12Q 1/68* | (2018.01) |
| *A61K 39/00* | (2006.01) |
| *C12Q 1/689* | (2018.01) |

(52) U.S. Cl.
CPC ............ *A61K 39/085* (2013.01); *C07K 14/31* (2013.01); *A61K 2039/545* (2013.01); *A61K 2039/55505* (2013.01); *C07K 2317/34* (2013.01); *C12Q 1/689* (2013.01)

(58) Field of Classification Search
CPC .. A61K 38/00; A61K 2300/00; A61K 31/716; A61K 31/155; A61K 31/44; A61K 38/16; A61K 38/4826; A61K 6/087; A61K 2039/5156; A61K 2039/523; A61K 2039/5256; A61K 38/1709; A61K 38/486; A61K 38/4873; A61K 38/482
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,684,611 A | 8/1987 | Schilperoort et al. | |
| 4,800,159 A | 1/1989 | Mullis et al. | |
| 4,879,236 A | 11/1989 | Smith et al. | |
| 4,952,500 A | 8/1990 | Finnerty et al. | |
| 5,302,523 A | 4/1994 | Coffee et al. | |
| 5,322,783 A | 6/1994 | Tomes et al. | |
| 5,384,253 A | 1/1995 | Krzyzek et al. | |
| 5,464,765 A | 11/1995 | Coffee et al. | |
| 5,538,877 A | 7/1996 | Lundquist et al. | |
| 5,538,880 A | 7/1996 | Lundquist et al. | |
| 5,550,318 A | 8/1996 | Adams et al. | |
| 5,563,055 A | 10/1996 | Townsend et al. | |
| 5,580,859 A | 12/1996 | Felgner et al. | |
| 5,589,466 A | 12/1996 | Felgner et al. | |
| 5,591,616 A | 1/1997 | Hiei et al. | |
| 5,610,042 A | 3/1997 | Chang et al. | |
| 5,656,610 A | 8/1997 | Shuler et al. | |
| 5,702,932 A | 12/1997 | Hoy et al. | |
| 5,736,524 A | 4/1998 | Content et al. | |
| 5,780,448 A | 7/1998 | Davis | |
| 5,789,215 A | 8/1998 | Berns et al. | |
| 5,843,650 A | 12/1998 | Segev | |
| 5,846,709 A | 12/1998 | Segev | |
| 5,846,783 A | 12/1998 | Wu et al. | |
| 5,849,497 A | 12/1998 | Steinman | |
| 5,849,546 A | 12/1998 | Sousa et al. | |
| 5,849,547 A | 12/1998 | Cleuziat et al. | |
| 5,858,652 A | 1/1999 | Laffler et al. | |
| 5,866,366 A | 2/1999 | Kallender | |
| 5,871,986 A | 2/1999 | Boyce | |
| 5,916,776 A | 6/1999 | Kumar | |
| 5,922,574 A | 7/1999 | Minter | |
| 5,925,565 A | 7/1999 | Berlioz et al. | |
| 5,928,905 A | 7/1999 | Stemmer et al. | |
| 5,928,906 A | 7/1999 | Koster et al. | |

(Continued)

FOREIGN PATENT DOCUMENTS

| | | |
|---|---|---|
| FR | 2944807 | 10/2010 |
| GB | 2202328 | 9/1988 |

(Continued)

OTHER PUBLICATIONS

UniProt; Accession No. Q6GGT1 ; Jan. 2007.*
Li, W. et al, Structural insights into the pro-apoptotic function of mitochondrial serine protease HtrA2/Omi:, Nat. Struct. Biol., vol. 9(6), pp. 436-441, (Jun. 2002).
Holden, M. et al, *Staphylococcus aureus* subsp., *aureus* strain MRSA252, complete genome, XP002682643, (Jun. 2004, updated May 2009).
Feldgarden, M. et al, "*Staphylococcus aureus* subsp. *aureus* 68-397; Full=predicted protein", XP002682642, EBI accession C8A9W6, (Oct. 13, 2009).

(Continued)

*Primary Examiner* — Padmavathi Baskar
(74) *Attorney, Agent, or Firm* — McHale & Slavin, P.A.

(57) ABSTRACT

Disclosed are novel immunogenic proteins derived from *Staphylococcus aureus*, as well as methods for their use in conferring protective immunity against *S. aureus* infections. Also disclosed are nucleic acids encoding the proteins and methods of use of these nucleic acids.

9 Claims, No Drawings

(56) References Cited

U.S. PATENT DOCUMENTS

| | | | |
|---|---|---|---|
| 5,932,451 A | 8/1999 | Wang et al. | |
| 5,935,819 A | 8/1999 | Eichner et al. | |
| 5,935,825 A | 8/1999 | Nishimura et al. | |
| 5,939,291 A | 8/1999 | Loewy et al. | |
| 5,942,391 A | 8/1999 | Zhang et al. | |
| 5,945,100 A | 8/1999 | Fick | |
| 5,981,274 A | 11/1999 | Tyrrell et al. | |
| 5,994,624 A | 11/1999 | Trolinder et al. | |
| 7,608,276 B2 | 10/2009 | Masignani et al. | |
| 8,703,148 B2 * | 4/2014 | Biemans | A61K 39/085 424/184.1 |
| 9,085,631 B2 | 7/2015 | Moller et al. | |
| 9,534,022 B2 | 1/2017 | Moller et al. | |
| 2014/0072556 A1 | 3/2014 | Moller et al. | |

FOREIGN PATENT DOCUMENTS

| | | |
|---|---|---|
| WO | WO9014837 | 12/1990 |
| WO | WO9409699 | 5/1994 |
| WO | WO9506128 | 3/1995 |
| WO | WO9820734 | 5/1998 |
| WO | WO2002094868 | 11/2002 |
| WO | WO2005014857 | 2/2005 |
| WO | WO2010119343 A3 | 10/2010 |
| WO | WO2010119343 A8 | 10/2010 |
| WO | WO2012136653 | 10/2012 |

OTHER PUBLICATIONS

Feldgarden, M. et al, "*Staphylococcus aureus* subsp. strain *aureus* MRSA252, complete genome", XP002682643, EM-PRO accession BX571856.1, 766363-766752, (Jun. 23, 2004).

\* cited by examiner

SEQUENCE LISTING

<160> NUMBER OF SEQ ID NOS: 57

<210> SEQ ID NO 1
<211> LENGTH: 154
<212> TYPE: PRT
<213> ORGANISM: Staphylococcus aureus

<400> SEQUENCE: 1

Met Lys Arg Leu Leu Gly Leu Leu Val Ser Thr Leu Val Leu Ser
1               5                   10                  15

Ala Cys Gly Asn Asp Glu Asn Gln Glu Glu Ser Lys Lys Glu Val Lys
                20                  25                  30

Ser Lys Glu Lys Lys Ile Glu Lys Lys Glu Asn Lys Ser Lys Lys
            35                  40                  45

Asp Lys Glu Lys Glu Val Ala Thr Gln Gln Pro Asp Asn Gln Thr
        50                  55                  60

Val Glu Gln Pro Gln Ser Gln Glu Gln Ser Val Gln Pro Gln Gln
65                  70                  75                  80

Gln Ile Pro Gln Asn Ser Val Pro Gln Asn Val Gln Val Gln Gln
                85                  90                  95

Asn Lys Lys Gln Lys Val Asp Leu Asn Asn Met Pro Pro Thr Asp Phe

```
                 100                 105                 110
Ser Thr Glu Gly Met Ser Glu Gln Ala Gln Lys Gln Ile Glu Glu Leu
            115                 120                 125

Ser Met Gln Lys Asp Tyr His Gly Leu Ser Gln Arg Glu Tyr Asn Asp
            130                 135                 140

Arg Val Ser Glu Ile Ile Asn Asn Asp Asn
145                 150
```

<210> SEQ ID NO 2
<211> LENGTH: 184
<212> TYPE: PRT
<213> ORGANISM: Staphylococcus aureus

<400> SEQUENCE: 2

```
Met Leu Lys Gly Cys Gly Gly Cys Leu Ile Ser Phe Ile Ile Leu Ile
1               5                   10                  15

Ile Leu Leu Ser Ala Cys Ser Met Met Phe Ser Asn Asn Asp Asn Ser
            20                  25                  30

Thr Ser Asn Gln Ser Ser Lys Thr Gln Leu Thr Gln Lys Asp Glu Asp
        35                  40                  45

Lys Ser Glu Asn Met Pro Glu Glu Lys Ser Ser Glu Thr Asp Lys
50                  55                  60

Asp Leu Gln Ser Thr Glu Glu Val Pro Ala Asn Glu Asn Thr Glu Asn
65                  70                  75                  80

Asn Gln His Glu Ile Asp Glu Ile Thr Thr Thr Asp Gln Ser Asp Asp
                85                  90                  95

Glu Ile Asn Thr Pro Asn Val Ala Glu Glu Ser Gln Asp Asp Leu
            100                 105                 110

Lys Asp Asp Leu Lys Glu Lys Gln Gln Pro Ser Asp His His Gln Ser
            115                 120                 125

Thr Gln Pro Lys Thr Ser Pro Ser Thr Glu Thr Asn Lys Gln Gln Ser
        130                 135                 140

Phe Ala Asn Cys Lys Gln Leu Arg Gln Val Tyr Pro Asn Gly Val Thr
145                 150                 155                 160

Ala Asp His Pro Ala Tyr Arg Pro His Leu Asp Arg Asp Lys Asp Lys
                165                 170                 175

Arg Ala Cys Glu Pro Asp Lys Tyr
            180
```

<210> SEQ ID NO 3
<211> LENGTH: 129
<212> TYPE: PRT
<213> ORGANISM: Staphylococcus aureus

<400> SEQUENCE: 3

```
Met Lys Lys Leu Ile Ile Ser Ile Met Ala Ile Met Leu Phe Leu Thr
1               5                   10                  15

Gly Cys Gly Lys Ser Gln Glu Lys Ala Thr Leu Glu Lys Asp Ile Asp
            20                  25                  30

Asn Leu Gln Lys Glu Asn Lys Glu Leu Lys Asp Lys Glu Lys Leu
        35                  40                  45

Gln Gln Glu Lys Glu Lys Ala Asp Lys Gln Lys Asp Leu Glu Lys
    50                  55                  60

Glu Val Lys Asp Leu Lys Pro Ser Lys Glu Asp Asn Lys Asp Lys
65                  70                  75                  80

Lys Asp Glu Asp Lys Asn Lys Asp Lys Asp Lys Glu Ala Ser Gln Asp
```

```
                        85                  90                  95
Lys Gln Ser Lys Asp Gln Thr Lys Ser Ser Asp Lys Asp Asn His Lys
                100                 105                 110

Lys Pro Thr Ser Thr Asp Lys Asp Gln Lys Ala Asn Asp Lys His Gln
            115                 120                 125

Ser

<210> SEQ ID NO 4
<211> LENGTH: 993
<212> TYPE: PRT
<213> ORGANISM: Staphylococcus aureus

<400> SEQUENCE: 4

Met Lys Asn Ala Phe Lys Leu Phe Lys Met Asp Leu Lys Lys Val Ala
1               5                   10                  15

Lys Thr Pro Ala Val Trp Ile Ile Leu Ala Gly Leu Ala Ile Leu Pro
            20                  25                  30

Ser Phe Tyr Ala Trp Phe Asn Leu Trp Ala Met Trp Asp Pro Tyr Gly
        35                  40                  45

Asn Thr Gly His Ile Lys Val Ala Val Asn Glu Asp Lys Gly Asp
    50                  55                  60

Thr Ile Arg Gly Lys Lys Val Asn Val Gly Asn Thr Met Val Asn Thr
65                  70                  75                  80

Leu Lys Lys Asn Lys Ser Phe Asp Trp Gln Phe Val Ser Arg Glu Lys
                85                  90                  95

Ala Asp His Glu Ile Lys Met Gly Lys Tyr Phe Ala Gly Ile Tyr Ile
                100                 105                 110

Pro Ser Lys Phe Thr His Glu Ile Thr Gly Thr Leu Arg Lys Gln Pro
            115                 120                 125

Gln Lys Ala Asp Val Glu Phe Lys Val Asn Gln Lys Ile Asn Ala Val
130                 135                 140

Ala Ser Lys Leu Thr Asp Thr Gly Ser Ser Val Val Val Glu Lys Ala
145                 150                 155                 160

Asn Glu Gln Phe Asn Lys Thr Val Thr Arg Ala Leu Leu Glu Glu Ala
                165                 170                 175

Asn Lys Ala Gly Leu Thr Ile Glu Glu Asn Val Pro Thr Ile Asn Lys
                180                 185                 190

Ile Lys Asn Ala Val Tyr Ser Ala Asp Lys Ala Leu Pro Lys Ile Asn
            195                 200                 205

Asp Phe Ala Asn Lys Ile Val Tyr Leu Asn Asn His Gln Ala Asp Leu
    210                 215                 220

Asp Lys Tyr Ala Asn Asp Phe Arg Lys Leu Gly Asn Tyr Lys Gly Asp
225                 230                 235                 240

Ile Leu Asp Ala Gln Lys Lys Leu Asn Glu Val Asn Gly Ala Ile Pro
                245                 250                 255

Gln Leu Asn Glu Lys Ala Lys Leu Ile Leu Ala Leu Asn Asn Tyr Met
                260                 265                 270

Pro Lys Ile Glu Lys Ala Leu Asn Phe Ala Ala Asp Asp Val Pro Ala
            275                 280                 285

Gln Phe Pro Lys Ile Asn Gln Gly Leu Asn Ile Ala Ser Gln Gly Ile
    290                 295                 300

Asp Gln Ala Asn Gly Gln Leu Asn Asp Ala Lys Gly Phe Val Thr Gln
305                 310                 315                 320

Val Arg Ser Arg Val Gly Asp Tyr Gln Glu Ala Ile Arg Arg Ala Gln
```

```
                    325                 330                 335
Asp Leu Asn Arg Arg Asn Gln Gln Gln Ile Pro Gln Asn Ser Ala Ala
                340                 345                 350

Asn Asn Glu Thr Ser Asn Ser Ala Pro Ala Ala Gly Asn Gly Val Thr
            355                 360                 365

Ser Thr Pro Pro Ser Ala Pro Asn Gly Asn Thr Thr Pro Asn Asn Asn
    370                 375                 380

Val Thr Gln Asn Thr Ala Pro Asn Ser Asn Asn Ala Pro Val Ser Thr
385                 390                 395                 400

Thr Pro Gln Ser Thr Ser Gly Lys Lys Asp Gly Gln Ser Phe Ala Asp
                405                 410                 415

Ile Thr Thr Thr Gln Val Ser Thr Ala Asn Glu Asn Thr Gln Asn Ile
            420                 425                 430

Thr Asp Lys Asp Val Lys Ser Met Glu Ala Ala Leu Thr Gly Ser Leu
    435                 440                 445

Leu Ser Leu Ser Asn Asn Leu Asp Thr Gln Ala Lys Ala Ala Gln Lys
450                 455                 460

Asp Ser Gln Ala Leu Arg Asn Ile Ser Tyr Gly Ile Leu Ala Ser Asp
465                 470                 475                 480

Lys Pro Ser Asp Phe Arg Glu Ser Leu Asp Asn Val Lys Ser Gly Leu
                485                 490                 495

Glu Tyr Thr Thr Gln Tyr Asn Gln Gln Phe Ile Asp Thr Leu Lys Glu
            500                 505                 510

Ile Glu Lys Asn Glu Asn Val Asp Leu Ser Lys Glu Ile Asp Lys Val
    515                 520                 525

Lys Thr Ala Asn Asn Arg Ile Asn Glu Ser Leu Arg Leu Val Asn Gln
530                 535                 540

Leu Ser Asn Ala Leu Lys Asn Gly Ser Ser Gly Thr Ala Glu Ala Thr
545                 550                 555                 560

Lys Leu Leu Asp Gln Leu Ser Lys Leu Asp Ser Ser Leu Ser Ser Phe
                565                 570                 575

Arg Asp Tyr Val Lys Lys Asp Leu Asn Ser Ser Leu Val Ser Ile Ser
            580                 585                 590

Gln Arg Ile Met Asp Glu Leu Asn Lys Gly Gln Thr Ala Leu Ser Asn
    595                 600                 605

Val Gln Ser Lys Leu Asn Thr Ile Asp Gln Val Ile Asn Ser Gly Gln
610                 615                 620

Ser Ile Leu Lys Asn Gly Lys Thr Arg Ile Asp Arg Leu Gln Thr Val
625                 630                 635                 640

Leu Pro Ser Ile Glu Gln Gln Tyr Ile Ser Ala Ile Lys Asn Ala Gln
                645                 650                 655

Ala Asn Phe Pro Lys Val Lys Ser Asp Val Ala Lys Ala Ala Asn Phe
            660                 665                 670

Val Arg Asn Asp Leu Pro Gln Leu Glu Gln Arg Leu Thr Asn Ala Thr
    675                 680                 685

Ala Ser Val Asn Lys Asn Leu Pro Thr Leu Leu Asn Gly Tyr Asp Gln
690                 695                 700

Ala Val Gly Leu Leu Asn Lys Asn Gln Pro Gln Ala Lys Lys Ala Leu
705                 710                 715                 720

Ser Asp Leu Ala Asp Phe Ala Gln Asn Lys Leu Pro Asp Val Glu Lys
                725                 730                 735

Asp Leu Lys Lys Ala Asn Lys Ile Phe Lys Lys Leu Asp Lys Asp Asp
            740                 745                 750
```

```
Ala Val Asp Lys Leu Ile Asp Thr Leu Lys Asn Asp Leu Lys Lys Gln
            755                 760                 765

Ala Gly Ile Ile Ala Asn Pro Ile Asn Lys Lys Thr Val Asp Val Phe
770                 775                 780

Pro Val Lys Asp Tyr Gly Ser Gly Met Thr Pro Phe Tyr Thr Ala Leu
785                 790                 795                 800

Ser Val Trp Val Gly Ala Leu Leu Met Val Ser Leu Leu Thr Val Asp
            805                 810                 815

Asn Lys His Lys Ser Leu Glu Pro Val Leu Thr Thr Arg Gln Val Phe
            820                 825                 830

Leu Gly Lys Ala Gly Phe Phe Ile Met Leu Gly Met Leu Gln Ala Leu
            835                 840                 845

Ile Val Ser Val Gly Asp Leu Leu Ile Leu Lys Ala Gly Val Glu Ser
            850                 855                 860

Pro Val Leu Phe Val Leu Ile Thr Ile Phe Cys Ser Ile Ile Phe Asn
865                 870                 875                 880

Ser Ile Val Tyr Thr Cys Val Ser Leu Leu Gly Asn Pro Gly Lys Ala
                885                 890                 895

Ile Ala Ile Val Leu Leu Val Leu Gln Ile Ala Gly Gly Gly Gly Thr
            900                 905                 910

Phe Pro Ile Gln Thr Thr Pro Gln Phe Phe Gln Asn Ile Ser Pro Tyr
            915                 920                 925

Leu Pro Phe Thr Tyr Ala Ile Asp Ser Leu Arg Glu Thr Val Gly Gly
            930                 935                 940

Ile Val Pro Glu Ile Leu Ile Thr Lys Leu Ile Ile Leu Thr Leu Phe
945                 950                 955                 960

Gly Ile Gly Phe Phe Val Val Gly Leu Ile Leu Lys Pro Val Thr Asp
                965                 970                 975

Pro Leu Met Lys Arg Val Ser Glu Lys Val Asp Gln Ser Asn Val Thr
            980                 985                 990

Glu

<210> SEQ ID NO 5
<211> LENGTH: 2066
<212> TYPE: PRT
<213> ORGANISM: Staphylococcus aureus

<400> SEQUENCE: 5

Met Asn Glu Lys Val Glu Gly Met Thr Leu Glu Leu Lys Leu Asp His
1               5                   10                  15

Leu Gly Val Gln Glu Gly Met Lys Gly Leu Lys Arg Gln Leu Gly Val
            20                  25                  30

Val Asn Ser Glu Met Lys Ala Asn Leu Ser Ala Phe Asp Lys Ser Glu
        35                  40                  45

Lys Ser Met Glu Lys Tyr Gln Ala Arg Ile Lys Gly Leu Asn Asp Arg
    50                  55                  60

Leu Lys Val Gln Lys Lys Met Tyr Ser Gln Val Glu Asp Glu Leu Lys
65                  70                  75                  80

Gln Val Asn Ala Asn Tyr Gln Lys Ala Lys Ser Ser Val Lys Asp Val
                85                  90                  95

Glu Lys Ala Tyr Leu Lys Leu Val Glu Ala Asn Lys Glu Lys Leu
            100                 105                 110

Ala Leu Asp Lys Ser Lys Glu Ala Leu Lys Ser Ser Asn Thr Glu Leu
        115                 120                 125
```

```
Lys Lys Ala Glu Asn Gln Tyr Lys Arg Thr Asn Gln Arg Lys Gln Asp
    130                 135                 140
Ala Tyr Gln Lys Leu Lys Gln Leu Arg Asp Ala Glu Gln Lys Leu Lys
145                 150                 155                 160
Asn Ser Asn Gln Ala Thr Thr Ala Gln Leu Lys Arg Ala Ser Asp Ala
                165                 170                 175
Val Gln Lys Gln Ser Ala Lys His Lys Ala Leu Val Glu Gln Tyr Lys
            180                 185                 190
Gln Glu Gly Asn Gln Val Gln Lys Leu Lys Val Gln Asn Asp Asn Leu
        195                 200                 205
Ser Lys Ser Asn Asp Lys Ile Glu Ser Ser Tyr Ala Lys Thr Asn Thr
    210                 215                 220
Lys Leu Lys Gln Thr Glu Lys Glu Phe Asn Asp Leu Asn Asn Thr Ile
225                 230                 235                 240
Lys Asn His Ser Ala Asn Val Ala Lys Ala Glu Thr Ala Val Asn Lys
                245                 250                 255
Glu Lys Ala Ala Leu Asn Asn Leu Glu Arg Ser Ile Asp Lys Ala Ser
            260                 265                 270
Ser Glu Met Lys Thr Phe Asn Lys Glu Gln Met Ile Ala Gln Ser His
    275                 280                 285
Phe Gly Lys Leu Ala Ser Gln Ala Asp Val Met Ser Lys Lys Phe Ser
290                 295                 300
Ser Ile Gly Asp Lys Met Thr Ser Leu Gly Arg Thr Met Thr Met Gly
305                 310                 315                 320
Val Ser Thr Pro Ile Thr Leu Gly Leu Gly Ala Ala Leu Lys Thr Ser
                325                 330                 335
Ala Asp Phe Glu Gly Gln Met Ser Arg Val Gly Ala Ile Ala Gln Ala
            340                 345                 350
Ser Ser Lys Asp Leu Lys Ser Met Ser Asn Gln Ala Val Asp Leu Gly
    355                 360                 365
Ala Lys Thr Ser Lys Ser Ala Asn Glu Val Ala Lys Gly Met Glu Glu
370                 375                 380
Leu Ala Ala Leu Gly Phe Asn Ala Lys Gln Thr Met Glu Ala Met Pro
385                 390                 395                 400
Gly Val Ile Ser Ala Glu Ala Ser Gly Ala Glu Met Ala Thr Thr
                405                 410                 415
Ala Thr Val Met Ala Ser Ala Ile Asn Ser Phe Gly Leu Lys Ala Ser
            420                 425                 430
Asp Ala Asn His Val Ala Asp Leu Leu Ala Arg Ser Ala Asn Asp Ser
    435                 440                 445
Ala Ala Asp Ile Gln Tyr Met Gly Asp Ala Leu Lys Tyr Ala Gly Thr
450                 455                 460
Pro Ala Lys Ala Leu Gly Val Ser Ile Glu Asp Thr Ser Ala Ala Ile
465                 470                 475                 480
Glu Val Leu Ser Asn Ser Gly Leu Glu Gly Ser Gln Ala Gly Thr Ala
                485                 490                 495
Leu Arg Ala Ser Phe Ile Arg Leu Ala Asn Pro Ser Lys Asn Thr Ala
            500                 505                 510
Lys Glu Met Lys Lys Leu Gly Ile His Leu Ser Asp Ala Lys Gly Gln
    515                 520                 525
Phe Val Gly Met Gly Glu Leu Ile Arg Gln Phe Gln Asp Asn Met Lys
530                 535                 540
```

-continued

```
Gly Met Thr Arg Glu Gln Lys Leu Ala Thr Val Ala Thr Ile Val Gly
545                 550                 555                 560

Thr Glu Ala Ala Ser Gly Phe Leu Ala Leu Ile Glu Ala Gly Pro Asp
            565                 570                 575

Lys Ile Asn Ser Tyr Ser Lys Ser Leu Lys Asn Ser Asn Gly Glu Ser
            580                 585                 590

Lys Lys Ala Ala Asp Leu Met Lys Asp Asn Leu Lys Gly Ala Leu Glu
            595                 600                 605

Gln Leu Gly Gly Ala Phe Glu Ser Leu Ala Ile Glu Val Gly Lys Asp
            610                 615                 620

Leu Thr Pro Met Ile Arg Ala Gly Ala Glu Gly Leu Thr Lys Leu Val
625                 630                 635                 640

Asp Gly Phe Thr His Leu Pro Gly Trp Val Arg Lys Ala Ser Val Gly
            645                 650                 655

Leu Ala Leu Phe Gly Ala Ser Ile Gly Pro Ala Val Leu Ala Gly Gly
            660                 665                 670

Leu Leu Ile Arg Ala Val Gly Ser Ala Ala Lys Gly Tyr Ala Ser Leu
            675                 680                 685

Asn Arg Arg Ile Ala Glu Asn Thr Ile Leu Ser Asn Thr Asn Ser Lys
690                 695                 700

Ala Met Lys Ser Leu Gly Leu Gln Thr Leu Phe Leu Gly Ser Thr Thr
705                 710                 715                 720

Gly Lys Thr Ser Lys Gly Phe Lys Gly Leu Ala Gly Ala Met Leu Phe
            725                 730                 735

Asn Leu Lys Pro Ile Asn Val Leu Lys Asn Ser Ala Lys Leu Ala Ile
            740                 745                 750

Leu Pro Phe Lys Leu Leu Lys Asn Gly Leu Gly Leu Ala Ala Lys Ser
            755                 760                 765

Leu Phe Ala Val Ser Gly Ala Arg Phe Ala Gly Val Ala Leu Lys
            770                 775                 780

Phe Leu Thr Gly Pro Ile Gly Ala Thr Ile Thr Ala Ile Thr Ile Ala
785                 790                 795                 800

Tyr Lys Val Phe Lys Thr Ala Tyr Asp Arg Val Glu Trp Phe Arg Asn
            805                 810                 815

Gly Ile Asn Gly Leu Gly Glu Thr Ile Lys Phe Phe Gly Gly Lys Ile
            820                 825                 830

Ile Gly Gly Ala Val Arg Lys Leu Gly Glu Phe Lys Asn Tyr Leu Gly
            835                 840                 845

Ser Ile Gly Lys Ser Phe Lys Glu Lys Phe Ser Lys Asp Met Lys Asp
            850                 855                 860

Gly Tyr Lys Ser Leu Ser Asp Asp Leu Leu Lys Val Gly Val Asn
865                 870                 875                 880

Lys Phe Lys Gly Phe Met Gln Thr Met Gly Thr Ala Ser Lys Lys Ala
            885                 890                 895

Ser Asp Thr Val Lys Val Leu Gly Lys Gly Val Ser Lys Glu Thr Glu
            900                 905                 910

Lys Ala Leu Glu Lys Tyr Val His Tyr Ser Glu Glu Asn Asn Arg Ile
            915                 920                 925

Met Glu Lys Val Arg Leu Asn Ser Gly Gln Ile Thr Glu Asp Lys Ala
            930                 935                 940

Lys Lys Leu Leu Lys Ile Glu Ala Asp Leu Ser Asn Asn Leu Ile Ala
945                 950                 955                 960

Glu Ile Glu Lys Arg Asn Lys Lys Glu Leu Glu Lys Thr Gln Glu Leu
```

```
                965                 970                 975
Ile Asp Lys Tyr Ser Ala Phe Asp Glu Gln Glu Lys Gln Asn Ile Leu
            980                 985                 990
Thr Arg Thr Lys Glu Lys Asn Asp Leu Arg Ile Lys Lys Glu Gln Glu
        995                1000                1005
Leu Asn Gln Lys Ile Lys Glu Leu Lys Glu Lys Ala Leu Ser Asp
       1010                1015                1020
Gly Gln Ile Ser Glu Asn Glu Arg Lys Glu Ile Glu Lys Leu Glu
       1025                1030                1035
Asn Gln Arg Arg Asp Ile Thr Val Lys Glu Leu Ser Lys Thr Glu
       1040                1045                1050
Lys Glu Gln Glu Arg Ile Leu Val Arg Met Gln Arg Asn Arg Asn
       1055                1060                1065
Ser Tyr Ser Ile Asp Glu Ala Ser Lys Ala Ile Lys Glu Ala Glu
       1070                1075                1080
Lys Ala Arg Lys Ala Lys Lys Glu Val Asp Lys Gln Tyr Glu
       1085                1090                1095
Asp Asp Val Ile Ala Ile Lys Asn Asn Val Asn Leu Ser Lys Ser
       1100                1105                1110
Glu Lys Asp Lys Leu Leu Ala Ile Ala Asp Gln Arg His Lys Asp
       1115                1120                1125
Glu Val Arg Lys Ala Lys Ser Lys Lys Asp Ala Val Val Asp Val
       1130                1135                1140
Val Lys Lys Gln Asn Lys Asp Ile Asp Lys Glu Met Asp Leu Ser
       1145                1150                1155
Ser Gly Arg Val Tyr Lys Asn Thr Glu Lys Trp Trp Asn Gly Leu
       1160                1165                1170
Lys Ser Trp Trp Ser Asn Phe Arg Glu Asp Gln Lys Lys Lys Ser
       1175                1180                1185
Asp Lys Tyr Ala Lys Glu Gln Glu Glu Thr Ala Arg Arg Asn Arg
       1190                1195                1200
Glu Asn Ile Lys Lys Trp Phe Gly Asn Ala Trp Asp Gly Val Lys
       1205                1210                1215
Ser Lys Thr Gly Glu Ala Phe Ser Lys Met Gly Arg Asn Ala Asn
       1220                1225                1230
His Phe Gly Gly Glu Met Lys Lys Met Trp Ser Gly Ile Lys Gly
       1235                1240                1245
Ile Pro Ser Lys Leu Ser Ser Gly Trp Ser Ser Ala Lys Ser Ser
       1250                1255                1260
Val Gly Tyr His Thr Lys Ala Ile Ala Asn Ser Thr Gly Lys Trp
       1265                1270                1275
Phe Gly Lys Ala Trp Gln Ser Val Lys Ser Thr Thr Gly Ser Ile
       1280                1285                1290
Tyr Asn Gln Thr Lys Gln Lys Tyr Ser Asp Ala Ser Asp Lys Ala
       1295                1300                1305
Trp Ala His Ser Lys Ser Ile Trp Lys Gly Thr Ser Lys Trp Phe
       1310                1315                1320
Ser Asn Ala Tyr Lys Ser Ala Lys Gly Trp Leu Thr Asp Met Ala
       1325                1330                1335
Asn Lys Ser Arg Ser Lys Trp Asp Asn Ile Ser Ser Thr Ala Trp
       1340                1345                1350
Ser Asn Ala Lys Ser Val Trp Lys Gly Thr Ser Lys Trp Phe Ser
       1355                1360                1365
```

```
Asn Ser Tyr Lys Ser Leu Lys Gly Trp Thr Gly Asp Met Tyr Ser
    1370            1375            1380

Arg Ala His Asp Arg Phe Asp Ala Ile Ser Ser Ala Trp Ser
    1385            1390            1395

Asn Ala Lys Ser Val Phe Asn Gly Phe Arg Lys Trp Leu Ser Arg
    1400            1405            1410

Thr Tyr Glu Trp Ile Arg Asp Ile Gly Lys Asp Met Gly Arg Ala
    1415            1420            1425

Ala Ala Asp Leu Gly Lys Asn Val Ala Asn Lys Ala Ile Gly Gly
    1430            1435            1440

Leu Asn Ser Met Ile Gly Gly Ile Asn Lys Ile Ser Lys Ala Ile
    1445            1450            1455

Thr Asp Lys Asn Leu Ile Lys Pro Ile Pro Thr Leu Ser Thr Gly
    1460            1465            1470

Thr Leu Ala Gly Lys Gly Val Ala Thr Asp Asn Ser Gly Ala Leu
    1475            1480            1485

Thr Gln Pro Thr Phe Ala Val Leu Asn Asp Arg Gly Ser Gly Asn
    1490            1495            1500

Ala Pro Gly Gly Gly Val Gln Glu Val Ile His Arg Ala Asp Gly
    1505            1510            1515

Thr Phe His Ala Pro Gln Gly Arg Asp Val Val Pro Leu Gly
    1520            1525            1530

Val Gly Asp Ser Val Ile Asn Ala Asn Asp Thr Leu Lys Leu Gln
    1535            1540            1545

Arg Met Gly Val Leu Pro Lys Phe His Gly Gly Thr Lys Lys Lys
    1550            1555            1560

Lys Trp Met Glu Gln Val Thr Glu Asn Leu Gly Lys Lys Ala Gly
    1565            1570            1575

Asp Phe Gly Ser Lys Ala Lys Asn Thr Ala His Asn Ile Lys Lys
    1580            1585            1590

Gly Ala Glu Glu Met Val Glu Ala Ala Gly Asp Lys Ile Lys Asp
    1595            1600            1605

Gly Ala Ser Trp Leu Gly Asp Lys Ile Gly Asp Val Trp Asp Tyr
    1610            1615            1620

Val Gln His Pro Gly Lys Leu Val Asn Lys Val Met Ser Gly Leu
    1625            1630            1635

Asn Ile Asn Phe Gly Gly Gly Ala Asn Ala Thr Val Lys Ile Ala
    1640            1645            1650

Lys Gly Ala Tyr Ser Leu Leu Lys Lys Lys Leu Val Asp Lys Val
    1655            1660            1665

Lys Ser Trp Phe Glu Asp Phe Gly Gly Gly Gly Asp Gly Ser Tyr
    1670            1675            1680

Leu Phe Asp His Pro Ile Trp Gln Arg Phe Gly Ser Tyr Thr Gly
    1685            1690            1695

Gly Leu Asn Phe Asn Gly Gly Arg His Tyr Gly Ile Asp Phe Gln
    1700            1705            1710

Met Pro Thr Gly Thr Asn Ile Tyr Ala Val Lys Gly Gly Ile Ala
    1715            1720            1725

Asp Lys Val Trp Thr Asp Tyr Gly Gly Gly Asn Ser Ile Gln Ile
    1730            1735            1740

Lys Thr Gly Ala Asn Glu Trp Asn Trp Tyr Met His Leu Ser Lys
    1745            1750            1755
```

-continued

```
Gln Leu Ala Arg Gln Gly Gln Arg Ile Lys Ala Gly Gln Leu Ile
    1760                1765                1770
Gly Lys Ser Gly Ala Thr Gly Asn Phe Val Arg Gly Ala His Leu
1775                1780                1785
His Phe Gln Leu Met Gln Gly Ser His Pro Gly Asn Asp Thr Ala
    1790                1795                1800
Lys Asp Pro Glu Lys Trp Leu Lys Ser Leu Lys Gly Ser Gly Val
1805                1810                1815
Arg Ser Gly Ser Gly Val Asn Lys Ala Ser Ala Trp Ala Gly
    1820                1825                1830
Asp Ile Arg Arg Ala Ala Lys Arg Met Gly Val Asn Val Thr Ser
1835                1840                1845
Gly Asp Val Gly Asn Ile Ile Ser Leu Ile Gln His Glu Ser Gly
    1850                1855                1860
Gly Asn Ala Gly Ile Thr Gln Ser Ser Ala Leu Arg Asp Ile Asn
1865                1870                1875
Val Leu Gln Gly Asn Pro Ala Lys Gly Leu Leu Gln Tyr Ile Pro
    1880                1885                1890
Gln Thr Phe Arg His Tyr Ala Val Arg Gly His Asn Asn Ile Tyr
1895                1900                1905
Ser Gly Tyr Asp Gln Leu Leu Ala Phe Phe Asn Asn Ser Tyr Trp
    1910                1915                1920
Arg Ser Gln Phe Asn Pro Arg Gly Gly Trp Ser Pro Ser Gly Pro
1925                1930                1935
Arg Arg Tyr Ala Asn Gly Gly Leu Ile Thr Lys His Gln Leu Ala
    1940                1945                1950
Glu Val Gly Glu Gly Asp Lys Gln Glu Met Val Ile Pro Leu Thr
1955                1960                1965
Arg Arg Lys Arg Ala Ile Gln Leu Thr Glu Gln Val Met Arg Ile
    1970                1975                1980
Ile Gly Met Asp Gly Lys Pro Asn Asn Ile Thr Val Asn Asn Asp
1985                1990                1995
Thr Ser Thr Val Glu Lys Leu Leu Lys Gln Ile Val Met Leu Ser
2000                2005                2010
Asp Lys Gly Asn Lys Leu Thr Asp Ala Leu Ile Gln Thr Val Ser
2015                2020                2025
Ser Gln Asp Asn Asn Leu Gly Ser Asn Asp Ala Ile Arg Gly Leu
    2030                2035                2040
Glu Lys Ile Leu Ser Lys Gln Ser Gly His Arg Ala Asn Ala Asn
2045                2050                2055
Asn Tyr Met Gly Gly Leu Thr Asn
    2060                2065
```

<210> SEQ ID NO 6
<211> LENGTH: 609
<212> TYPE: PRT
<213> ORGANISM: Staphylococcus aureus

<400> SEQUENCE: 6

```
Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Asn Ser Lys Tyr Asp Thr Pro Ile
            35                  40                  45
```

```
Pro Asp Trp Tyr Leu Gly Ser Ile Leu Asn Arg Leu Gly Asp Gln Ile
     50                  55                  60

Tyr Tyr Ala Lys Glu Leu Thr Asn Lys Tyr Glu Tyr Gly Glu Lys Glu
 65                  70                  75                  80

Tyr Lys Gln Ala Ile Asp Lys Leu Met Thr Arg Val Leu Gly Glu Asp
                 85                  90                  95

His Tyr Leu Leu Glu Lys Lys Ala Gln Tyr Glu Ala Tyr Lys Lys
            100                 105                 110

Trp Phe Glu Lys His Lys Ser Glu Asn Pro His Ser Ser Leu Lys Lys
        115                 120                 125

Ile Lys Phe Asp Asp Phe Asp Leu Tyr Arg Leu Thr Lys Lys Glu Tyr
    130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190

Glu Ile Asp Thr Leu Tyr Ala Ala Tyr Phe Asn His Ser Gln Tyr Gly
    195                 200                 205

His Asn Ala Lys Glu Leu Arg Ala Lys Leu Asp Ile Ile Leu Gly Asp
        210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
    275                 280                 285

Glu Thr Arg Glu Ala Ile Ala Asn Ala Asp Glu Ser Trp Lys Thr Arg
290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
                325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
    355                 360                 365

Ile Val Lys Gly Pro Glu Tyr Leu Thr Met Glu Asn Lys Thr Leu Gln
    370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
                405                 410                 415

Leu Lys Gly Ile Glu Gly Asn Ser Thr Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Thr Glu Ala Ser His Tyr Pro
450                 455                 460
```

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
            485                 490                 495

Ala Arg Pro Arg Phe Asn Lys Pro Ser Glu Thr Asn Ala Tyr Asn Val
        500                 505                 510

Thr Thr Asn Gln Asp Gly Thr Val Ser Tyr Gly Ala Arg Pro Thr Gln
            515                 520                 525

Asn Lys Pro Ser Glu Thr Asn Ala Tyr Asn Val Thr His Ala Asn
    530                 535                 540

Gly Gln Val Ser Tyr Gly Ala Arg Pro Thr Gln Asn Lys Pro Ser Glu
545                 550                 555                 560

Thr Asn Ala Tyr Asn Val Thr Thr His Ala Asn Gly Gln Val Ser Tyr
            565                 570                 575

Gly Ala Arg Pro Thr Gln Asn Lys Pro Ser Lys Thr Asn Ala Tyr Asn
        580                 585                 590

Val Thr Thr His Ala Asp Gly Thr Ala Thr Tyr Gly Pro Arg Val Thr
            595                 600                 605

Lys

<210> SEQ ID NO 7
<211> LENGTH: 144
<212> TYPE: PRT
<213> ORGANISM: Staphylococcus aureus

<400> SEQUENCE: 7

Met Lys Lys Val Ile Gly Leu Leu Leu Val Ser Thr Leu Ala Leu Thr
1               5                   10                  15

Ala Cys Gly Glu Lys Glu Lys Pro Lys Lys Glu Glu Asn Lys Lys Ser
            20                  25                  30

Gln Thr Gln Lys His Lys Asp Ser Lys Pro Lys Thr Gln Gln Glu Lys
        35                  40                  45

Met Lys Lys Val Glu Asp Lys Asn Pro Pro Asn Asn Ser Ile Gln Asn
    50                  55                  60

Asn Ser Asn Asn Gln Asn Gln Ser Gln Asn Asn Gln Leu Asn Asn
65                  70                  75                  80

Ser Asp Pro Ser Asn Asn Thr Pro Ala Asn Ile Asn Lys Asn Asp Ser
                85                  90                  95

Gln Asn Thr Asn Leu Asn Asp Glu Tyr Val Val Ser Pro Gly Trp Thr
            100                 105                 110

Lys Asp Glu Gln Ala Lys Ala Phe Glu Glu Tyr Lys Lys Gly Lys Glu
        115                 120                 125

Asp Glu Ala Arg Ala Gly Ala Ser Ala Val Pro Gly Ala Asn Ile Asn
    130                 135                 140

<210> SEQ ID NO 8
<211> LENGTH: 1257
<212> TYPE: PRT
<213> ORGANISM: Staphylococcus aureus

<400> SEQUENCE: 8

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val

```
                35                  40                  45
Lys Ala Thr Thr Glu Gln Ala Lys Ala Glu Val Lys Asn Pro Thr Gln
 50                  55                  60
Asn Ile Ser Gly Thr Gln Val Tyr Gln Asp Pro Ala Ile Val Gln Pro
 65                  70                  75                  80
Lys Ala Ala Asn Lys Thr Gly Asn Ala Gln Val Asn Gln Lys Val Asp
                 85                  90                  95
Thr Thr Gln Val Asn Gly Asp Thr Arg Ala Thr Gln Ser Thr Thr Ser
                100                 105                 110
Asn Asn Ala Lys Pro Val Thr Lys Ser Thr Asn Thr Thr Ala Pro Lys
            115                 120                 125
Thr Asn Asn Asn Val Thr Ser Ala Gly Tyr Ser Leu Val Asp Asp Glu
130                 135                 140
Asp Asp Asn Ser Glu Asn Gln Ile Asn Pro Glu Leu Ile Lys Ser Ala
145                 150                 155                 160
Ala Lys Pro Ala Ala Leu Glu Thr Gln Tyr Lys Ala Ala Pro Lys
                165                 170                 175
Ala Thr Pro Val Ala Pro Lys Ala Lys Thr Glu Ala Thr Pro Lys Val
                180                 185                 190
Thr Thr Phe Ser Ala Ser Ala Gln Pro Arg Ser Ala Ala Ala Pro
            195                 200                 205
Lys Thr Ser Leu Pro Lys Tyr Lys Pro Gln Val Asn Ser Ser Ile Asn
210                 215                 220
Asp Tyr Ile Arg Lys Asn Asn Leu Lys Ala Pro Lys Ile Glu Glu Asp
225                 230                 235                 240
Tyr Thr Ser Tyr Phe Pro Lys Tyr Ala Tyr Arg Asn Gly Val Gly Arg
                245                 250                 255
Pro Glu Gly Ile Val Val His Asp Thr Ala Asn Asp Arg Ser Thr Ile
                260                 265                 270
Asn Gly Glu Ile Ser Tyr Met Lys Asn Asn Tyr Gln Asn Ala Phe Val
            275                 280                 285
His Ala Phe Val Asp Gly Asp Arg Ile Ile Glu Thr Ala Pro Thr Asp
290                 295                 300
Tyr Leu Ser Trp Gly Val Gly Ala Val Gly Asn Pro Arg Phe Ile Asn
305                 310                 315                 320
Val Glu Ile Val His Thr His Asp Tyr Ala Ser Phe Ala Arg Ser Met
                325                 330                 335
Asn Asn Tyr Ala Asp Tyr Ala Ala Thr Gln Leu Gln Tyr Tyr Gly Leu
            340                 345                 350
Lys Pro Asp Ser Ala Glu Tyr Asp Gly Asn Gly Thr Val Trp Thr His
            355                 360                 365
Tyr Ala Val Ser Lys Tyr Leu Gly Gly Thr Asp His Ala Asp Pro His
            370                 375                 380
Gly Tyr Leu Arg Ser His Asn Tyr Ser Tyr Asp Gln Leu Tyr Asp Leu
385                 390                 395                 400
Ile Asn Glu Lys Tyr Leu Ile Lys Met Gly Lys Val Ala Pro Trp Gly
                405                 410                 415
Thr Gln Ser Thr Thr Thr Pro Thr Pro Ser Lys Pro Ser Thr Pro
            420                 425                 430
Ser Lys Pro Ser Thr Pro Ser Thr Gly Lys Leu Thr Val Ala Ala Asn
            435                 440                 445
Asn Gly Val Ala Gln Ile Lys Pro Thr Asn Ser Gly Leu Tyr Thr Thr
450                 455                 460
```

```
Val Tyr Asp Lys Thr Gly Lys Ala Thr Asn Glu Val Gln Lys Thr Phe
465                 470                 475                 480

Ala Val Ser Lys Thr Ala Thr Leu Gly Asn Gln Lys Phe Tyr Leu Val
                485                 490                 495

Gln Asp Tyr Asn Ser Gly Asn Lys Phe Gly Trp Val Lys Glu Gly Asp
            500                 505                 510

Val Val Tyr Asn Thr Ala Lys Ser Pro Val Asn Val Asn Gln Ser Tyr
        515                 520                 525

Ser Ile Lys Pro Gly Thr Lys Leu Tyr Thr Val Pro Trp Gly Thr Ser
    530                 535                 540

Lys Gln Val Ala Gly Ser Val Ser Gly Ser Asn Gln Thr Phe Lys
545                 550                 555                 560

Ala Ser Lys Gln Gln Gln Ile Asp Lys Ser Ile Tyr Leu Tyr Gly Ser
                565                 570                 575

Val Asn Gly Lys Ser Gly Trp Val Ser Lys Ala Tyr Leu Val Asp Thr
            580                 585                 590

Ala Lys Pro Thr Pro Thr Pro Thr Pro Lys Pro Ser Thr Pro Thr Thr
        595                 600                 605

Asn Asn Lys Leu Thr Val Ser Ser Leu Asn Gly Val Ala Gln Ile Asn
    610                 615                 620

Ala Lys Asn Asn Gly Leu Phe Thr Thr Val Tyr Asp Lys Thr Gly Lys
625                 630                 635                 640

Pro Thr Lys Glu Val Gln Lys Thr Phe Ala Val Thr Lys Glu Ala Ser
                645                 650                 655

Leu Gly Gly Asn Lys Phe Tyr Leu Val Lys Asp Tyr Asn Ser Pro Thr
            660                 665                 670

Leu Ile Gly Trp Val Lys Gln Gly Asp Val Ile Tyr Asn Asn Ala Lys
        675                 680                 685

Ser Pro Val Asn Val Met Gln Thr Tyr Thr Val Lys Pro Gly Thr Lys
    690                 695                 700

Leu Tyr Ser Val Pro Trp Gly Thr Tyr Lys Gln Glu Ala Gly Ala Val
705                 710                 715                 720

Ser Gly Thr Gly Asn Gln Thr Phe Lys Ala Thr Lys Gln Gln Ile
                725                 730                 735

Asp Lys Ser Ile Tyr Leu Tyr Gly Thr Val Asn Gly Lys Ser Gly Trp
            740                 745                 750

Ile Ser Lys Ala Tyr Leu Ala Val Pro Ala Ala Pro Lys Lys Ala Val
        755                 760                 765

Ala Gln Pro Lys Thr Ala Val Lys Ala Tyr Ala Val Thr Lys Pro Gln
770                 775                 780

Thr Thr Gln Thr Val Ser Lys Ile Ala Gln Val Lys Pro Asn Asn Thr
785                 790                 795                 800

Gly Ile Arg Ala Ser Val Tyr Glu Lys Thr Ala Lys Asn Gly Ala Lys
                805                 810                 815

Tyr Ala Asp Arg Thr Phe Tyr Val Thr Lys Glu Arg Ala His Gly Asn
            820                 825                 830

Glu Thr Tyr Val Leu Leu Asn Asn Thr Ser His Asn Ile Pro Leu Gly
        835                 840                 845

Trp Phe Asn Val Lys Asp Leu Asn Val Gln Asn Leu Gly Lys Glu Val
    850                 855                 860

Lys Thr Thr Gln Lys Tyr Thr Val Asn Arg Ser Asn Asn Gly Leu Ser
865                 870                 875                 880
```

Met Val Pro Trp Gly Thr Lys Asn Gln Val Ile Leu Thr Gly Asn Asn
            885                 890                 895

Ile Ala Gln Gly Thr Phe Asn Ala Thr Lys Gln Val Ser Val Gly Lys
        900                 905                 910

Asp Val Tyr Leu Tyr Gly Thr Ile Asn Asn Arg Thr Gly Trp Val Asn
        915                 920                 925

Ser Lys Asp Leu Thr Ala Pro Thr Ala Val Lys Pro Thr Thr Ser Ala
    930                 935                 940

Ala Lys Asp Tyr Asn Tyr Thr Tyr Val Ile Lys Asn Gly Asn Gly Tyr
945                 950                 955                 960

Tyr Tyr Val Thr Pro Asn Ser Asp Thr Ala Lys Tyr Ser Leu Lys Ala
            965                 970                 975

Phe Asn Glu Gln Pro Phe Ala Val Val Lys Glu Gln Val Ile Asn Gly
            980                 985                 990

Gln Thr Trp Tyr Tyr Gly Lys Leu Ser Asn Gly Lys Leu Ala Trp Ile
        995                 1000                1005

Lys Ser Thr Asp Leu Ala Lys Glu Leu Ile Lys Tyr Asn Gln Ile
    1010                1015                1020

Gly Met Thr Leu Asn Gln Val Ala Gln Ile Gln Ala Gly Leu Gln
    1025                1030                1035

Tyr Lys Pro Gln Val Gln Arg Val Pro Gly Lys Trp Thr Asp Ala
    1040                1045                1050

Asn Phe Asn Asp Val Lys His Ala Met Asp Thr Lys Arg Leu Ala
    1055                1060                1065

Gln Asp Pro Ala Leu Lys Tyr Gln Phe Leu Arg Leu Asp Gln Pro
    1070                1075                1080

Gln Asn Ile Ser Ile Asp Lys Ile Asn Gln Phe Leu Lys Gly Lys
    1085                1090                1095

Gly Val Leu Glu Asn Gln Gly Ala Ala Phe Asn Lys Ala Ala Gln
    1100                1105                1110

Met Tyr Gly Ile Asn Glu Val Tyr Leu Ile Ser His Ala Leu Leu
    1115                1120                1125

Glu Thr Gly Asn Gly Thr Ser Gln Leu Ala Lys Gly Ala Asp Val
    1130                1135                1140

Val Asn Asn Lys Val Val Thr Asn Ser Asn Thr Lys Tyr His Asn
    1145                1150                1155

Val Phe Gly Ile Ala Ala Tyr Asp Asn Asp Pro Leu Arg Glu Gly
    1160                1165                1170

Ile Lys Tyr Ala Lys Gln Ala Gly Trp Asp Thr Val Ser Lys Ala
    1175                1180                1185

Ile Val Gly Gly Ala Lys Phe Ile Gly Asn Ser Tyr Val Lys Ala
    1190                1195                1200

Gly Gln Asn Thr Leu Tyr Lys Met Arg Trp Asn Pro Ala His Pro
    1205                1210                1215

Gly Thr His Gln Tyr Ala Thr Asp Val Asp Trp Ala Asn Ile Asn
    1220                1225                1230

Ala Lys Ile Ile Lys Gly Tyr Tyr Asp Lys Ile Gly Glu Val Gly
    1235                1240                1245

Lys Tyr Phe Asp Ile Pro Gln Tyr Lys
    1250                1255

<210> SEQ ID NO 9
<211> LENGTH: 486
<212> TYPE: PRT

<213> ORGANISM: Staphylococcus aureus

<400> SEQUENCE: 9

```
Met Ser Asn Asn Phe Lys Asp Asp Phe Glu Lys Asn Arg Gln Ser Ile
1               5                   10                  15

Asp Thr Asn Ser His Gln Asp His Thr Glu Asp Val Glu Lys Asp Gln
            20                  25                  30

Ser Glu Leu Glu His Gln Asp Thr Ile Glu Asn Thr Glu Gln Gln Phe
        35                  40                  45

Pro Pro Arg Asn Ala Gln Arg Arg Lys Arg Arg Arg Asp Leu Ala Thr
    50                  55                  60

Asn His Asn Lys Gln Val His Asn Glu Ser Gln Thr Ser Glu Asp Asn
65                  70                  75                  80

Val Gln Asn Glu Ala Gly Thr Ile Asp Asp Arg Gln Val Glu Ser Ser
                85                  90                  95

His Ser Thr Glu Ser Gln Glu Pro Ser His Gln Asp Ser Thr Pro Gln
            100                 105                 110

His Glu Glu Gly Tyr Tyr Asn Lys Asn Ala Phe Ala Met Asp Lys Ser
        115                 120                 125

His Pro Glu Pro Ile Glu Asp Asn Asp Lys His Glu Thr Ile Lys Glu
    130                 135                 140

Ala Glu Asn Asn Thr Glu His Ser Thr Val Ser Asp Lys Ser Glu Ala
145                 150                 155                 160

Glu Gln Ser Gln Gln Pro Lys Pro Tyr Phe Ala Thr Gly Ala Asn Gln
                165                 170                 175

Ala Asn Thr Ser Lys Asp Lys His Asp Asp Val Thr Val Lys Gln Asp
            180                 185                 190

Lys Asp Glu Ser Lys Asp His His Ser Gly Lys Lys Gly Ala Ala Ile
        195                 200                 205

Gly Ala Gly Thr Ala Gly Val Ala Gly Ala Ala Gly Ala Met Gly Val
    210                 215                 220

Ser Lys Ala Lys Lys His Ser Asn Asp Ala Gln Asn Lys Ser Asn Ser
225                 230                 235                 240

Gly Lys Val Asn Asn Ser Thr Glu Asp Lys Ala Ser Glu Asp Lys Ser
                245                 250                 255

Lys Glu His His Asn Gly Lys Lys Gly Ala Ala Ile Gly Ala Gly Thr
            260                 265                 270

Ala Gly Leu Ala Gly Gly Ala Ala Ser Asn Ser Ala Ser Ala Ala Ser
        275                 280                 285

Lys Pro His Ala Ser Asn Asn Ala Ser Gln Asn Asn Asp Glu His Asp
    290                 295                 300

His His Asp Arg Asp Lys Glu Arg Lys Lys Gly Gly Met Ala Lys Val
305                 310                 315                 320

Leu Leu Pro Leu Ile Ala Ala Val Leu Ile Ile Gly Ala Leu Ala Ile
                325                 330                 335

Phe Gly Gly Met Ala Leu Asn Asn His Asn Asn Gly Thr Lys Glu Asn
            340                 345                 350

Lys Ile Ala Asn Thr Asn Lys Asn Asn Ala Asp Glu Ser Lys Asp Lys
        355                 360                 365

Asp Thr Ser Lys Asp Ala Ser Lys Asp Lys Ser Thr Asp Ser
    370                 375                 380

Asp Lys Ser Lys Asp Asp Gln Asp Lys Ala Thr Lys Asp Glu Ser Asp
385                 390                 395                 400
```

```
Asn Asp Gln Asn Asn Ala Gln Ala Asn Asn Gln Ala Gln Asn Asn
                    405                 410                 415

Gln Asn Gln Gln Gln Ala Asn Gln Gln Gln Gln Gln Gln Arg
            420                 425                 430

Gln Gly Gly Gly Gln Arg His Thr Val Asn Gly Gln Glu Asn Leu Tyr
            435                 440                 445

Arg Ile Ala Ile Gln Tyr Tyr Gly Ser Gly Ser Pro Glu Asn Val Glu
        450                 455                 460

Lys Ile Arg Arg Ala Asn Gly Leu Ser Gly Asn Asn Ile Arg Asn Gly
465                 470                 475                 480

Gln Gln Ile Val Ile Pro
                485

<210> SEQ ID NO 10
<211> LENGTH: 1274
<212> TYPE: PRT
<213> ORGANISM: Staphylococcus aureus

<400> SEQUENCE: 10

Met Ser Trp Phe Asp Lys Leu Phe Gly Glu Asp Asn Asp Ser Asn Asp
1               5                   10                  15

Asp Leu Ile His Arg Lys Lys Arg Arg Gln Glu Ser Gln Asn Ile
            20                  25                  30

Asp Asn Asp His Asp Ser Leu Leu Pro Gln Asn Asn Asp Ile Tyr Ser
        35                  40                  45

Arg Pro Arg Gly Lys Phe Arg Phe Pro Met Ser Val Ala Tyr Glu Asn
    50                  55                  60

Glu Asn Val Glu Gln Ser Ala Asp Thr Ile Ser Asp Glu Lys Glu Gln
65                  70                  75                  80

Tyr His Arg Asp Tyr Arg Lys Gln Ser His Asp Ser Arg Ser Gln Lys
                85                  90                  95

Arg His Arg Arg Arg Asn Gln Thr Thr Glu Glu Gln Asn Tyr Ser
            100                 105                 110

Glu Gln Arg Gly Asn Ser Lys Ile Ser Gln Gln Ser Ile Lys Tyr Lys
        115                 120                 125

Asp His Ser His Tyr His Thr Asn Lys Pro Gly Thr Tyr Val Ser Ala
    130                 135                 140

Ile Asn Gly Ile Glu Lys Glu Thr His Lys Ser Lys Thr His Asn Ile
145                 150                 155                 160

Tyr Ser Asn Asn Thr Asn His Arg Ala Lys Asp Ser Thr Thr Asp Tyr
                165                 170                 175

His Lys Glu Ser Phe Lys Thr Ser Glu Val Pro Ser Ala Ile Phe Gly
            180                 185                 190

Thr Met Lys Pro Lys Lys Leu Glu Asn Gly Arg Ile Pro Val Ser Lys
        195                 200                 205

Ser Ser Glu Lys Val Glu Ser Asp Lys Gln Lys Tyr Asp Lys Tyr Val
    210                 215                 220

Ala Lys Thr Gln Thr Ser Gln Asn Lys His Leu Glu Gln Glu Lys Gln
225                 230                 235                 240

Lys Asp Ser Val Val Lys Gln Gly Thr Ala Ser Lys Ser Ser Asp Glu
                245                 250                 255

Asn Val Ser Ser Thr Thr Lys Ser Thr Pro Asn Tyr Ser Lys Val Asp
            260                 265                 270

Asn Thr Ile Lys Ile Glu Asn Ile Tyr Ala Ser Gln Ile Val Glu Glu
        275                 280                 285
```

```
Ile Arg Arg Glu Arg Glu Arg Lys Val Leu Gln Lys Arg Arg Phe Lys
    290                 295                 300

Lys Ala Leu Gln Gln Lys Arg Glu Glu His Lys Asn Glu Glu Gln Asp
305                 310                 315                 320

Ala Ile Gln Arg Ala Ile Asp Glu Met Tyr Ala Lys Gln Ala Glu Arg
                325                 330                 335

Tyr Val Gly Asp Ser Ser Leu Asn Asp Asp Ser Asp Leu Thr Asp Asn
                340                 345                 350

Ser Thr Glu Ala Ser Gln Leu His Thr Asn Glu Ile Glu Asp Glu Ala
            355                 360                 365

Val Ser Asn Asp Glu Asn Lys Lys Ala Ser Ile Gln Asn Glu Asp Thr
370                 375                 380

Asp Asp Thr His Val Asp Glu Ser Pro Tyr Asn Tyr Glu Glu Val Ser
385                 390                 395                 400

Leu Asn Gln Val Ser Thr Thr Lys Gln Leu Ser Asp Asp Glu Val Thr
                405                 410                 415

Val Ser Asp Val Thr Ser Gln Arg Gln Ser Ala Leu Gln His Asn Val
                420                 425                 430

Glu Val Asn Asn Gln Asp Glu Leu Lys Asn Gln Ser Arg Leu Ile Ala
            435                 440                 445

Asp Ser Glu Glu Asp Gly Ala Thr Asn Glu Glu Tyr Ser Gly Ser
450                 455                 460

Gln Ile Asp Asp Ala Glu Phe Tyr Glu Leu Asn Asp Thr Glu Val Asp
465                 470                 475                 480

Glu Asp Thr Thr Ser Asn Ser Glu Asp Asn Thr Asn Arg Asp Ala Ser
                485                 490                 495

Glu Met His Val Asp Ala Pro Lys Thr Gln Glu His Ala Val Thr Glu
            500                 505                 510

Ser Gln Val Asn Asn Ile Asp Lys Thr Val Asp Asn Glu Ile Glu Leu
            515                 520                 525

Ala Pro Arg His Lys Lys Asp Asp Gln Thr Asn Leu Ser Val Asn Ser
530                 535                 540

Leu Lys Thr Asn Asp Val Asn Asp Gly His Val Val Glu Asp Ser Ser
545                 550                 555                 560

Met Asn Glu Ile Glu Lys Gln Asn Ala Glu Ile Thr Glu Asn Val Gln
                565                 570                 575

Asn Glu Ala Ala Glu Ser Lys Gln Asn Val Glu Glu Lys Thr Ile Glu
            580                 585                 590

Asn Val Asn Pro Lys Lys Gln Thr Glu Lys Val Ser Thr Leu Ser Lys
            595                 600                 605

Arg Pro Phe Asn Val Val Met Thr Pro Ser Asp Lys Lys Arg Met Met
610                 615                 620

Asp Arg Lys Lys His Ser Lys Val Asn Val Pro Glu Leu Lys Pro Val
625                 630                 635                 640

Gln Ser Lys Gln Ala Ala Ser Glu Ser Lys Thr Ala Thr Gln Asn Thr
                645                 650                 655

Pro Ser Ser Ser Thr Asp Ser Gln Glu Ser Asn Thr Asn Ala Tyr Lys
                660                 665                 670

Thr Asn Asn Met Thr Ser Asn Asn Val Glu Asn Asn Gln Leu Ile Gly
            675                 680                 685

His Ala Ala Thr Glu Asn Asp Tyr Gln Asn Ala Gln Gln Tyr Ser Glu
690                 695                 700
```

-continued

```
Gln Lys Pro Ser Ala Asp Ser Thr Gln Thr Glu Ile Phe Glu Glu Ser
705                 710                 715                 720

Gln Asp Asp Asn Gln Leu Glu Asn Glu Gln Val Asp Gln Ser Thr Ser
            725                 730                 735

Ser Ser Val Ser Glu Val Ser Asp Ile Thr Glu Glu Ser Glu Glu Thr
        740                 745                 750

Thr His Gln Asn Asn Thr Ser Gly Gln Gln Asp Asn Asp Asp Gln Gln
            755                 760                 765

Lys Asp Leu Gln Leu Ser Phe Ser Asn Gln Asn Glu Asp Thr Ala Asn
    770                 775                 780

Glu Asn Arg Pro Arg Thr Asn Gln Pro Asp Val Ala Thr Asn Gln Ala
785                 790                 795                 800

Val Gln Thr Ser Lys Pro Met Ile Arg Lys Gly Pro Asn Ile Lys Leu
            805                 810                 815

Pro Ser Val Ser Leu Leu Glu Glu Pro Gln Val Ile Glu Pro Asp Glu
        820                 825                 830

Asp Trp Ile Thr Asp Lys Lys Lys Glu Leu Asn Asp Ala Leu Phe Tyr
            835                 840                 845

Phe Asn Val Pro Ala Glu Val Gln Asp Val Thr Glu Gly Pro Ser Val
850                 855                 860

Thr Arg Phe Glu Leu Ser Val Glu Lys Gly Val Lys Val Ser Arg Ile
865                 870                 875                 880

Thr Ala Leu Gln Asp Asp Ile Lys Met Ala Leu Ala Ala Lys Asp Ile
            885                 890                 895

Arg Ile Glu Ala Pro Ile Pro Gly Thr Ser Arg Val Gly Ile Glu Val
            900                 905                 910

Pro Asn Gln Asn Pro Thr Thr Val Asn Leu Arg Ser Ile Ile Glu Ser
            915                 920                 925

Pro Ser Phe Lys Asn Ala Glu Ser Lys Leu Thr Val Ala Met Gly Tyr
        930                 935                 940

Arg Ile Asn Asn Glu Pro Leu Leu Met Asp Ile Ala Lys Thr Pro His
945                 950                 955                 960

Ala Leu Ile Ala Gly Ala Thr Gly Ser Gly Lys Ser Val Cys Ile Asn
            965                 970                 975

Ser Ile Leu Met Ser Leu Leu Tyr Lys Asn His Pro Glu Glu Leu Arg
        980                 985                 990

Leu Leu Leu Ile Asp Pro Lys Met Val Glu Leu Ala Pro Tyr Asn Gly
            995                1000                1005

Leu Pro His Leu Val Ala Pro Val Ile Thr Asp Val Lys Ala Ala
    1010                1015                1020

Thr Gln Ser Leu Lys Trp Ala Val Glu Glu Met Glu Arg Arg Tyr
    1025                1030                1035

Lys Leu Phe Ala His Tyr His Val Arg Asn Ile Thr Ala Phe Asn
    1040                1045                1050

Lys Lys Ala Pro Tyr Asp Glu Arg Met Pro Lys Ile Val Ile Val
    1055                1060                1065

Ile Asp Glu Leu Ala Asp Leu Met Met Met Ala Pro Gln Glu Val
    1070                1075                1080

Glu Gln Ser Ile Ala Arg Ile Ala Gln Lys Ala Arg Ala Cys Gly
    1085                1090                1095

Ile His Met Leu Val Ala Thr Gln Arg Pro Ser Val Asn Val Ile
    1100                1105                1110

Thr Gly Leu Ile Lys Ala Asn Ile Pro Thr Arg Ile Ala Phe Met
```

```
             1115                1120                1125

Val Ser Ser Ser Val Asp Ser Arg Thr Ile Leu Asp Ser Gly Gly
            1130                1135                1140

Ala Glu Arg Leu Leu Gly Tyr Gly Asp Met Leu Tyr Leu Gly Ser
            1145                1150                1155

Gly Met Asn Lys Pro Ile Arg Val Gln Gly Thr Phe Val Ser Asp
            1160                1165                1170

Asp Glu Ile Asp Asp Val Val Asp Phe Ile Lys Gln Gln Arg Glu
            1175                1180                1185

Pro Asp Tyr Leu Phe Glu Glu Lys Glu Leu Leu Lys Lys Thr Gln
            1190                1195                1200

Thr Gln Ser Gln Asp Glu Leu Phe Asp Asp Val Cys Ala Phe Met
            1205                1210                1215

Val Asn Glu Gly His Ile Ser Thr Ser Leu Ile Gln Arg His Phe
            1220                1225                1230

Gln Ile Gly Tyr Asn Arg Ala Ala Arg Ile Ile Asp Gln Leu Glu
            1235                1240                1245

Gln Leu Gly Tyr Val Ser Ser Ala Asn Gly Ser Lys Pro Arg Asp
            1250                1255                1260

Val Tyr Val Thr Glu Ala Asp Leu Asn Lys Glu
            1265                1270

<210> SEQ ID NO 11
<211> LENGTH: 209
<212> TYPE: PRT
<213> ORGANISM: Staphylococcus aureus

<400> SEQUENCE: 11

Met Ser Asn Gln Asn Tyr Asp Tyr Asn Lys Asn Glu Asp Gly Ser Lys
1               5                   10                  15

Lys Lys Met Ser Thr Thr Ala Lys Val Val Ser Ile Ala Thr Val Leu
            20                  25                  30

Leu Leu Leu Gly Gly Leu Val Phe Ala Ile Phe Ala Tyr Val Asp His
        35                  40                  45

Ser Asn Lys Ala Lys Glu Arg Met Leu Asn Glu Gln Lys Gln Glu Gln
    50                  55                  60

Lys Glu Lys Arg Gln Lys Glu Asn Ala Glu Lys Glu Arg Lys Lys Lys
65                  70                  75                  80

Gln Gln Glu Glu Lys Glu Gln Asn Glu Leu Asp Ser Gln Ala Asn Gln
                85                  90                  95

Tyr Gln Gln Leu Pro Gln Gln Asn Gln Tyr Gln Tyr Val Pro Pro Gln
            100                 105                 110

Gln Gln Ala Pro Thr Lys Gln Arg Pro Ala Lys Glu Glu Asn Asp Asp
        115                 120                 125

Lys Ala Ser Lys Asp Glu Ser Lys Asp Lys Asp Lys Ala Ser Gln
    130                 135                 140

Asp Lys Ser Asp Asp Asn Gln Lys Lys Thr Asp Asp Asn Lys Gln Pro
145                 150                 155                 160

Ala Gln Pro Lys Pro Gln Pro Gln Pro Thr Pro Lys Pro Asn Asn
            165                 170                 175

Asn Gln Gln Asn Asn Gln Ser Asn Gln Ala Lys Pro Gln Ala Pro
        180                 185                 190

Gln Gln Asn Ser Gln Ser Thr Thr Asn Lys Gln Asn Asn Ala Asn Asp
    195                 200                 205
```

Lys

<210> SEQ ID NO 12
<211> LENGTH: 190
<212> TYPE: PRT
<213> ORGANISM: Staphylococcus aureus

<400> SEQUENCE: 12

Met Lys Leu Lys Ser Leu Ala Val Leu Ser Met Ser Ala Val Val Leu
1               5                   10                  15

Thr Ala Cys Gly Asn Asp Thr Pro Lys Asp Glu Thr Lys Ser Thr Glu
            20                  25                  30

Ser Asn Thr Asn Gln Asp Thr Asn Thr Thr Lys Asp Val Ile Ala Leu
        35                  40                  45

Lys Asp Val Lys Thr Ser Pro Glu Asp Ala Val Lys Lys Ala Glu Glu
50                  55                  60

Thr Tyr Lys Gly Gln Lys Leu Lys Gly Ile Ser Phe Glu Asn Ser Asn
65                  70                  75                  80

Gly Glu Trp Ala Tyr Lys Val Thr Gln Gln Lys Ser Gly Glu Glu Ser
                85                  90                  95

Glu Val Leu Val Asp Asp Lys Asn Lys Lys Val Ile Asn Lys Lys Thr
            100                 105                 110

Glu Lys Glu Asp Thr Val Asn Glu Asn Asp Asn Phe Lys Tyr Ser Asp
        115                 120                 125

Ala Ile Asp Tyr Lys Lys Ala Ile Lys Glu Gly Gln Lys Glu Phe Asp
130                 135                 140

Gly Asp Ile Lys Glu Trp Ser Leu Glu Lys Asp Gly Lys Leu Val
145                 150                 155                 160

Tyr Asn Ile Asp Leu Lys Lys Gly Asn Lys Lys Gln Glu Val Thr Val
                165                 170                 175

Asp Ala Lys Asn Gly Lys Val Leu Lys Ser Glu Gln Asp Gln
            180                 185                 190

<210> SEQ ID NO 13
<211> LENGTH: 1009
<212> TYPE: PRT
<213> ORGANISM: Staphylococcus aureus

<400> SEQUENCE: 13

Met Lys Lys Lys Asn Trp Ile Tyr Ala Leu Ile Val Thr Leu Ile Ile
1               5                   10                  15

Ile Ile Ala Ile Val Ser Met Ile Phe Phe Val Gln Thr Lys Tyr Gly
            20                  25                  30

Asp Gln Ser Glu Lys Gly Ser Gln Ser Val Ser Asn Lys Asn Asn Lys
        35                  40                  45

Ile His Ile Ala Ile Val Asn Glu Asp Gln Pro Thr Thr Tyr Asn Gly
50                  55                  60

Lys Lys Val Glu Leu Gly Gln Ala Phe Ile Lys Arg Leu Ala Asn Glu
65                  70                  75                  80

Lys Asn Tyr Lys Phe Glu Thr Val Thr Arg Asn Val Ala Glu Ser Gly
                85                  90                  95

Leu Lys Asn Gly Gly Tyr Gln Val Met Ile Val Ile Pro Glu Asn Phe
            100                 105                 110

Ser Lys Leu Ala Met Gln Leu Asp Ala Lys Thr Pro Ser Lys Ile Ser
        115                 120                 125

Leu Gln Tyr Lys Thr Ala Val Gly Gln Lys Glu Glu Val Ala Lys Asn

-continued

```
            130                 135                 140
Thr Glu Lys Val Val Ser Asn Val Leu Asn Asp Phe Asn Lys Asn Leu
145                 150                 155                 160

Val Glu Ile Tyr Leu Thr Ser Ile Ile Asp Asn Leu His Asn Ala Gln
                165                 170                 175

Lys Asn Val Gly Ala Ile Met Thr Arg Glu His Gly Val Asn Ser Lys
            180                 185                 190

Phe Ser Asn Tyr Leu Leu Asn Pro Ile Asn Asp Phe Pro Glu Leu Phe
        195                 200                 205

Thr Asp Thr Leu Val Asn Ser Ile Ser Ala Asn Lys Asp Ile Thr Lys
    210                 215                 220

Trp Phe Gln Thr Tyr Asn Lys Ser Leu Leu Ser Ala Asn Ser Asp Thr
225                 230                 235                 240

Phe Arg Val Asn Thr Asp Tyr Asn Val Ser Thr Leu Ile Glu Lys Gln
                245                 250                 255

Asn Ser Leu Phe Asp Glu His Asn Thr Ala Met Asp Lys Met Leu Gln
            260                 265                 270

Asp Tyr Lys Ser Gln Lys Asp Ser Val Glu Leu Asp Asn Tyr Ile Asn
        275                 280                 285

Ala Leu Lys Gln Met Asp Ser Gln Ile Asp Gln Gln Ser Ser Met Gln
    290                 295                 300

Asp Thr Gly Lys Glu Glu Tyr Lys Gln Thr Val Lys Glu Asn Leu Asp
305                 310                 315                 320

Lys Leu Arg Glu Ile Ile Gln Ser Gln Glu Ser Pro Phe Ser Lys Gly
                325                 330                 335

Met Ile Glu Asp Tyr Arg Lys Gln Leu Thr Glu Ser Leu Gln Asp Glu
            340                 345                 350

Leu Ala Asn Asn Lys Asp Leu Gln Asp Ala Leu Asn Ser Ile Lys Met
        355                 360                 365

Asn Asn Ala Gln Phe Ala Glu Asn Leu Glu Lys Gln Leu His Asp Asp
    370                 375                 380

Ile Val Lys Glu Pro Asp Ser Asp Thr Thr Phe Ile Tyr Asn Met Ser
385                 390                 395                 400

Lys Gln Asp Phe Ile Ala Ala Gly Leu Asn Glu Asp Glu Ala Asn Lys
                405                 410                 415

Tyr Glu Ala Ile Val Lys Glu Ala Lys Arg Tyr Lys Asn Glu Tyr Asn
            420                 425                 430

Leu Lys Lys Pro Leu Ala Glu His Ile Asn Leu Thr Asp Tyr Asp Asn
        435                 440                 445

Gln Val Ala Gln Asp Thr Ser Ser Leu Ile Asn Asp Gly Val Lys Val
    450                 455                 460

Gln Arg Thr Glu Thr Ile Lys Ser Asn Asp Ile Asn Gln Leu Thr Val
465                 470                 475                 480

Ala Thr Asp Pro His Phe Asn Phe Glu Gly Asp Ile Lys Ile Asn Gly
                485                 490                 495

Lys Lys Tyr Asp Ile Lys Asp Gln Ser Val Gln Leu Asp Thr Ser Asn
            500                 505                 510

Lys Glu Tyr Lys Val Glu Val Asn Gly Val Ala Lys Leu Lys Lys Asp
        515                 520                 525

Ala Glu Lys Asp Phe Leu Lys Asp Lys Thr Met His Leu Gln Leu Leu
    530                 535                 540

Phe Gly Gln Ala Asn Arg Gln Asp Glu Pro Asn Asp Lys Lys Ala Thr
545                 550                 555                 560
```

```
Ser Val Val Asp Val Thr Leu Asn His Asn Leu Asp Gly Arg Leu Ser
            565                 570                 575

Lys Asp Ala Leu Ser Gln Gln Leu Ser Ala Leu Ser Arg Phe Asp Ala
            580                 585                 590

His Tyr Lys Met Tyr Thr Asp Thr Lys Gly Arg Glu Asp Lys Pro Phe
            595                 600                 605

Asp Asn Lys Arg Leu Ile Asp Met Met Val Asp Gln Val Ile Asn Asp
            610                 615                 620

Met Glu Ser Phe Lys Asp Asp Lys Val Ala Val Leu His Gln Ile Asp
625                 630                 635                 640

Ser Met Glu Glu Asn Ser Asp Lys Leu Ile Asp Ile Leu Asn Asn
                    645                 650                 655

Lys Lys Asn Thr Thr Lys Asn Lys Glu Asp Ile Ser Lys Leu Ile Asp
                    660                 665                 670

Gln Leu Glu Asn Val Lys Lys Thr Phe Ala Glu Pro Gln Glu Pro
                    675                 680                 685

Lys Ile Asp Lys Gly Lys Asn Asp Glu Phe Asn Thr Met Ser Ser Asn
            690                 695                 700

Leu Asp Lys Glu Ile Ser Arg Ile Ser Glu Lys Ser Thr Gln Leu Leu
705                 710                 715                 720

Ser Asp Thr Gln Glu Ser Lys Thr Ile Ala Asp Ser Val Ser Gly Gln
                    725                 730                 735

Leu Asn Gln Leu Asp Asn Asn Val Asn Lys Leu His Ala Thr Gly Arg
                    740                 745                 750

Ala Leu Gly Val Arg Ala Asn Asp Leu Asn Arg Gln Met Ala Lys Asn
            755                 760                 765

Asp Lys Asp Asn Glu Leu Phe Ala Lys Glu Phe Lys Lys Val Leu Gln
770                 775                 780

Asn Ser Lys Asp Gly Asp Arg Gln Asn Gln Ala Leu Lys Ala Phe Met
785                 790                 795                 800

Ser Asn Pro Val Gln Lys Lys Asn Leu Glu Asn Val Leu Ala Asn Asn
            805                 810                 815

Gly Asn Thr Asp Val Ile Ser Pro Thr Leu Phe Val Leu Leu Met Tyr
            820                 825                 830

Leu Leu Ser Met Ile Thr Ala Tyr Ile Phe Tyr Ser Tyr Glu Arg Ala
            835                 840                 845

Lys Gly Gln Met Asn Phe Ile Lys Asp Asp Tyr Ser Ser Lys Asn Asn
850                 855                 860

Leu Trp Asn Asn Ala Ile Thr Ser Gly Val Ile Gly Ala Thr Gly Leu
865                 870                 875                 880

Val Glu Gly Leu Ile Val Gly Leu Ile Ala Met Asn Lys Phe His Val
            885                 890                 895

Leu Ala Gly Tyr Arg Ala Lys Phe Ile Leu Met Val Ile Leu Thr Met
            900                 905                 910

Met Val Phe Val Leu Ile Asn Thr Tyr Leu Leu Arg Gln Val Lys Ser
            915                 920                 925

Ile Gly Met Phe Leu Met Ile Ala Ala Leu Gly Leu Tyr Phe Val Ala
            930                 935                 940

Met Asn Asn Leu Lys Ala Ala Gly Gln Gly Val Thr Asn Lys Ile Ser
945                 950                 955                 960

Pro Leu Ser Tyr Ile Asp Asn Met Phe Phe Asn Tyr Leu Asn Ala Glu
            965                 970                 975
```

His Pro Ile Gly Leu Ala Leu Val Ile Leu Thr Val Leu Val Ile Ile
            980                 985                 990

Gly Phe Val Leu Asn Met Phe Ile Lys His Phe Lys Lys Glu Arg Leu
        995                 1000                1005

Ile

<210> SEQ ID NO 14
<211> LENGTH: 396
<212> TYPE: PRT
<213> ORGANISM: Staphylococcus aureus

<400> SEQUENCE: 14

Met Thr Gln Gln Gln Asn Asn Lys Arg Thr Leu Lys Asn Lys His Thr
1               5                   10                  15

Tyr Gln Asn Glu Pro Leu Pro Asn Arg Lys Asp Phe Val Val Ser Phe
            20                  25                  30

Ile Thr Gly Ala Leu Val Gly Ser Ala Leu Gly Leu Tyr Phe Lys Asn
        35                  40                  45

Lys Val Tyr Gln Lys Ala Asp Asp Leu Lys Val Lys Glu Gln Glu Leu
    50                  55                  60

Ser Gln Lys Phe Glu Glu Arg Lys Thr Gln Leu Glu Glu Thr Val Ala
65                  70                  75                  80

Phe Thr Lys Glu Arg Val Glu Gly Phe Leu Asn Lys Ser Lys Asn Glu
                85                  90                  95

Gln Ala Ala Leu Lys Ala Gln Gln Ala Ala Ile Lys Glu Glu Ala Ser
            100                 105                 110

Ala Asn Asn Leu Ser Asp Thr Ser Gln Glu Ala Gln Ile Gln Glu
        115                 120                 125

Ala Lys Arg Glu Ala Gln Thr Glu Thr Asp Lys Ser Ala Ala Val Ser
    130                 135                 140

Asn Glu Glu Ser Lys Ala Ser Ala Leu Lys Ala Gln Gln Ala Ala Ile
145                 150                 155                 160

Lys Glu Glu Ala Ser Ala Asn Asn Leu Ser Asp Thr Ser Gln Glu Ala
                165                 170                 175

Gln Ala Ile Gln Glu Val Lys Lys Glu Ala Gln Ala Glu Thr Asp Lys
            180                 185                 190

Ser Ala Asp Val Ser Asn Glu Glu Ser Lys Ala Ser Thr Leu Asn Val
        195                 200                 205

Ser Lys Glu Glu Ser Gln Ala Glu Arg Leu Ala Asn Ala Ala Lys Gln
    210                 215                 220

Lys Gln Ala Lys Leu Thr Pro Gly Ser Lys Glu Ser Gln Leu Thr Glu
225                 230                 235                 240

Ala Leu Phe Ala Glu Lys Pro Val Ala Lys Asn Asp Leu Lys Glu Ile
                245                 250                 255

Pro Leu Leu Val Thr Lys Lys Asn Asp Val Ser Glu Thr Val Asn Thr
            260                 265                 270

Asp Asn Lys Asp Thr Val Lys Gln Lys Glu Ala Lys Phe Glu Asn Gly
        275                 280                 285

Val Ile Thr Arg Lys Ala Asp Glu Lys Thr Pro Asn Asn Thr Ala Val
    290                 295                 300

Asp Lys Lys Ser Gly Lys Gln Ser Lys Thr Thr Pro Ser Asn Lys
305                 310                 315                 320

Arg Asn Ala Ser Lys Ala Ser Thr Asn Lys Thr Ser Gly Gln Lys Lys
                325                 330                 335

```
Gln His Asn Lys Lys Ala Ser Gln Gly Ala Lys Lys Gln Ser Ser Ser
            340                 345                 350

Ser Asn Ser Thr Thr Lys Thr Asn Gln Lys Asn Ser Lys Ala Thr Asn
            355                 360                 365

Ala Lys Ser Ser Asn Ala Ser Lys Lys Ser Asn Ala Lys Val Glu Lys
            370                 375                 380

Ala Lys Ser Lys Ile Glu Lys Arg Thr Phe Asn Asp
385                 390                 395

<210> SEQ ID NO 15
<211> LENGTH: 769
<212> TYPE: PRT
<213> ORGANISM: Staphylococcus aureus

<400> SEQUENCE: 15

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
            35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Gly Ser Lys Ser Ala Tyr
                85                  90                  95

Asn Lys Asp His Tyr Leu Thr Asp Asp Val Ser Lys Lys Gln Asn Ser
            100                 105                 110

Leu Asp Ser Val Asp Gln Asp Thr Glu Lys Ser Lys Tyr Tyr Glu Gln
            115                 120                 125

Asn Thr Glu Ala Thr Leu Ser Thr Asn Ser Thr Asp Lys Val Glu Ser
            130                 135                 140

Thr Asp Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Phe Glu Ser Ser Arg Thr Asp Ser Asp Ser Ser Met Gln Thr
            180                 185                 190

Glu Lys Ile Lys Lys Asp Ser Ser Asp Gly Asn Lys Ser Ser Asn Leu
            195                 200                 205

Lys Ser Glu Val Ile Ser Asp Lys Ser Asn Ser Val Pro Ile Leu Ser
            210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Thr Pro Ser Ile Ser Asp Lys Asp Tyr Val
            275                 280                 285

Met Arg Glu Asp His Ile Val Asp Asp Asn Pro Asp Asn Asp Ile Asn
            290                 295                 300

Thr Pro Ser Leu Ser Lys Ile Asp Asp Arg Lys Leu Asp Glu Lys
305                 310                 315                 320
```

```
Ile His Val Glu Asp Lys His Lys Gln Asn Ala Asp Ser Ser Glu Thr
                325                 330                 335

Val Gly Tyr Gln Ser Gln Ser Ser Ala Ser His Arg Ser Thr Glu Lys
            340                 345                 350

Arg Asn Met Ala Ile Asn Asp His Asp Lys Leu Asn Gly Gln Lys Pro
                355                 360                 365

Asn Thr Lys Thr Ser Ala Asn Asn Gln Lys Lys Ala Thr Ser Lys
        370                 375                 380

Leu Asn Lys Gly Arg Ala Thr Asn Asn Tyr Ser Ala Ile Leu Lys
385                 390                 395                 400

Lys Phe Trp Met Met Tyr Trp Pro Lys Leu Val Ile Leu Met Gly Ile
                    405                 410                 415

Ile Ile Leu Ile Val Ile Leu Asn Ala Ile Phe Asn Asn Val Asn Lys
                420                 425                 430

Asn Asp Arg Met Asn Asp Asn Asp Ala Asp Ala Gln Lys Tyr Thr
            435                 440                 445

Thr Thr Met Lys Asn Ala Asn Asn Ala Val Lys Ser Val Val Thr Val
        450                 455                 460

Glu Asn Glu Thr Ser Lys Asp Ser Ser Leu Pro Lys Asp Lys Ala Ser
465                 470                 475                 480

Gln Asp Glu Val Gly Ser Gly Val Val Tyr Lys Lys Ser Gly Asp Thr
                485                 490                 495

Leu Tyr Ile Val Thr Asn Ala His Val Val Gly Asp Lys Glu Asn Gln
                500                 505                 510

Lys Ile Thr Phe Ser Asn Asn Lys Ser Val Val Gly Lys Val Leu Gly
                515                 520                 525

Lys Asp Lys Trp Ser Asp Leu Ala Val Val Lys Ala Thr Ser Ser Asp
530                 535                 540

Ser Ser Val Lys Glu Ile Ala Ile Gly Asp Ser Asn Asn Leu Val Leu
545                 550                 555                 560

Gly Glu Pro Ile Leu Val Val Gly Asn Pro Leu Gly Val Asp Phe Lys
                565                 570                 575

Gly Thr Val Thr Glu Gly Ile Ile Ser Gly Leu Asn Arg Asn Val Pro
                580                 585                 590

Ile Asp Phe Asp Lys Asp Asn Lys Tyr Asp Met Leu Met Lys Ala Phe
                595                 600                 605

Gln Ile Asp Ala Ser Val Asn Pro Gly Asn Ser Gly Gly Ala Val Val
            610                 615                 620

Asn Arg Glu Gly Lys Leu Ile Gly Val Val Ala Ala Lys Ile Ser Met
625                 630                 635                 640

Pro Asn Val Glu Asn Met Ser Phe Ala Ile Pro Val Asn Glu Val Gln
                645                 650                 655

Lys Ile Val Lys Glu Leu Glu Thr Lys Gly Lys Ile Asp Tyr Pro Asp
                660                 665                 670

Val Gly Val Lys Met Lys Asn Ile Ala Ser Leu Asn Ser Phe Glu Arg
            675                 680                 685

Gln Ala Val Lys Leu Leu Gly Lys Val Lys Asn Gly Val Val Asp
        690                 695                 700

Gln Val Asp Asn Asn Gly Leu Ala Asp Gln Ser Gly Leu Lys Lys Gly
705                 710                 715                 720

Asp Val Ile Thr Glu Leu Asp Gly Lys Leu Leu Glu Asp Asp Leu Arg
                725                 730                 735
```

Phe Arg Gln Ile Ile Phe Ser His Lys Asp Asp Leu Lys Ser Ile Thr
            740                 745                 750

Ala Lys Ile Tyr Arg Asp Gly Lys Glu Lys Glu Ile Asn Ile Lys Leu
        755                 760                 765

Lys

<210> SEQ ID NO 16
<211> LENGTH: 208
<212> TYPE: PRT
<213> ORGANISM: Staphylococcus aureus

<400> SEQUENCE: 16

Met Lys Phe Lys Ala Ile Val Ala Ile Thr Leu Ser Leu Ser Leu Leu
1               5                   10                  15

Thr Ala Cys Gly Ala Asn Gln His Lys Glu Asn Ser Ser Lys Ser Asn
            20                  25                  30

Asp Thr Asn Lys Lys Thr Gln Gln Thr Asp Asn Thr Thr Gln Ser Asn
        35                  40                  45

Thr Glu Lys Gln Met Thr Pro Gln Glu Ala Glu Asp Ile Val Arg Asn
50                  55                  60

Asp Tyr Lys Ala Arg Gly Ala Asn Glu Asn Gln Thr Leu Asn Tyr Lys
65                  70                  75                  80

Thr Asn Leu Glu Arg Ser Asn Glu His Glu Tyr Tyr Val Glu His Leu
            85                  90                  95

Val Arg Asp Ala Val Gly Thr Pro Leu Lys Arg Cys Ala Ile Val Asn
            100                 105                 110

Arg His Asn Gly Thr Ile Ile Asn Ile Phe Asp Asp Met Ser Glu Lys
        115                 120                 125

Asp Lys Glu Glu Phe Glu Ala Phe Lys Lys Arg Ser Pro Lys Tyr Asn
130                 135                 140

Pro Gly Met Asn Asp Gln Ala Glu Met Asp Asn Glu Ser Glu Asp Ile
145                 150                 155                 160

Gln His His Asp Ile Asp Asn Asn Lys Ala Ile Gln Asn Asp Leu Pro
            165                 170                 175

Asp Gln Lys Val Asp Asp Lys Asn Asp Lys Asn Ala Val Asn Lys Glu
        180                 185                 190

Glu Lys His Asp Asn Arg Glu Asn Asn Ser Ala Glu Thr Lys Val Lys
        195                 200                 205

<210> SEQ ID NO 17
<211> LENGTH: 227
<212> TYPE: PRT
<213> ORGANISM: Staphylococcus aureus

<400> SEQUENCE: 17

Met Asp Lys Lys Lys Val Ile Lys Phe Met Ile Asn Val Leu Pro Ile
1               5                   10                  15

Val Leu Val Pro Leu Ile Val Glu Arg Lys Arg Ile Lys Gln His Pro
            20                  25                  30

Asp Val Gln Lys Val Thr Asp Ala Thr Ser Lys Val Ala Ser Lys Thr
        35                  40                  45

Ser Ala Ala Ile Ser Asn Thr Ala Ser Asp Val Lys Glu Tyr Val Gly
50                  55                  60

Asp Lys Lys Gln Asp Phe Glu Asn Lys Arg Glu Leu Lys Lys Phe Ala
65                  70                  75                  80

Arg Glu His Asp Pro Ala Tyr Ile Glu Lys Lys Gly Glu Lys Leu Ala

```
                        85                  90                  95
Lys Gln Asn Arg Lys Asp Ala Asp Lys Met Asn Lys Ile Leu Gln Lys
                100                 105                 110

Asn Ile Glu Lys Arg His Lys Glu Glu Gln Lys Ala Arg Glu Lys Asn
                115                 120                 125

Glu Ile Gln Arg Ile Lys Asp Met Lys Lys Ser Gln Lys Tyr Glu Val
                130                 135                 140

Lys Ala Gly Leu Thr Pro Asn Lys Leu Asp Glu Lys Thr Glu Lys Lys
145                 150                 155                 160

Gly Asp Lys Leu Ala Glu Lys Asn Arg Lys Glu Ile Ala Lys Met Asn
                165                 170                 175

Lys Lys Leu Gln Lys Asn Ile Glu Lys Arg His Lys Glu Glu Gln Lys
                180                 185                 190

Arg Gln Gln Glu Ala Asp Lys Ala Arg Ile Lys Ser Phe Lys Lys Tyr
                195                 200                 205

Lys Asp Tyr Val Ala Lys Ser Ala Ser Gln Gln Asn Lys Glu Asn Asn
                210                 215                 220

Thr Glu Ala
225

<210> SEQ ID NO 18
<211> LENGTH: 404
<212> TYPE: PRT
<213> ORGANISM: Staphylococcus aureus

<400> SEQUENCE: 18

Met Ser Tyr His Trp Phe Lys Lys Met Leu Leu Ser Thr Ser Met Leu
1               5                   10                  15

Ile Leu Ser Ser Ser Ser Leu Gly Leu Ala Thr His Thr Val Glu
                20                  25                  30

Ala Lys Asp Asn Leu Asn Gly Glu Lys Pro Thr Thr Asn Leu Asn His
                35                  40                  45

Asn Val Thr Ser Pro Ser Val Asn Ser Glu Met Asn Asn Glu Thr
        50                  55                  60

Gly Thr Pro His Glu Ser Asn Gln Ala Gly Asn Glu Gly Thr Gly Ser
65                  70                  75                  80

Asn Ser Arg Asp Ala Asn Pro Asp Ser Asn Val Lys Pro Asp Ser
                85                  90                  95

Asn Asn Gln Asn Pro Ser Pro Asp Ser Lys Pro Asp Pro Asn Asn Pro
                100                 105                 110

Asn Pro Gly Pro Asn Pro Lys Pro Asp Pro Asp Lys Pro Lys Pro Asn
                115                 120                 125

Pro Glu Pro Lys Pro Asp Pro Asp Lys Pro Lys Pro Asn Pro Asp Pro
                130                 135                 140

Lys Pro Asp Pro Asp Lys Pro Lys Pro Asn Asp Pro Lys Pro Asp
145                 150                 155                 160

Pro Asn Pro Asn Pro Asn Pro Lys Pro Asp Pro Asn Lys Pro Asn Pro
                165                 170                 175

Asn Pro Ser Pro Asn Pro Asn Gln Pro Gly Asp Ser Asn Gln Ser Gly
                180                 185                 190

Gly Ser Lys Asn Gly Gly Thr Trp Asn Pro Asn Ala Ser Asp Gly Ser
                195                 200                 205

Asn Gln Gly Gln Trp Gln Pro Asn Gly Asn Gln Gly Asn Ser Gln Asn
                210                 215                 220
```

```
Pro Thr Gly Asn Asp Phe Val Ser Gln Arg Phe Leu Ala Leu Ala Asn
225                 230                 235                 240

Gly Ala Tyr Lys Tyr Asn Pro Tyr Ile Leu Asn Gln Ile Asn Gln Leu
            245                 250                 255

Gly Lys Glu Tyr Gly Glu Val Thr Asp Glu Asp Ile Tyr Asn Ile Ile
        260                 265                 270

Arg Lys Gln Asn Phe Ser Gly Asn Ala Tyr Leu Asn Gly Leu Gln Gln
    275                 280                 285

Gln Ser Asn Tyr Phe Arg Phe Gln Tyr Phe Asn Pro Leu Lys Ser Glu
290                 295                 300

Arg Tyr Tyr Arg Asn Leu Asp Glu Gln Val Leu Ala Leu Ile Thr Gly
305                 310                 315                 320

Glu Ile Gly Ser Met Pro Asp Leu Lys Lys Pro Glu Asp Lys Pro Asp
                325                 330                 335

Ser Lys Gln Arg Ser Phe Glu Pro His Glu Lys Asp Asp Phe Thr Val
            340                 345                 350

Val Lys Lys Gln Glu Asp Asn Lys Lys Ser Ala Ser Thr Ala Tyr Ser
        355                 360                 365

Lys Ser Trp Leu Ala Ile Val Cys Ser Met Met Val Val Phe Ser Ile
370                 375                 380

Met Leu Phe Leu Phe Val Lys Arg Asn Lys Lys Asn Lys Asn Glu
385                 390                 395                 400

Ser Gln Arg Arg

<210> SEQ ID NO 19
<211> LENGTH: 231
<212> TYPE: PRT
<213> ORGANISM: Staphylococcus aureus

<400> SEQUENCE: 19

Met Lys Lys Thr Leu Leu Ala Ser Ser Leu Ala Val Gly Leu Gly Ile
1               5                   10                  15

Val Ala Gly Asn Ala Gly His Glu Ala Gln Ala Ser Glu Ala Asp Leu
            20                  25                  30

Asn Lys Ala Ser Leu Ala Gln Met Ala Gln Ser Asn Asp Gln Thr Leu
        35                  40                  45

Asn Gln Lys Pro Ile Glu Ala Gly Ala Tyr Asn Tyr Thr Phe Asp Tyr
    50                  55                  60

Glu Gly Phe Thr Tyr His Phe Glu Ser Asp Gly Thr His Phe Ala Trp
65                  70                  75                  80

Asn Tyr His Ala Thr Gly Ala Asn Gly Ala Asp Met Ser Ala Gln Ala
                85                  90                  95

Pro Ala Thr Asn Asn Val Ala Pro Ser Ala Asp Gln Ser Asn Gln Val
            100                 105                 110

Gln Ser Gln Glu Val Glu Ala Pro Gln Asn Ala Gln Thr Gln Gln Pro
        115                 120                 125

Gln Ala Ser Thr Ser Asn Asn Ser Gln Val Thr Ala Thr Pro Thr Glu
    130                 135                 140

Ser Lys Ala Ser Glu Gly Ser Ser Val Asn Val Asn Asp His Leu Lys
145                 150                 155                 160

Gln Ile Ala Gln Arg Glu Ser Gly Gly Asn Ile His Ala Val Asn Pro
                165                 170                 175

Thr Ser Gly Ala Ala Gly Lys Tyr Gln Phe Leu Gln Ser Thr Trp Asp
            180                 185                 190
```

Ser Val Ala Pro Ala Lys Tyr Lys Gly Val Ser Pro Ala Asn Ala Pro
    195                 200                 205

Glu Ser Val Gln Asp Ala Ala Val Lys Leu Tyr Asn Thr Gly Gly
    210                 215                 220

Ala Gly His Trp Val Thr Ala
225                 230

<210> SEQ ID NO 20
<211> LENGTH: 465
<212> TYPE: DNA
<213> ORGANISM: Staphylococcus aureus

<400> SEQUENCE: 20
atgaaaagat tgttaggttt attattagtg agcacgttag tgttaagtgc atgtggaaat      60
gatgagaatc aggaagaatc taaaaaagaa gttaaatcaa agaaaagaa aattgagaag     120 gaaaaggaaa ataaatcgaa aaaagataag gaaaagaag ttgcaacaca acaacaacca     180
gacaatcaaa ccgttgaaca accccaatca caagagcaat cggttcaaca accgcaacaa     240
cagataccac aaaatagtgt tcctcagcaa atgtccaag ttcaacaaaa caaaaagcaa     300
aaagttgatt taataatat gcctcccact gattttcta cagagggtat gtctgagcag     360
gctcaaaaac aaattgaaga gctttcaatg caaaaagact atcatggtct gtcacaaaga     420
gaatacaatg atagagtttc tgaaattata ataatgata attga                     465

<210> SEQ ID NO 21
<211> LENGTH: 555
<212> TYPE: DNA
<213> ORGANISM: Staphylococcus aureus

<400> SEQUENCE: 21
atgttaaaag gatgcggcgg ttgccttatt tcttttatta tattaattat cttattatca      60
gcctgttcaa tgatgtttag taataatgac aattccacta gtaatcaatc atcaaaaacg     120
caattaactc aaaaagacga agataaaagt gaaaatatgc ctgaagaaaa atcagaatca     180
gaaacagata aggatttaca tcaaccgaa gaagtacccg caaatgaaaa tactgaaaat     240
aatcaacatg aaattgatga ataacaaca acagatcaat cagatgatga attaacaca     300 ccaaacgttg cagaagaaga atcacaagat gacttgaaag atgatttaaa agaaaagcaa     360
caaccaagtg accatcatca atccacgcaa cctaagactt caccatcaac tgaaacaaac     420
aagcaacaat catttgctaa ttgtaagcaa cttagacaag tatatccgaa tggtgtcact     480
gccgatcatc cagcatatcg accacattta gatagagata agataaaacg tgcatgtgaa     540
cctgataaat attaa                                                      555

<210> SEQ ID NO 22
<211> LENGTH: 390
<212> TYPE: DNA
<213> ORGANISM: Staphylococcus aureus

<400> SEQUENCE: 22
atgaagaaat taatcatcag cattatggcg atcatgctat ttttaacagg ttgtggtaaa      60
agccaagaga aagccactct ggaaaaggat atcgataatt tacaaaaaga aaataaagaa     120
ttaaaagata aaaagaaaa gcttcaacaa gaaaaagaaa aattagcaga taagcaaaaa     180
gaccttgaaa aagaagtgaa agattttaaa ccttcaaaag aagataacaa ggacgataaa     240
aaagacgaag acaaaaataa agacaaagat aaagaggcat cacaagataa gcaatcaaaa     300

| | |
|---|---|
| gatcaaacta agtcatcgga taaagataat cacaaaaagc ctacatcaac agataaagat | 360 |
| caaaaagcta atgacaaaca ccaatcataa | 390 |

<210> SEQ ID NO 23
<211> LENGTH: 2982
<212> TYPE: DNA
<213> ORGANISM: Staphylococcus aureus

<400> SEQUENCE: 23

| | |
|---|---|
| atgaagaacg catttaaatt atttaaaatg gatctgaaga aagtagctaa gacgccagct | 60 |
| gtgtggatta tcttagcagg cttagctatt ttgccatcgt tctacgcttg gtttaactta | 120 |
| tgggcaatgt gggatccata tggcaacacg ggacacatca aggtcgcagt cgttaatgaa | 180 |
| gataaaggcg acacaatcag agggaaaaaa gttaatgtcg gtaatacgat ggttaacaca | 240 |
| ctcaagaaaa ataaaagttt tgattggcag tttgtaagta gagagaaagc tgatcatgag | 300 |
| ataaaaatgg gtaaatattt tgcaggtatt tacatcccat ctaagtttac acatgaaatt | 360 |
| accgggacac tacgtaagca gcctcaaaaa gcagatgtag aatttaaggt gaatcagaag | 420 |
| attaacgctg ttgcgtctaa gctaacagat actggttcgt cagttgtcgt tgaaaaagcg | 480 |
| aatgaacaat ttaataaaac agtaactcga gcattattag aagaagctaa caagcaggt | 540 |
| ttaactattg aagaaaatgt gccgacaatt aataagataa aaaatgcggt atattcggca | 600 |
| gataaagctt tacctaagat taatgacttt gcgaataaaa ttgtatattt gaataaccac | 660 |
| caagcggatt tagataaata tgcgaatgat tttagaaaac taggaaatta taaaggtgat | 720 |
| attttagatg ctcagaaaaa attaaacgaa gtcaatggtg ctattccgca acttaatgaa | 780 |
| aaggctaagt tgatattagc tttaaataat tatatgccga aaattgaaaa agcgttaaat | 840 |
| tttgcagctg atgacgtgcc agcgcagttc cctaaaatta tcaaggact taacattgcg | 900 |
| agtcaaggta ttgatcaagc taatggacag ttaaatgatg ccaaaggctt cgtcacacaa | 960 |
| gttagaagta gagtcggtga ttatcaagaa gcaattcgac gcgcgcaaga tttgaatcga | 1020 |
| agaaaccagc aacagattcc tcaaaatagc gcggcgaaca acgaaacatc aaatagtgca | 1080 |
| cctgcagctg gtaatggtgt aacatcaacg ccaccaagtg caccaaatgg caatactaca | 1140 |
| ccaaataata atgttacgca aaataccgca ccaaatagta ataatgcacc tgtatcgact | 1200 |
| acaccacaaa gtacaagcgg gaaaaaagat ggtcaaagtt ttgcagatat aacaacaaca | 1260 |
| caagtcagca cagctaacga gaacacacaa atattacag ataaagatgt taaatcaatg | 1320 |
| gaagcggcat taacgggctc tttattatca ttatcaaata atttagatac ccaagcgaaa | 1380 |
| gccgcacaaa aagatagtca ggcattacgt aatatttcgt atggcatttt agcatcggac | 1440 |
| aagccatctg atttagaga gtctttagat aatgttaagt ccggtttaga atacacaact | 1500 |
| caatataatc aacaatttat cgatacatta aaagagattg agaagaatga aatgttgat | 1560 |
| ttatcaaaag aaattgataa ggtaaagaca gctaataatc gaattaatga atcattaagg | 1620 |
| ttagttaatc aattaagtaa tgcattaaag aatggtagtt caggaactgc tgaagctact | 1680 |
| aaattactag atcaactgtc aaaactagat tcatcattat catcatttag agattatgtt | 1740 |
| aaaaaagatc ttaacagctc tttagtatca atatcacaac gtattatgga tgaattgaac | 1800 |
| aaagggcaaa cggcattgtc taatgttcag tctaagctaa atacaattga tcaagtcatc | 1860 |
| aacagtggtc aatctatttt aaaaaatggt aaaacacgta tcgatcgttt acaaacagta | 1920 |
| ttaccaagta ttgaacaaca atacattagt gctattaaaa atgctcaagc aaacttcccg | 1980 |
| aaagtgaaaa gtgatgtagc gaaagcagct aactttgtac gtaacgattt accacagttg | 2040 |

```
gagcaacgtt taaccaatgc gactgcaagt gtgaataaaa atttaccaac gttattaaat    2100
ggttatgatc aagcggtagg attactaaat aaaaatcagc cacaagcgaa aaaggcttta    2160
tcagatttag ctgattttgc acaaaataaa ttgccagatg ttgaaaaaga tctgaaaaaa    2220
gcgaataaga ttttcaagaa gttagacaaa gacgatgcag tcgataaatt aatcgacaca    2280
cttaagaatg atttgaaaaa gcaagcgggt attattgcaa atcctattaa taagaagact    2340
gttgatgttt tcccagttaa ggattatgga tcagggatga caccattcta tactgcatta    2400
tcggtatggg taggcgcact cttaatggta agcctattaa ctgttgataa taaacataag    2460
agcttagagc cagtgttaac gacacgacaa gtattcttag gtaaagcagg attctttata    2520
atgcttggta tgttgcaagc actcattgta tcggttggag atttgttaat cctaaaagca    2580
ggagttgagt cacctgtatt attcgtactt ataacgattt tctgttcgat tattttcaac    2640
tcaatcgtat atacgtgcgt atcattactt ggtaacccag gtaaagccat tgcaatcgta    2700
ttgcttgtat tacaaattgc aggtggtgga ggtacattcc caattcaaac gacaccacaa    2760 ttttttccaaa acatttcgcc atacttacca tttacgtatg caattgattc attacgtgaa    2820
acagtaggcg gtattgttcc ggaaatctta attacaaaat taattatatt aacgttattt    2880
ggcataggat tcttcgttgt aggtttaatt ttaaaacctg taacagatcc attgatgaag    2940
cgcgtatctg aaaagttga ccaaagtaac gttacagaat aa                       2982
```

<210> SEQ ID NO 24
<211> LENGTH: 6201
<212> TYPE: DNA
<213> ORGANISM: Staphylococcus aureus

<400> SEQUENCE: 24

```
atgaatgaaa aagtagaagg catgaccttg gagctgaaat tagaccattt aggtgtccaa      60
gaaggcatga aggtttaaa gcgacaatta ggtgttgtta atagtgaaat gaaagctaat     120
ctgtcagcat ttgataagtc tgaaaaatca atggaaaaat atcaggcgag aattaagggg    180
ttaaatgata ggcttaaagt tcaaaaaaag atgtattctc aagtagaaga tgagcttaaa    240
caagttaacg ctaattacca aaaagctaaa tccagtgtaa aagatgttga gaaagcatat    300
ttaaagttag tagaagccaa taaaaagaa aaattagctc ttgataaatc taaagaagcc    360
ttaaaatcat cgaatacaga acttaaaaaa gctgaaaatc aatataaacg tacaaatcaa    420
cgtaaacaag atgcgtatca aaacttaaa cagttgagag atgcagaaca aaagcttaag    480
aatagtaacc aagctactac tgcacaacta aaaagagcaa gtgacgcagt acagaagcag    540
tccgctaagc ataaagcact tgttgaacaa tataaacaag aaggcaatca agttcaaaaa    600
ctaaaagtgc aaaatgacaa tctttcaaaa tcaaatgata aaattgaaag ttcttacgct    660
aaaactaata ctaaattaaa gcaaacagaa aaagaattta tgatttaaa caatactatt    720 aagaatcata gcgctaatgt cgcaaaagct gaaacagctg ttaataaaga aaagctgct    780 ttaaataatt tggagcgttc aatagataaa gcttcatccg aaatgaagac ttttaacaaa    840
gaacaaatga tagctcaaag tcatttcggt aaacttgcaa gtcaagcgga tgtcatgtca    900
aagaaattta gttctattgg agacaaaatg acttccctgg acgtacaat gacgatgggc    960 gtatctacac caattacttt agggttaggt gcagcattaa aaacaagtgc agactttgaa   1020
ggccaaatgt ctcgagttgg agcgattgcg caagcaagca gtaaagactt gaaaagcatg   1080
tctaatcaag cagttgactt aggagctaaa accagtaaaa gtgctaacga agttgctaaa   1140
```

```
ggtatggaag aattggcagc tttaggcttt aatgccaaac aaacaatgga ggctatgcca    1200
ggtgttatca gtgcagcaga agcaagtggt gcagaaatgg ctacaactgc aactgtaatg    1260
gcttcagcga ttaactcttt cggttttaaaa gcatctgatg caaatcatgt tgctgattta   1320
cttgcgagat cagcaaatga tagtgctgca gatattcagt acatgggaga tgcattgaag    1380
tatgctggta ctcctgcaaa agcattagga gtttcaatag aggacacttc cgcagcaatt    1440
gaagttttat ctaactcagg tttagagggt tctcaagcag gtactgccct aagagcttca    1500
tttatcaggc tagctaatcc aagtaaaaat acagctaagg aaatgaaaaa attaggtatt    1560
catttgtctg atgctaaagg tcaatttgtt ggcatgggtg aattgattag acagttccaa    1620
gataatatga aaggcatgac gagagaacaa aaactagcta cagtggctac aatagttggt    1680
actgaagcag caagtggatt tttagccttg attgaagcgg gaccagataa aattaatagc    1740
tatagtaaat ccttaaagaa ttccaatggc gaaagtaaaa aagcagcaga tttgatgaaa    1800
gataatctca aaggcgctct ggaacaatta ggtggcgctt ttgaatcatt agcaatcgaa    1860
gtcggtaaag atttaacgcc tatgattaga gcaggagcgg aaggtttaac aaaattagtt    1920
gatggattta cacatctccc tggttgggtt agaaaagctt cagtaggatt agcactttt    1980 ggtgcatcta ttggccctgc tgttcttgct ggtggcttat taatacgtgc agttggaagt    2040
gctgctaaag gctatgcatc attaaataga cgcattgctg aaaatacaat actgtctaat    2100
accaattcaa aagcaatgaa atctttaggt cttcaaacct tatttcttgg ttctacaaca    2160
ggaaaaacgt caaaggctt taaggatta gccggagcta tgttgtttaa tttaaaacct    2220
ataaatgttt tgaaaaattc tgcaaagcta gcaattttac cgttcaaact tttgaaaaac    2280
ggtttaggat tagccgcaaa atccttattt gcagtaagtg gaggcgcaag atttgctggt    2340
gtagccttaa agttttttaac aggacctata ggtgctacaa taactgctat tacaattgca    2400
tataagtttt ttaaaaccgc atatgatcgt gtggaatggt tcagaaacgg tattaacggt    2460
ttaggagaaa ctataaagtt ttttggtggc aaaattattg gcggtgctgt taggaagcta    2520
ggagagttta aaattatct tggaagtata ggcaaaagct tcaagaaaa gttttcaaag    2580 gatatgaaag atggttataa atctttgagt gacgatgacc ttctgaaagt aggagtcaac    2640 aagttaaag gatttatgca accatgggc acagcttcta aaaagcatc tgatactgta    2700 aaagtgttgg ggaaaggtgt ttcaaaagaa acagaaaaag cttagaaaa atacgtacac    2760 tattctgaag agaacaacag aatcatggaa aaagtacgtt taaactcggg tcaaataaca    2820
gaagacaaag caaaaaaact tttgaaaatt gaagcggatt tatctaataa cctttatagct   2880 gaaatagaaa aagaaataa aaaggaactc gaaaaaactc aagaacttat tgataagtat    2940
agtgcgttcg atgaacaaga aaagcaaaac attttaacta gaactaaaga aaaaaatgac    3000
ttgcgaatta aaaagagca agaactcaat cagaaaatca agaattgaa agaaaaagct    3060 ttaagtgatg gtcagatttc agaaaatgaa agaaagaaa ttgaaaagct tgaaaatcaa    3120
agacgtgaca tcactgttaa agaattgagt aagactgaaa aagagcaaga gcgtatttta    3180
gtaagaatgc aaagaaacag aaattcttat tcaatagacg aagcgagcaa agcaattaaa    3240
gaagcagaaa agcaagaaa agcaaaaaaa aagaagtgg acaagcaata tgaagatgat    3300
gtcattgcta taaaaaataa cgtcaacctt tctaagtctg aaaagataa attattagct    3360 attgctgatc aaagacataa ggatgaagta agaaaggcaa atctaaaaa agatgctgta    3420 gtagacgttg ttaaaaagca aaataagat attgataaag agatggattt atccagtggt    3480
cgtgtatata aaaatactga aaaatggtgg aatggcctta aagttggtg gtctaacttc    3540
```

```
agagaagacc aaaagaagaa aagtgataag tacgctaaag aacaagaaga aacagctcgt    3600
agaaacagag aaaatataaa gaaatggttt ggaaatgctt gggacggcgt aaaaagtaaa    3660
actggcgaag cctttagtaa aatgggcaga aatgctaatc attttggcgg cgaaatgaaa    3720
aaaatgtgga gtggaatcaa aggaattcca agcaaattaa gttcaggttg gagctcagcc    3780
aaaagttctg taggatatca cactaaggct atagctaata gtactggtaa atggtttgga    3840
aaagcttggc aatctgttaa atcgactaca ggaagtattt acaatcaaac taagcaaaag    3900
tattcagatg cctcagataa agcttgggcg cattcaaaat ctatttggaa agggacatca    3960
aaatggttta gcaatgcata taaaagtgca aagggctggc taacggatat ggctaataaa    4020
tcgcgctcga aatgggataa tatttctagt acagcatggt cgaatgcaaa atccgtttgg    4080
aaaggaacat cgaaatggtt tagtaactca tacaaatctt taaaaggttg gactggagat    4140
atgtattcaa gagcccacga tcgttttgat gcaatttcaa gttcggcatg gtctaacgct    4200
aaatcagtat ttaatggttt tagaaaaatgg ctatcaagaa catatgaatg gattagagat    4260
attggtaaag acatgggaag agctgcggct gatttaggta aaaatgttgc taataaagct    4320
attggcggtt tgaatagcat gattggcggt attaataaaa tatctaaagc cattactgat    4380
aaaaatctca tcaagccaat acctacattg tctactggta ctttagcagg aaagggtgta    4440
gctaccgata attcgggagc attaacgcaa ccgacatttg ctgtattaaa tgatagaggt    4500
tctggaaacg ccccaggcgg tggagttcaa gaagtaattc acagggctga cggaacattc    4560
catgcacccc aaggacgaga tgtggttgtt ccactaggag ttggagatag tgtaataaat    4620
gccaatgaca ctctgaagtt acagcggatg ggtgttttgc caaaattcca tggtggtacg    4680
aaaaagaaaa aatggatgga acaagttact gaaaatcttg gtaaaaaagc agggacttc    4740 ggttctaaag ctaaaaacac agctcataat atcaaaaaag gtgcagaaga aatggttgaa    4800
gccgcaggcg ataaaatcaa agatggtgca tcttggttag cgataaaaat cggcgatgtg    4860
tgggattatg tacaacatcc agggaaacta gtaaataaag taatgtcagg tttaaatatt    4920
aattttggag gcggagctaa cgctacagta aaaattgcta aaggcgcgta ctcattgctc    4980
aaaaagaaat tagtagacaa agtaaaatcg tggtttgaag attttggtgg tggaggcgat    5040
ggaagctatc tatttgacca tccaatttgg caaaggtttg ggagctacac aggtggactt    5100
aactttaatg gcggtcgtca ctatggtatc gactttcaaa tgcctactgg aacgaacatt    5160
tatgctgtta aaggcggtat agctgataaa gtatggactg attacggtgg cggtaattct    5220
atacaaatta gaccggtgc taacgaatgg aactggtata tgcatttatc taagcaatta    5280
gcaagacaag gccaacgtat taaagctggt caactgatag ggaaatcagg tgctacaggt    5340
aatttcgtta gaggagcaca cttacatttc caattgatgc aagggtcgca tccagggaat    5400
gatacagcta agatccaga aaaatggttg aagtcactta aggtagtgg cgttcgaagt    5460 ggttcaggtt ttaataaggc tgcatctgct tgggcaggcg atatacgtcg tgcagcaaaa    5520
cgaatgggtg ttaatgttac ttcgggtgat gtaggaaata ttattagctt gattcaacac    5580
gaatcaggag gaaatgcagg tataactcaa tctagtgcgc ttagagacat caacgtttta    5640
cagggcaatc cagcaaaagg attgcttcaa tatatcccac aaacatttag acattatgct    5700
gttagaggtc acaacaatat atatagtggt tacgatcagt tattagcgtt ctttaacaac    5760
agctattggc gctcacagtt taacccaaga ggtggtggt ctccaagtgg tccaagaaga    5820
tatgcgaatg gtggtttgat tacaaagcat caacttgctg aagtgggtga aggagataaa    5880
```

| | |
|---|---|
| caggagatgg ttatccctt aactagacgt aaacgagcaa ttcaattaac tgaacaggtt | 5940 |
| atgcgcatca tcggtatgga tggcaagcca ataacatca ctgtaaataa tgatacttca | 6000 |
| acagttgaaa aattgttgaa acaaattgtt atgttaagtg ataaaggaaa taaattaaca | 6060 |
| gatgcattga ttcaaactgt ttcttctcag gataataact taggttctaa tgatgcaatt | 6120 |
| agaggtttag aaaaaatatt gtcaaaacaa agtgggcata gagcaaatgc aaataattat | 6180 |
| atgggaggtt tgactaatta a | 6201 |

<210> SEQ ID NO 25
<211> LENGTH: 1830
<212> TYPE: DNA
<213> ORGANISM: Staphylococcus aureus

<400> SEQUENCE: 25

| | |
|---|---|
| atgaaaaagc aaataatttc gctaggcgca ttagcagttg catctagctt atttacatgg | 60 |
| gataacaaag cagatgcgat agtaactaaa gattatagta agaatcaag agtgaatgag | 120 |
| aacagtaaat acgatacacc aattccagat tggtatctag gtagtatttt aaacagatta | 180 |
| ggggatcaaa tatactacgc taaggaatta actaataaat acgaatatgg tgagaaagag | 240 |
| tataagcaag cgatagataa attgatgact agagttttgg gagaagatca ttatctatta | 300 |
| gaaaaaaga agcacaata tgaagcatac aaaaaatggt ttgaaaaaca taaaagtgaa | 360 |
| aatccacatt ctagtttaaa aaagattaaa tttgacgatt ttgatttata tagattaacg | 420 |
| aagaagaat acaatgagtt acatcaatca ttaaaagaag ctgttgatga gtttaatagt | 480 |
| gaagtgaaaa atattcaatc taaacaaaag gatttattac cttatgatga agcaactgaa | 540 |
| aatcgagtaa caaatggaat atatgatttt gtttgcgaga ttgacacatt atacgcagca | 600 |
| tattttaatc atagccaata tggtcataat gctaaagaat taagagcaaa gctagatata | 660 |
| attcttggtg atgctaaaga tcctgttaga attacgaatg aaagaataag aaaagaaatg | 720 |
| atggatgatt taaattctat tattgatgat ttctttatgg atacaaacat gaatagacca | 780 |
| ttaaacataa ctaaatttaa tccgaatatt catgactata ctaataagcc tgaaaataga | 840 |
| gataacttcg ataaattagt caagaaaaca agagaagcaa tcgcaaacgc tgacgaatct | 900 |
| tggaaaacaa gaaccgtcaa aaattacggt gaatctgaaa caaaatctcc tgttgtaaaa | 960 |
| gaagagaaga agttgaaga acctcaatta cctaaagttg aaaccagca agaggataaa | 1020 |
| attacagttg gtacaactga agaagcacca ttaccaattg cgcaaccact agttaaaatt | 1080 |
| ccacagggca caattcaagg tgaaattgta aaaggtccgg aatatctaac gatggaaaat | 1140 |
| aaaacgttac aaggtgaaat cgttcaaggt ccagatttcc caacaatgga acaaaacaga | 1200 |
| ccatctttaa gcgataatta tactcaaccg acgacaccga accctatttt aaaaggtatt | 1260 |
| gaaggaaact caactaaact tgaaataaaa ccacaaggta ctgaatcaac gttaaaaggt | 1320 |
| actcaaggag aatcaagtga tattgaagtt aaacctcaag caactgaaac aacagaagca | 1380 |
| tcacattatc cagcgagacc tcaatttaac aaaacaccta agtatgtgaa atatagagat | 1440 |
| gctggtacag gtatccgtga atacaacgat ggaacatttg gatatgaagc gagaccaaga | 1500 |
| ttcaacaagc caagcgaaac aaatgcatac aacgtaacga caaatcaaga tggcacagta | 1560 |
| tcatatggcg ctcgcccgac acaaaacaag ccaagcgaaa caaacgcata taacgtaaca | 1620 |
| acacatgcaa acggccaagt atcatacgga gctcgtccga cacaaaacaa gccaagcgaa | 1680 |
| acgaacgcat ataacgtaac aacacatgca acggtcaag tgtcatacgg agctcgccca | 1740 |
| acacaaaaca agccaagtaa aacaaatgca tacaatgtaa caacacatgc agatggtact | 1800 |

```
gcgacatatg gtcctagagt aacaaaataa                                    1830

<210> SEQ ID NO 26
<211> LENGTH: 435
<212> TYPE: DNA
<213> ORGANISM: Staphylococcus aureus

<400> SEQUENCE: 26
atgaaaaaag taatcggact gctactagta agtacattag ctttaacagc ttgtggtgaa      60
aaagaaaaac caaaaaaga agaaaataaa aagtcacaaa cacaaaaaca caaagatagc     120
aaaccaaaaa cgcaacaaga aaaaatgaaa aaagttgaag ataaaaatcc acctaataat     180
agcatacaaa ataattcaaa caatcaaaac caatcacaaa acaatcaact taataataat     240
tcagatccat ctaataatac tcctgcaaat ataaataaaa acgattcaca aaatactaat     300
ttaaatgatg agtatgtcgt ttcgcctggc tggactaaag atgaacaggc taaagctttt     360
gaagagtaca aaaaaggaaa agaagacgaa gcaagagctg gtgctagcgc agtaccagga     420
gccaatatta actaa                                                     435

<210> SEQ ID NO 27
<211> LENGTH: 3774
<212> TYPE: DNA
<213> ORGANISM: Staphylococcus aureus

<400> SEQUENCE: 27
atggcgaaaa aatttaatta caaactacca tcaatggttg cattaacgct tgtaggttca      60
gcagtcactg cacatcaagt tcaagcagct gagacgacac aagatcaaac tactaataaa     120
aatgttttag atagtaataa agttaaagca actactgaac aagcaaaagc tgaggtaaaa     180
aatccaacgc aaaacatttc tggcactcaa gtatatcaag accctgctat tgtccaacca     240
aaagcagcga ataaaacagg caatgctcaa gtaaatcaaa aggttgatac tacacaagta     300
aatggtgaca ctcgtgcgac tcaatcaact acatcaaata tgcgaaaacc tgttacaaag     360
tcaacaaaca caacagcacc taaaacgaac aataatgtta caagtgctgg atatagttta     420
gttgatgatg aagatgataa ttcagaaaat caaattaatc cagaattaat taaatcagct     480
gctaaacctg ctgctcttga aacgcaatat aaagccgcag caccaaaagc aacacctgtt     540
gcacctaaag ctaaaactga agctacacca aaagtaacta cttttagtgc ttcagcacaa     600
ccaagatcag ccgctgcagc acctaaaacg agtttgccaa aatataaacc gcaagtaaac     660
tcatcaatta atgattacat tcgtaaaaat aatttaaaag cacctaagat agaggaagat     720
tatacatctt acttccctaa atacgcatac cgtaacggtg taggtcgtcc tgaaggtatc     780
gttgttcatg atacagctaa tgatcgttcg acgataaatg gcgaaattag ttatatgaaa     840
aacaactatc aaaacgcatt cgtacatgca tttgttgatg gggatcgtat aatcgaaaca     900
gcaccaacgg attacttatc ttgggtgtc ggtgcagtcg gtaaccctag attcatcaat     960
gttgaaatcg tgcacacaca cgattatgct tcatttgcac gttcaatgaa taactatgct    1020
gactatgcag ctacacaatt acaatattat ggttttaaaac ctgatagtgc tgaatatgat    1080
ggaaatggta cagtatggac tcactacgct gtaagtaaat atttaggtgg tacggaccat    1140
gccgatccac atggatattt aagaagtcat aattatagtt atgatcaact atatgactta    1200
attaatgaaa atatttaat aaaaatgggt aaagtggcgc catggggtac gcaatctaca    1260 actacccta ctacaccatc aaaaccatca acaccgtcga aaccatcaac accatcaact    1320
```

-continued

```
ggtaaattaa cagttgctgc taataatggt gtcgcacaaa tcaaacctac aaatagtggt   1380
ttatatacta ctgtttacga caaaactggt aaagcaacta atgaagttca aaaaacattt   1440
gctgtatcta aaacagctac attaggtaat caaaaattct atcttgttca agattacaat   1500
tctggtaata aatttggttg ggttaaagaa ggcgatgtgg tttacaacac agctaaatca   1560
cctgtaaatg taaatcaatc atattcaatc aaacctggta cgaaacttta tacagtacct   1620
tggggtacat ctaaacaagt tgctggtagc gtgtctggtt ctggaaacca aacatttaag   1680
gcttcaaagc aacaacaaat tgataaatca atttatttat atggctctgt gaatggtaaa   1740
tctggttggg taagtaaagc atatttagtt gatactgcta aacctacgcc tacaccaaca   1800
cctaagccat caacacctac aacaaataat aaattaacag tttcatcatt aaacggtgtt   1860
gctcaaatta atgctaaaaa caatggctta ttcactacag tttatgacaa aactggtaag   1920
ccaacgaaag aagttcaaaa aacatttgct gtaacaaaag aagcaagtct aggtggaaac   1980
aaattctact tagttaaaga ttacaatagt ccaactttaa ttggttgggt taaacaaggt   2040
gacgttattt ataacaatgc aaaatcacct gtaaatgtaa tgcaaactta tacagtaaaa   2100
ccaggcacta aattatattc agtaccttgg ggtacttata aacaagaagc tggtgcggta   2160
tctggtacag gtaaccaaac ttttaaagcg actaagcaac aacaaattga taaatctatc   2220
tatttatatg gaactgtaaa tggtaaatct ggttggataa gtaaagcata tttagctgta   2280
cctgctgcac ctaaaaaagc tgtagcacaa ccaaaaactg ctgtaaaagc ttatgctgtt   2340
actaaacctc aaacgactca aacagttagc aaaattgctc aagttaaacc aaacaacact   2400
ggtattcgtg cttctgttta tgaaaaaaca gcgaaaaacg gtgcaaaata tgcggatcgt   2460
acattctatg taacaaaaga acgtgcacat ggtaatgaaa catacgtatt attaaataat   2520
acaagtcata atattccatt aggttggttc aatgtaaaag acttaaatgt tcaaaactta   2580
ggcaaagaag ttaaaacgac tcaaaaatat actgttaaca gatcaaataa cggcttatca   2640
atggttcctt ggggtactaa aaaccaagtc attttaacag gcaataacat tgctcaaggt   2700
acatttaatg caacgaaaca agtatctgta ggcaaagatg tttatttata cggtactatt   2760
aataaccgca ctggttgggt aaattcaaaa gatttaactg caccaactgc tgttaaacca   2820
actacatcag ctgccaaaga ttataactac acttatgtaa ttaaaaatgg taatggttat   2880
tactatgtaa caccaaattc tgatacagct aaatactcat taaaagcatt taatgaacaa   2940
ccattcgcag ttgttaaaga acaagtcatt aatggacaaa cttggtacta tggtaaatta   3000
tctaacggta aattagcatg gattaaatca actgatttag ctaaagaatt aattaagtat   3060
aatcaaatag gtatgacatt aaaccaagtt gctcaaatac aagctggttt acaatataaa   3120
ccacaagtac aacgtgtacc aggtaagtgg acagatgcta actttaatga tgttaagcat   3180
gcaatggata cgaagcgttt agctcaagat ccagcattaa aatatcaatt cttacgctta   3240
gaccaaccac aaaatatttc tattgataaa attaatcaat tcttaaaagg taaaggtgta   3300
ttagaaaacc aaggtgctgc atttaacaaa gctgctcaaa tgtatggcat taatgaagtt   3360
tatcttatct cacatgccct attagaaaca ggtaacggta cttctcaatt agcaaaaggt   3420
gcagatgtag tgaacaacaa agttgtaact aactctaaca cgaaatacca taacgtattt   3480
ggtattgctg catatgataa cgatccttta cgtgaaggta ttaaatatgc taaacaagct   3540
ggttgggaca cagtatcaaa agcaatcgtt ggtggtgcta aattcatcgg caactcatat   3600
gttaaagctg gtcaaaatac gctttacaaa atgagatgga atcctgcaca tccaggaaca   3660
caccaatatg ctacagatgt agattgggct aacatcaatg ctaaaatcat caaaggctac   3720
```
tatgataaaa ttggcgaagt cggcaaatac ttcgacatcc cacaatataa ataa    3774

<210> SEQ ID NO 28
<211> LENGTH: 1461
<212> TYPE: DNA
<213> ORGANISM: Staphylococcus aureus

<400> SEQUENCE: 28

| | |
|---|---|
| atgtctaata attttaaaga tgactttgaa aaaaatcgtc aatcgataga cacaaattca | 60 |
| catcaagacc atacggaaga tgttgaaaaa gaccaatcag aattagaaca tcaggataca | 120 |
| atagagaata cggagcaaca gtttccgcca agaaatgccc aaagaagaaa aagacgccgt | 180 |
| gatttagcaa cgaatcataa taaacaagtt cacaatgaat cacaaacatc tgaagacaat | 240 |
| gttcaaaatg aggctggcac aatagatgat cgtcaagtcg aatcatcaca cagtactgaa | 300 |
| agtcaagaac ctagccatca agacagtaca cctcaacatg aagagggata ttataataag | 360 |
| aatgcttttg caatggataa atcacatcca gaaccaatcg aagacaatga taaacacgag | 420 |
| actattaaag aagcagaaaa taacactgag cattcaacag tttctgataa gagtgaagct | 480 |
| gaacaatctc agcaacctaa accatatttt gcaacaggtg ctaaccaagc aaatacatca | 540 |
| aaagataaac atgatgatgt aactgttaag caagacaaag atgaatctaa agatcatcat | 600 |
| agtggtaaaa aaggcgcagc aattggtgct ggaacagcgg tgttgcagg tgcagctggt | 660 |
| gcaatgggtg tttctaaagc taagaaacat tcaaatgacg ctcaaaacaa aagtaattct | 720 |
| ggcaaggtga ataactcgac tgaggataaa gcgtctgaag acaagtcaaa agaacatcat | 780 |
| aatggtaaaa aaggtgcagc aatcggtgct ggaacagcag gtttggctgg aggcgcagca | 840 |
| agtaatagtg cttctgccgc ttcaaaacca catgcctcta ataatgcaag tcaaaacaat | 900 |
| gatgaacatg accatcatga cagagataaa gaacgtaaaa aaggtggcat ggccaaagta | 960 |
| ttgttaccat taattgcagc tgtactaatt atcggtgcat tagcgatatt tggaggcatg | 1020 |
| gcattaaaca atcataataa tggtacaaaa gaaataaaaa tcgcgaatac aaataaaaat | 1080 |
| aatgctgatg aaagtaaaga taagacaca tctaaagacg cttctaaaga taatcaaaaa | 1140 |
| tctacagaca gtgataaatc aaaagatgat caagacaaag cgactaaaga tgaatctgat | 1200 |
| aatgatcaaa acaacgctaa tcaagcgaac aatcaagcac aaaataatca aaatcaacaa | 1260 |
| caagctaatc aaaatcaaca acagcaacaa caacgtcaag gtggtggcca agacataca | 1320 |
| gtgaatggtc aagaaaactt ataccgtatc gcaattcaat actacggttc aggttcaccg | 1380 |
| gaaaatgttg aaaaaattag acgtgccaat ggtttaagtg gtaacaatat tagaaacggt | 1440 |
| caacaaatcg ttattccata a | 1461 |

<210> SEQ ID NO 29
<211> LENGTH: 3825
<212> TYPE: DNA
<213> ORGANISM: Staphylococcus aureus

<400> SEQUENCE: 29

| | |
|---|---|
| atgagctggt ttgataaatt attcggcgaa gataatgatt caaatgatga cttgattcat | 60 |
| agaaagaaaa aaagacgtca agaatcacaa aatatagata acgatcatga ctcattactg | 120 |
| cctcaaaata tgatattta gtgtcgtccg aggggaaaat tccgtttttcc tatgagcgta | 180 |
| gcttatgaaa atgaaaatgt tgaacaatct gcagatacta tttcagatga aaagaacaa | 240 |
| taccatcgag actatcgcaa acaaagccac gattctcgtt cacaaaaacg acatcgccgt | 300 |

```
agaagaaatc aaacaactga agaacaaaat tatagtgaac aacgtgggaa ttctaaaata    360
tcacagcaaa gtataaaata taaagatcat tcacattacc atacgaataa gccaggtaca    420
tatgtttctg caattaatgg tattgagaag gaaacgcaca agtcaaaaac acacaatata    480
tattctaata atacaaatca tcgtgctaaa gattcaacta cagattatca caaagaaagt    540
ttcaagactt cagaggtacc gtcagctatt tttggcacaa tgaaacctaa aaagttagaa    600
aatggtcgta tccctgtaag taaatcttca gaaaaagttg agtcagataa acaaaaatat    660
gataaatatg tagctaagac gcaaacgtct caaaataaac atttagaaca agagaaacaa    720
aaagatagtg ttgtcaagca aggaactgca tctaaatcat ctgatgaaaa tgtatcatca    780
acaacaaaat caacacctaa ttattcaaaa gttgataata ctatcaaaat tgaaaacatt    840
tatgcttcac aaattgttga agaaattaga cgtgaacgag aacgtaaagt gcttcaaaag    900
cgtcgattta aaaaagcgtt gcaacaaaag cgtgaagaac ataaaaacga agagcaagat    960
gcaatacaac gtgcaattga tgaaatgtat gctaaacaag cggaacgcta tgttggtgat   1020
agttcattaa atgatgatag tgacttaaca gataatagta cagaggctag tcagcttcat   1080
acaaatgaaa tagaggatga agctgtatca aatgatgaaa ataaaaaagc gtcaatacaa   1140
aatgaagaca ctgatgacac tcatgtagat gaaagtccat acaattatga ggaagttagt   1200
ttgaatcaag tatcgacaac aaaacaattg tcagatgatg aagttacggt ttcggatgta   1260
acgtctcaac gtcaatcagc actgcaacat aacgttgaag taaataatca agatgaacta   1320
aaaaatcaat ccagattaat tgctgattca gaagaagatg gagcaacgaa tgaagaagaa   1380
tattcaggaa gtcaaatcga tgatgcagaa ttttatgaat taaatgatac agaagtagat   1440
gaggatacta cttcaaatag cgaagataat accaatagag acgcgtctga atgcatgta    1500 gacgctccta aaacgcaaga gcacgcagta actgaatctc aagttaataa tatcgataaa   1560
acggttgata atgaaattga attagcgcca cgtcataaaa aagatgacca acaaaactta   1620
agtgtcaact cattgaaaac gaatgatgtg aatgatggtc atgttgtgga agattcaagc   1680
atgaatgaaa tagaaaagca aaacgcagaa attacagaaa atgtgcaaaa cgaagcagct   1740
gaaagtaaac aaaatgtcga agagaaaact attgaaaacg taaatccaaa gaaacagact   1800
gaaaaggttt caactttaag taaaagacca tttaatgttg tcatgacgcc atctgataaa   1860
aagcgtatga tggatcgtaa aaaagcattca aaagtcaatg tgcctgaatt aaagcctgta   1920
caaagtaaac aagctgcgag tgaaagcaag actgcgactc aaaacacacc atcatcaagt   1980
actgattcac aagagtcaaa cacgaatgca tataaaacaa ataatatgac atcaaacaat   2040
gttgagaaca atcaacttat tggtcatgca gcaacagaaa atgattatca aaatgcacaa   2100
caatattcag agcagaaacc ttctgctgat tcaactcaaa cggaaatatt tgaagaaagc   2160
caagatgata atcaattgga aaatgagcaa gttgatcaat caacttcgtc ttcagtttca   2220
gaagtaagcg acataactga agaaagcgaa gaaacaacac atcaaaacaa tactagtgga   2280
caacaagata atgatgatca acaaaaagat ttacagcttt cattttcaaa tcaaaatgaa   2340
gatacagcta atgaaaatag acctcggacg aatcaaccag atgttgcaac aaatcaagct   2400
gtacaaactt ctaagccgat gattcgtaaa ggcccaaata ttaaattgcc aagtgtttca   2460
ttactagaag aaccacaagt tattgagccg gacgaggact ggattacaga taaaaagaaa   2520
gaacttaatg acgcattatt ttactttaat gtacctgcag aagtacaaga tgtaactgaa   2580
ggtccaagtg ttcaaagatt tgaattatca gttgaaaaag gtgttaaagt ttcaagaatt   2640
acggcattac aagatgacat taaaatggca ttggcagcga aagatattcg tatagaagcg   2700
```

```
ccaattccag gaactagtcg tgttggtatt gaagttccga accaaaatcc aacgacggtc    2760
aacttacgtt ctattattga atctccaagt tttaaaaatg ctgaatctaa attaacagtt    2820
gcgatggggt atagaattaa taatgaacca ttacttatgg atattgctaa aacgccacac    2880
gcactaattg caggtgcaac tggatcaggg aaatcagttt gtatcaatag tatttttgatg   2940 tctttactat ataaaaatca tcctgaggaa ttaagattat tacttattga tccaaaaatg    3000
gttgaattag ctccttataa tggtttgcca catttagttg caccggtaat tacagatgtc    3060
aaagcagcta cacagagttt aaaatgggcc gtagaagaaa tggaaagacg ttataagtta    3120
tttgcacatt accatgtacg taatataaca gcatttaaca aaaaagcacc atatgatgaa    3180
agaatgccaa aaattgtcat agtaattgat gagttggctg atttaatgat gatggctccg    3240
caagaagttg agcagtctat tgctagaatt gctcaaaaag cgagagcatg tggtattcat    3300
atgttggtag ctacgcaaag accatctgtc aatgtaatta caggtttaat taaagccaac    3360
ataccaacaa gaattgcatt tatggtatca tcaagtgtag attcaagaac gatattagac    3420
agtggtggag cagaacgctt gttaggatat ggcgatatgt tatatcttgg tagcggtatg    3480
aataaaccga ttagagttca aggtacattt gtttctgatg acgaaattga tgatgttgtt    3540
gattttatca acaacaaag agaaccggac tacctatttg aagaaaaga attgttgaaa     3600 aaaacacaaa cacaatcaca agatgaatta tttgatgatg tttgtgcatt tatggttaat    3660
gaaggacata tttcaacatc attaatccaa agacatttcc aaattggcta taatagagca    3720
gcaagaatta tcgatcaatt agcaactc ggttatgttt cgagtgctaa tggttcaaaa     3780
ccaagggatg tttatgttac ggaagcagat ttaaataaag aataa                    3825

<210> SEQ ID NO 30
<211> LENGTH: 630
<212> TYPE: DNA
<213> ORGANISM: Staphylococcus aureus

<400> SEQUENCE: 30
atgtcgaatc aaaattacga ctacaataaa aatgaagatg gaagtaagaa gaaaatgagt    60
acaacagcga aagtagttag cattgcgacg gtattgctat tactcggagg attagtatttt    120 gcaattttg catatgtaga tcattcgaat aaagctaaag aacgtatgtt gaacgaacaa      180
aagcaggaac aaaagaaaa gcgtcaaaaa gaaaatgcag aaaaagagag aaagaaaaag      240
caacaagagg aaaagagca gaatgagcta gattcacaag caaaccaata tcagcaattg      300
ccacagcaga atcaatatca atatgtgcca cctcagcaac aagcacctac aaagcaacgt      360
cctgctaaag aagagaatga tgataaagca tcaaaggatg agtcgaaaga taaggatgac      420
aaagcatctc aagataaatc agatgataat cagaagaaaa ctgatgataa taaacaacca      480
gctcagccta aaccacagcc gcaacaacca acaccaaagc caaataataa tcaacaaaac     540
aatcaatcaa atcaacaagc gaaaccacaa gcaccacaac aaaatagcca atcaacaaca     600
aataaacaaa ataatgctaa tgataagtag                                      630

<210> SEQ ID NO 31
<211> LENGTH: 573
<212> TYPE: DNA
<213> ORGANISM: Staphylococcus aureus

<400> SEQUENCE: 31
atgaaattaa aatcattagc agtgttatca atgtcagcgg tggtgcttac tgcatgtggc    60
```

```
aatgatactc caaaagatga acaaaatca acagagtcaa atactaatca agacactaat    120
acaacaaaag atgttattgc attaaaagat gttaaaacaa gcccagaaga tgctgtgaaa    180
aaagctgaag aaacttacaa aggccaaaag ttgaaaggaa tttcatttga aaattctaat    240
ggtgaatggg cttataaagt gacacaacaa aaatctggtg aagagtcaga agtacttgtt    300
gatgataaaa ataaaaaagt gattaacaaa aagactgaaa aagaagatac agtgaatgaa    360
aatgataact ttaaatatag cgatgctata gattacaaaa aagccattaa agaaggacaa    420
aaggaatttg atggtgatat taaagaatgg tcacttgaaa aagatgatgg taaacttgtt    480
tacaatatcg atttgaaaaa aggtaataaa aaacaagaag ttactgttga tgctaagaac    540
ggtaaagtat taaagagtga gcaagatcaa taa                                 573

<210> SEQ ID NO 32
<211> LENGTH: 3030
<212> TYPE: DNA
<213> ORGANISM: Staphylococcus aureus

<400> SEQUENCE: 32
atgaaaaaga aaaattggat ttatgcatta attgtcactt taattattat aattgccata     60
gttagtatga tatttttttgt tcaaacaaaa tatggagatc aatcagaaaa aggatcccaa    120
agtgtaagta ataaaaataa taaaatacat atcgcaattg ttaacgagga tcaaccaacg    180
acatataacg gtaaaaaggt tgagctgggt caagcatttta ttaaaaggtt agcaaatgag    240
aaaaactata aatttgaaac agtaacaaga aacgttgctg agtctggttt gaaaaatggc    300
ggataccaag tcatgattgt tatcccagaa aacttttcaa aattggcaat gcaattagac    360
gctaaaacac catcgaaaat atcactacag tataaaacag ctgtaggaca aaaagaagaa    420
gtagctaaaa acacagaaaa agttgtaagt aatgtactta acgactttaa caaaaacttg    480
gtcgaaattt atttaacaag catcattgat aatttacata atgcacaaaa aatgttggc    540 gctattatga cgcgtgaaca tggtgtgaat agtaaattct cgaattactt attaaatcca    600
attaacgact tcccggaatt atttacagat acgcttgtaa attcgatttc tgcaaacaaa    660
gatattacaa aatggttcca acatacaat aaatcattac tgagtgcgaa ttcagataca    720
ttcagagtga acacagatta taatgtttcg actttaattg aaaaacaaaa ttcattattt    780
gacgaacaca atacagcgat ggataaaatg ttacaagatt ataaatcgca aaaagatagc    840
gtggaacttg ataactatat caatgcatta aaacagatgg acagccaaat tgatcaacaa    900
tcaagtatgc aagatacagg taagaagaa atataaacaaa ctgttaaaga aaacttagat    960
aaattaagag aaatcattca atcacaagag tcaccatttt caaaaggtat gattgaagac   1020
tatcgtaagc aattaacaga atcactccaa gatgagcttg caaacaacaa agacttacaa   1080
gatgcgctaa atagcattaa atgaacaat gctcaattcg ctgaaaactt agagaaacaa   1140
cttcatgatg atattgtcaa agaacctgat tcagatacaa catttatcta taacatgtct   1200
aaacaagact ttatagctgc aggtttaaat gaggatgaag ctaataaata cgaagcaatt   1260
gtcaaagaag caaaacgtta taaaaacgaa tataatttga aaaaaccgtt agcagaacac   1320
attaatttaa cagattacga taaccaagtt gcgcaagaca caagtagttt gattaatgat   1380
ggtgtgaaag tgcaacgtac tgaaacgatt aaaagtaatg atattaatca attaactgtt   1440
gcaacagatc ctcattttaa ttttgaaggc gacattaaaa ttaatggtaa aaaatatgac   1500
attaaggatc aaagtgttca actcgataca tctaacaagg aatataaagt tgaagtcaat   1560
ggcgttgcta aattgaaaaa ggatgctgag aaagatttct taaaagataa aacaatgcat   1620
```

```
ttacaattgt tatttggaca agcaaatcgt caagatgaac caaatgataa gaaagcaacg    1680
agtgttgtgg atgtaacatt gaatcataac cttgatggtc gcttatcgaa agatgcatta    1740
agccagcaat tgagtgcatt atctaggttt gatgcgcatt ataaaatgta cacagataca    1800
aaaggcagag aagataaacc attcgacaac aaacgtttaa ttgatatgat ggttgaccaa    1860
gttatcaatg acatggaaag tttcaaagac gataaagtag ctgtgttaca tcaaattgat    1920
tcaatggaag aaaactcaga caaactgatt gatgacattt taaataacaa aaagaataca    1980
acaaaaaata aagaagatat ttctaagctg attgatcagt tagaaaacgt taaaaagact    2040
tttgctgaag agccacaaga accaaaaatt gataaaggca aaaatgatga atttaatacg    2100
atgtcttcaa atttagataa agaaattagt agaatttctg agaaaagtac gcaattgcta    2160
tcagatacac aagaatcaaa aacaattgca gattcagtta gtggacaatt aaatcaatta    2220
gataataatg tgaataaact acatgcgaca ggtcgagcat taggcgtaag agcgaatgat    2280
ttgaaccgtc aaatggctaa aaacgataaa gataatgagt tattcgctaa agagtttaaa    2340
aaagtattac aaaattctaa agatggcgac agacaaaacc aagcattaaa agcatttatg    2400
agtaatccgg ttcaaaagaa aaacttagaa aatgttttag ctaataatgg taatacagac    2460
gtgatttcac cgacattgtt cgtattattg atgtatttac tatcaatgat tacagcatat    2520
attttctata gctatgaacg tgctaaagga caaatgaatt tcatcaaaga tgattatagt    2580
agtaaaaaca atctttggaa taatgcgatt acgtctggtg ttattggtgc aactggttta    2640
gtagaaggat taattgtcgg tttaattgca atgaataagt ccatgtgtatt agctggctat    2700
```

| | |
|---|---:|
| gctgcaaaac agaagcaagc taaattaaca ccaggctcaa agagagtca attaactgaa | 720 |
| gcgttatttg cagaaaaacc agttgctaaa atgacttga agaaattcc tctattagtt | 780 |
| actaaaaaga atgatgtatc agaaacagtt aatacagata taaagacac tgttaaacaa | 840 |
| aaagaagcta aatttgaaaa tggtgttatt acacgtaaag ctgatgaaaa aacacctaat | 900 |
| aatacagctg ttgacaagaa atcaggtaaa caatctaaaa aaacaacacc ttcaaataaa | 960 |
| cgaaatgcat caaaagcatc gacaaataaa acttcaggtc agaaaaagca acataataag | 1020 |
| aaagcatcac aaggtgcaaa gaaacaaagt agttcaagta actcaacgac aaagactaat | 1080 |
| caaaaaaatt caaaagcaac aaatgctaaa tcatccaatg catcaaaaaa atcaaatgct | 1140 |
| aaagttgaaa aagctaaaag taaaatagag aaacgtacat ttaatgacta a | 1191 |

<210> SEQ ID NO 34
<211> LENGTH: 2310
<212> TYPE: DNA
<213> ORGANISM: Staphylococcus aureus

<400> SEQUENCE: 34

| | |
|---|---:|
| gtggatattg gtaaaaaaca tgtaattcct aaaagtcagt accgacgtaa gcgtcgtgaa | 60 |
| ttcttccaca acgaagacag agaagaaaat ttaaatcaac atcaagataa acaaaatata | 120 |
| gataatacaa catcaaaaaa agcagataag caaatacata agattcaat tgataagcac | 180 |
| gaacgtttta aaaatagttt atcatcgcat ttagaacaga gaaaccgtga tgtgaatgag | 240 |
| aacaaagctg aagaaagtaa aagtaatcag ggtagtaagt cagcatataa caaagatcat | 300 |
| tatttaacag acgatgtatc taaaaaacaa aattcattag attcagtaga ccaagataca | 360 |
| gagaaatcaa aatattatga gcaaaatact gaagcgactt tatcaactaa ttcaaccgat | 420 |
| aaagtagaat caactgacat gagaaagcta agttcagata aaaacaaagt tggtcatgaa | 480 |
| gagcaacatg tactttctaa accttcagaa catgataaag agactagaat tgattttgag | 540 |
| tcttcaagaa ctgattcaga cagctcgatg cagacagaga aaataaaaaa agacagttca | 600 |
| gatggaaata aagtagtaa tctgaaatct gaagtaatat cagacaaatc aaattcagta | 660 |
| ccaatattgt cggaatctga tgatgaagta aataatcaga agccattaac tttgccggaa | 720 |
| gaacagaaat tgaaaaggca gcaaagtcaa aatgagcaaa caaaaactta cacatatggt | 780 |
| gatagcgaac aaaatgacaa gtctaatcat gaaaatgatt taagtcatca tacaccatcg | 840 |
| ataagtgatg ataaagatta cgttatgaga gaagatcata ttgttgacga taatcctgat | 900 |
| aatgatatca atacaccatc attatcaaaa atagatgacg atcgaaaact tgatgaaaaa | 960 |
| attcatgtcg aagataaaca taaacaaaat gcagactcat ctgaaacggt gggatatcaa | 1020 |
| agtcagtcaa gtgcatctca tcgtagcact gaaaaaagaa atatggctat taatgaccat | 1080 |
| gataaattaa acggtcaaaa accaaataca aagacatcgg caaataataa tcaaaaaaag | 1140 |
| gctacatcaa aattgaacaa agggcgcgct acaaataata attatagcgc cattttgaaa | 1200 |
| aagttttgga tgatgtattg gcctaaatta gttattctaa tgggtattat tattctaatt | 1260 |
| gttattttga atgccatttt taataatgtg aacaaaaatg atcgcatgaa tgataataat | 1320 |
| gatgcagatg ctcaaaaata tacgacaacg atgaaaaatg ccaataacgc agttaaatcg | 1380 |
| gtcgttacag ttgaaaatga acatcaaaaa gattcatcat tacctaaaga taaagcatct | 1440 |
| caagacgaag taggatcagg tgttgtatat aaaaaaatctg gagatacgtt atatattgtt | 1500 |
| acgaatgcac acgttgtcgg tgataaagaa aatcaaaaaa taactttctc gaataataaa | 1560 |
| agtgttgttg ggaaagtgct tggtaaagat aaatggtcag atttagctgt tgttaaagca | 1620 |

```
acttcttcag acagttcagt gaaagagata gctattggag attcaaataa tttagtgtta      1680
ggagagccaa tattagtcgt aggtaatcca cttggtgtag actttaaagg cactgtgaca      1740
gaaggtatta tttcaggtct gaacagaaat gttccaattg atttcgataa agataataaa      1800
tatgatatgt tgatgaaagc tttccaaatt gatgcatcag taaatccagg taactcgggt      1860
ggtgctgtcg tcaatagaga aggaaaatta attggtgtag ttgcagctaa aattagtatg      1920
ccaaacgttg aaaatatgtc atttgcaata cctgttaatg aagtacaaaa gattgtaaaa      1980
gaattagaaa caaaaggtaa aattgactat cccgatgtag gtgttaaaat gaagaatatt      2040
gccagtctaa atagttttga aagacaagca gttaaattgc taggaaaagt taagaacggt      2100
gttgttgtag atcaagttga caacaatggt ttagcagatc aatctggtct gaaaaaaggt      2160
gatgtaatta ctgaattaga tggcaaactt ttagaagatg atttacgctt taggcagatt      2220
atatttagtc ataaagatga cttgaaatca attacagcga agatttatag agatggtaaa      2280
gaaaaagaaa ttaatattaa actaaaataa                                       2310
```

<210> SEQ ID NO 35
<211> LENGTH: 627
<212> TYPE: DNA
<213> ORGANISM: Staphylococcus aureus

<400> SEQUENCE: 35

```
atgaaattca aagctatcgt tgcaatcaca ttatcattgt cactattaac cgcctgtggt       60
gctaatcaac ataaagaaaa tagtagtaaa tcaaatgaca ctaataaaaa gacgcaacaa      120
actgataaca ctacacagtc aaatacagaa agcaaaatga ctccacaaga agccgaagat      180
atcgttcgaa acgattacaa agcaagaggt gctaacgaaa atcaaacatt aaattataaa      240
acaaatcttg aacgaagtaa tgaacatgaa tattatgttg aacatctagt ccgcgatgca      300
gttggcacac cattaaaacg ttgcgctatt gttaatcgac acaatggtac gattattaat      360
atttttgatg atatgtcaga aaaagataaa gaagaatttg aagcatttaa aaagagaagc      420
cctaaataca acccaggtat gaatgatcaa gctgaaatgg ataatgagtc ggaagacatt      480
caacatcatg atattgacaa taacaaagcc attcaaaatg acttaccaga tcaaaaagtc      540
gatgataaaa acgataaaaa tgctgttaat aaagaagaaa acacgataa ccgtgaaaat      600 aattcagcag aaactaaagt taaataa                                          627
```

<210> SEQ ID NO 36
<211> LENGTH: 684
<212> TYPE: DNA
<213> ORGANISM: Staphylococcus aureus

<400> SEQUENCE: 36

```
atggataaga aaaagtcat caaatttatg attaatgtat taccaattgt attggtaccg        60
ttaattgttg aacgtaaacg tatcaaacaa catccggacg tacaaaaagt tacagatgct      120
acaagtaaag ttgcttcaaa acatctgca gcaatcagta acacagcgag tgatgttaaa       180
gaatatgtcg gcgataaaaa acaagatttt gaaaataagc gtgaacttaa aaagtttgct      240
agagaacatg atcctgccta tattgagaaa aaggcgaaa attagctaa acaaaatcgt        300 aaagacgctg ataaaatgaa taaaatactt caaaaaaata tcgaaaagcg tcataaagaa      360
gagcaaaaag cccgcgaaaa gaatgaaata caacgtatta agatatgaa aaagtcacaa       420 aaatacgaag taaaagcagg cttaacaccct aataaattag atgagaaaac tgagaaaaaa      480
```

| | |
|---|---|
| ggcgataaac tagctgaaaa aaatcgcaaa gaaatcgcta aaatgaataa aaagttacaa | 540 |
| aaaaatattg aaaaacgaca caagaagaa caaaaacgcc aacaagaagc tgataaagca | 600 |
| cgcatcaagt catttaaaaa atataaagat tatgttgcca aaagcgcctc tcaacaaaat | 660 |
| aaagaaaaca atacagaggc ataa | 684 |

<210> SEQ ID NO 37
<211> LENGTH: 1215
<212> TYPE: DNA
<213> ORGANISM: Staphylococcus aureus

<400> SEQUENCE: 37

| | |
|---|---|
| atgtcatatc attggtttaa gaaaatgtta ctttcaacaa gtatgttaat tttaagtagt | 60 |
| agtagtagtt tagggcttgc aacgcacaca gttgaagcaa aggataactt aaatggagaa | 120 |
| aagccaacga ctaatttgaa tcataatgta acttcaccat cagtaaatag tgaaatgaat | 180 |
| aataatgaga ctgggacacc tcacgaatca aatcaagctg gtaatgaagg aactggttcg | 240 |
| aatagtcgtg atgctaatcc tgattcgaat aatgtgaagc cagactcaaa caaccaaaac | 300 |
| ccaagtccag attcaaaacc tgacccaaat aacccaaacc caggtccgaa tccgaagcca | 360 |
| gacccagata agccgaaacc aaatccggaa ccaaagccag acccagataa gccgaaacca | 420 |
| aatccggatc caaaaccaga tccagacaaa ccgaagccaa atccggatcc aaaaccagat | 480 |
| ccaaatccga atccgaatcc aaaaccagac cctaataagc caaatccaaa tccgtctcca | 540 |
| aatcccaatc aacctgggga ttccaatcaa tctggtggct cgaaaaatgg ggggacatgg | 600 |
| aacccaaatg cttcagatgg atctaatcaa ggtcaatggc aaccaaatgg aaatcaagga | 660 |
| aactcacaaa atcctactgg taatgatttt gtatcccaac gatttttagc cttggcgaat | 720 |
| ggggcttaca gtataatcc gtatatttta aatcaaatta atcaattggg gaagaatat | 780 |
| ggtgaggtaa ctgatgaaga tatctacaat atcatccgta acaaaacttt cagcggaaat | 840 |
| gcatatttaa atggattaca acagcaatcg aattactttta gattccaata tttcaatcca | 900 |
| ttgaaatcag aaaggtacta tcgtaattta gatgaacaag tactcgcatt aattactggc | 960 |
| gaaattggat caatgccaga tttgaaaaag cccgaagata agccggattc aaaacaacgt | 1020 |
| tcatttgagc ctcatgaaaa agatgatttt acagttgtaa aaaacaaga gataataag | 1080 |
| aaaagtgcgt caactgcata tagtaaaagt tggctagcaa ttgtatgttc tatgatggtg | 1140 |
| gtattttcaa tcatgctatt cttatttgta aagcgaaata aaagaaaaa taaaaacgaa | 1200 |
| tcacagcgac gataa | 1215 |

<210> SEQ ID NO 38
<211> LENGTH: 696
<212> TYPE: DNA
<213> ORGANISM: Staphylococcus aureus

<400> SEQUENCE: 38

| | |
|---|---|
| atgaagaaaa cattactcgc atcatcatta gcagtaggtt taggaatcgt agcaggaaat | 60 |
| gcaggtcacg aagcccaagc aagtgaagcg gacttaaata agcatctttt agcgcaaatg | 120 |
| gcgcaatcaa atgatcaaac attaaatcaa aaaccaattg aagctggcgc ttataattat | 180 |
| acatttgact atgaagggtt tacttatcac tttgaatcag atggtacaca ctttgcttgg | 240 |
| aattaccatg caacaggtgc taatggagca gacatgagtg cacaagcacc tgcaactaat | 300 |
| aatgttgcac catcagctga tcaatctaat caagtacaat cacaagaagt tgaagcacca | 360 |
| caaaatgctc aaactcaaca accacaagca tcaacatcaa acaattcaca agttactgca | 420 |

```
acaccaactg aatcaaaagc atcagaaggt tcatcagtaa atgtgaatga tcatctaaaa    480
caaattgctc aacgtgaatc aggtggcaat attcatgctg taaatccaac atcaggtgca    540
gctggtaagt atcaattctt acaatcaact tgggattcag tagcacctgc taaatataaa    600
ggtgtatcac cagcaaatgc tcctgaaagt gttcaagatg ccgcagcagt aaaactatat    660
aacactggtg gcgctggaca ttgggttact gcataa                              696
```

<210> SEQ ID NO 39
<211> LENGTH: 465
<212> TYPE: RNA
<213> ORGANISM: Staphylococcus aureus

<400> SEQUENCE: 39

```
augaaaagau uguuagguuu auuauuagug agcacguuag uguuaagugc auguggaaau     60
gaugagaauc aggaagaauc uaaaaagaa guuaaaucaa agaaaagaa aauugagaag     120 gaaaaggaaa auaaaucgaa aaaagauaag gaaaaagaag uugcaacaca acaacaacca    180
gacaaucaaa ccguugaaca accccaauca caagagcaau cgguucaaca accgcaacaa    240
cagauaccac aaaauagugu uccucagcaa augccaag uucaacaaaa caaaaagcaa     300
aaaguugauu uaauaauau gccucccacu gauuuucua cagaggguau gucugagcag     360
gcucaaaaac aaauugaaga gcuuucaaug caaaaagacu aucauggucu gucacaaaga    420
gaauacaaug auagaguuuc ugaaauuaua aauaaugaua auuga                    465
```

<210> SEQ ID NO 40
<211> LENGTH: 555
<212> TYPE: RNA
<213> ORGANISM: Staphylococcus aureus

<400> SEQUENCE: 40

```
auguuaaaag gaugcggcgg uugccuuauu ucuuuuauua uauuaauuau cuuauuauca     60
gccuguucaa ugauguuuag uaauaaugac aauuccacua guaaucaauc aucaaaaacg    120
caauuaacuc aaaaagacga agauaaaagu gaaaauaugc cugaagaaaa aucagaauca    180
gaaacagaua aggauuuaca aucaaccgaa gaaguacccg caaaugaaaa uacugaaaau    240
aaucaacaug aaauugauga auaacaaca acagaucaau cagaugauga auuaacaca     300 ccaaacguug cagaagaaga aucacaagau gacuugaaag augauuuaaa agaaaagcaa    360
caaccaagug accaucauca auccacgcaa ccuaagacuu caccaucaac ugaaacaaac    420
aagcaacaau cauuugcuaa uuguaagcaa cuuagacaag uauauccgaa ugugucacu    480 gccgaucauc cagcauaucg accacauuua gauagagaua agauaaacg ugcauguga     540 ccugauaaau auuaa                                                     555
```

<210> SEQ ID NO 41
<211> LENGTH: 390
<212> TYPE: RNA
<213> ORGANISM: Staphylococcus aureus

<400> SEQUENCE: 41

```
augaagaaau uaaucaucag cauuaugcg aucaugcuau uuuuaacagg uugugguaaa      60
agccaagaga aagccacucu ggaaaaggau aucgauaauu acaaaaaga aaauaaagaa    120 uuaaaagaua aaaagaaaa gcuucaacaa gaaaaagaaa aauugcaga uaagcaaaaa    180 gaccuugaaa aagaagugaa agauuuaaaa ccuucaaaag aagauaacaa ggacgauaaa    240
```

| | |
|---|---|
| aaagacgaag acaaaaauaa agacaaagau aaagaggcau cacaagauaa gcaaucaaaa | 300 |
| gaucaaacua agucaucgga uaaagauaau cacaaaaagc cuacaucaac agauaaagau | 360 |
| caaaaagcua augacaaaca ccaaucauaa | 390 |

<210> SEQ ID NO 42
<211> LENGTH: 2982
<212> TYPE: RNA
<213> ORGANISM: Staphylococcus aureus

<400> SEQUENCE: 42

| | |
|---|---|
| augaagaacg cauuuaaauu auuuaaaaug gaucugaaga aaguagcuaa gacgccagcu | 60 |
| guguggauua ucuuagcagg cuuagcuauu uugccaucgu ucuacgcuug guuuaacuua | 120 |
| ugggcaaugu gggauccaua uggcaacacg ggacacauca aggucgcagu cguuaaugaa | 180 |
| gauaaaggcg acacaaucag agggaaaaaa guuaaugucg uaauacgau gguuaacaca | 240 |
| cucaagaaaa auaaaaguuu ugauuggcag uuuguaagua gagagaaagc ugaucaugag | 300 |
| auaaaaaugg guaauauuu ugcagguauu uacaucccau cuaaguuuac acaugaaauu | 360 |
| accgggacac uacguaagca gccucaaaaa gcagauguag aauuuaaggu gaaucagaag | 420 |
| auuaacgcug uugcgucuaa gcuaacagau acugguucgu caguugucgu ugaaaaagcg | 480 |
| aaugaacaau uuaauaaaac aguaacucga gcauuauuag aagaagcuaa caaagcaggu | 540 |
| uuaacuauug aagaaaaugu gccgacaauu aauaagauaa aaaaugcggu auauucggca | 600 |
| gauaaagcuu uaccuaagau uaaugacuuu gcgauaaaaa uuguauauuu gaauaaccac | 660 |
| caagcggauu uagauaaaua ugcgaaugau uuuagaaaac uaggaaauua uaaggugau | 720 |
| auuuuagaug cucagaaaaa auuaaacgaa gucaaugguug cuauuccgca acuuaaugaa | 780 |
| aaggcuaagu ugauauuagc uuuaaauauu uauaugccga aaauugaaaa agcguuaaau | 840 |
| uuugcagcug augacgugcc agcgcaguuc ccuaaaauua aucaaggacu uaacauugcg | 900 |
| agucaaggua uugaucaagc uaauggacag uuaaaugaug ccaaaggcuu cgucacacaa | 960 |
| guuagaagua gagucggua uuaucaagaa gcaaucgac gcgcgcaaga uuugaaucga | 1020 |
| agaaaccagc aacagauucc ucaaaauagc gcggcgaaca acgaaacauc aaauagugca | 1080 |
| ccugcagcug guaauggugu aacaucaacg ccaccaagug caccaaaugg caauacuaca | 1140 |
| ccaaauaaua auguuacgca aaauaccgca ccaaauagua auaaugcacc uguaucgacu | 1200 |
| acaccacaaa guacaagcgg gaaaaaagau ggucaaaguu uugcagauau aacaacaaca | 1260 |
| caagucagca cagcuaacga gaacacacaa aauauuacag auaaagaugu aaaucaaug | 1320 |
| gaagcggcau uaacgggcuc uuuauuauca uuaucaaaua auuagauac ccaagcgaaa | 1380 |
| gccgcacaaa aagauaguca ggcauuacgu aauauucgu auggcauuuu agcaucggac | 1440 |
| aagccaucug auuuuagaga gucuuuagau aauguuaagu ccgguuuaga auacacaacu | 1500 |
| caauauaauc aacaauuuau cgauacauua aaagagauug agaagaauga aaauguugau | 1560 |
| uuaucaaaag aaauugauaa gguaaagaca gcuauaauc gaauuaauga aucauuaagg | 1620 |
| uuaguuaauc aauuaaguaa ugcauuaaag aaugguaguu caggaacugc ugaagcuacu | 1680 |
| aaauuacuag aucaacuguc aaaacugaau ucaucauuau caucauuuag agauuauguu | 1740 |
| aaaaagauc uuaacagcuc uuuaguauca auaucacaac guauuaugga ugaauugaac | 1800 |
| aagggcaaa cggcauuguc uaauguucag cuaagcuaa auacaauuga ucaagucauc | 1860 |
| aacaguggc aaucuauuuu aaaaaauggu aaaacacgua cgaucguuu acaaacagua | 1920 |
| uuaccaagua uugaacaaca auacauuagu gcauuaaaaa augcucaagc aaacuucccg | 1980 |

-continued

| | |
|---|---|
| aaagugaaaa gugauguagc gaaagcagcu aacuuuguac guaacgauuu accacaguug | 2040 |
| gagcaacguu uaaccaaugc gacugcaagu gugaauaaaa auuuaccaac guuauaaau | 2100 |
| gguuaugauc aagcgguagg auuacuaaau aaaaaucagc cacaagcgaa aaaggcuuua | 2160 |
| ucagauuuag cugauuuugc acaaaauaaa uugccagaug uugaaaaaga ucugaaaaaa | 2220 |
| gcgaauaaga uuucaagaa guuagacaaa gacgaugcag ucgauaaauu aaucgacaca | 2280 |
| cuuaagaaug auuugaaaaa gcaagcgggu auuaugcaa auccuauuaa uaagaagacu | 2340 |
| guugauguuu ucccaguuaa ggauuaugga ucagggauga caccauucua uacugcauua | 2400 |
| ucgguauggg uaggcgcacu cuuaaugguua agccuauuaa cuguugauaa uaaacauaag | 2460 |
| agcuuagagc caguguuaac gacacgacaa guauucuuag guaaagcagg auucuuuaua | 2520 |
| augcuuggua uguugcaagc acucauugua ucgguuggag auuuguuaau ccuaaaagca | 2580 |
| ggaguugagu caccuguauu auucguacuu auaacgauuu ucuguucgau auuuucaac | 2640 |
| ucaaucguau aucgugcgu aucauuacuu gguaacccag guaaagccau ugcaaucgua | 2700 |
| uugcuuguau uacaaauugc agguggugga gguacauucc caauucaaac gacaccacaa | 2760 |
| uuuuuccaaa acauuucgcc auacuuacca uuuacguaug caauugauuc auuacgugaa | 2820 |
| acaguaggcg guauuguucc ggaaaucuua auuacaaaau uaauuauauu aacguuauuu | 2880 |
| ggcauaggau ucuucguugu agguuuaauu uuaaaaccug uaacagaucc auugaugaag | 2940 |
| cgcguaucug aaaaaguuga ccaaaguaac guuacagaau aa | 2982 |

<210> SEQ ID NO 43
<211> LENGTH: 6201
<212> TYPE: RNA
<213> ORGANISM: Staphylococcus aureus

<400> SEQUENCE: 43

| | |
|---|---|
| augaaugaaa aaguagaagg caugaccuug gagcugaaau uagaccauuu aggguguccaa | 60 |
| gaaggcauga aagguuuaaa gcgacaauua ggguuguuua auagugaaau gaaagcuaau | 120 |
| cugucagcau uugauaaguc ugaaaaauca augaaaaau aucaggcgag aauuaagggg | 180 |
| uuaaaugaua ggcuuaaagu ucaaaaaaag auguauucuc aaguagaaga ugagcuuaaa | 240 |
| caaguuaacg cuaauuacca aaaagcuaaa uccagugaa aagauguuga gaaagcauau | 300 |
| uuaaaguuag uagaagccaa uaaaaagaa aaauuagcuc uugauaaauc uaagaagcc | 360 |
| uuaaaaucau cgaauacaga acuuaaaaaa gcugaaaauc aauauaaacg uacaaaucaa | 420 |
| cguaaacaag augcguauca aaaacuuaaa caguugagau augcagaaca aaagcuuaag | 480 |
| aauaguaacc aagcuacuac ugcacaacua aaaagagcaa gugacgcagu acagaagcag | 540 |
| uccgcuaagc auaagcacu uguuaacaa uauaaacaag aaggcaauca aguucaaaaa | 600 |
| cuaaagugc aaaugacaa ucuuucaaaa ucaaugaua aaauugaaag uucuuacgcu | 660 |
| aaaacuaaua cuaauuaaa gcaaacgaaa aagaauuua augauuuaaa caauacuauu | 720 |
| aagaaucaua gcgcuaaugu cgcaaaagcu gaaacagcug uuaauaaaga aaaagcugcu | 780 |
| uuaauaauu uggagcguuc aauagauaaa gcuucauccg aaaugaagac uuuuaacaaa | 840 |
| gaacaaauga uagcucaaag ucauuccggu aaacuugcaa gucaagcgga gucauguca | 900 |
| aagaaauuua guucuauugg agacaaaaug acuucccugg gacguacaau gacgauggggc | 960 |
| guaucuacac caauuacuuu aggguuaggu gcagcauuaa aaacaagugc agacuuugaa | 1020 |
| ggccaaaugu cucgaguugg agcgauugcg caagcaagca guaaagacuu gaaaagcaug | 1080 |

-continued

```
ucuaaucaag caguugacuu aggagcuaaa accaguaaaa gugcuaacga agugcuaaa    1140 gguauggaag aauuggcagc uuuaggcuuu aaugccaaac aaacaaugga ggcuaugcca    1200 ggguuauca gugcagcaga agcaaguggu gcagaaaugg cuacaacugc aacuguaaug    1260
gcuucagcga uuaacucuuu cgguuuaaaa gcaucgaug caaaucaugu ugcugauuua    1320
cuugcgagau cagcaaauga uagugcugca gauauucagu acaugggaga ugcauugaag    1380
uaugcuggua uccugcaaa agcauuagga guuucaauag aggacacuuc cgcagcaauu    1440
gaaguuuuau cuaacucagg uuuagagggu ucucaagcag guacugcccu aagagcuuca    1500
uuuaucaggc uagcuaaucc aaguaaaaau acagcaaagg aaaugaaaaa auuagguauu    1560
cauuugucug augcuaaagg ucaauuuguu ggcaugggug aauugauuag acaguuccaa    1620
gauaauauga aaggcaugac gagagaacaa aaacuagcua caguggcuac aauaguuggu    1680
acugaagcag caaguggauu uuuagccuug auugaagcgg gaccagauaa aauuaauagc    1740
uauaguaaau ccuuaaagaa uuccaauggc gaaaguaaaa aagcagcaga uuugaugaaa    1800
gauaaucuca aaggcgcucu ggaacaauua gguggcgcuu uugaaucauu agcaaucgaa    1860
gucgguaaag auuuaacgcc uaugauuaga gcaggagcgg aagguuuaac aaaauuaguu    1920
gauggauuua cacaucuccc ugguuggguu agaaaagcuu caguaggauu agcacuuuuu    1980
ggugcaucua uuggcccugc uguucuugcu gguggcuuau aauacgugc aguuggaagu    2040 gcugcuaaag gcuaugcauc auuaaauaga cgcauugcug aaaauacaau acugucuaau    2100
accaauucaa aagcaaugaa aucuuuaggu cuucaaaccu uauucuugg uucuacaaca    2160 ggaaaaacgu caaaaggcuu uaaaggauua gccggagcua uguuguuaa uuuaaaaccu    2220 auaaauguuu ugaaaaauuc ugcaaagcua gcaauuuuac cguucaaacu uuugaaaaac    2280
gguuuaggau uagccgcaaa auccuuauuu gcaguaagug gaggcgcaag auuugcuggu    2340
guagccuuaa aguuuuuaac aggaccuaua ggugcuacaa uaacugcuau uacaauugca    2400
uauaaaguuu uuaaaccgc auaugaucgu guggaauggu ucagaaacgg uauuaacggu    2460
uuaggagaaa cuauaaaguu uuugguggc aaaauuauug gcggugcugu uaggaagcua    2520
ggagaguuua aaaauuaucu uggaaguaua ggcaaaagcu ucaaagaaaa guuuucaaag    2580
gauaugaaag augguauaa aucuuugagu gacgaugacc uucugaaagu aggagucaac    2640
aaguuuaaag gauuuaugca aaccaugggc acagcuucua aaaagcauc ugauacugua    2700 aaagguuugg ggaaaggugu uucaaaagaa acagaaaaag cuuuagaaaa auacguacac    2760
uauucugaag agaacaacag aaucauggaa aaagucguu uaaacucggg ucaaauaaca    2820
gaagacaaag caaaaaaacu uuugaaaauu gaagcggauu uaucuaauaa ccuuauagcu    2880
gaaauagaaa aagaaauaa aaaggaacuc gaaaaaacuc aagaacuuau ugauaaguau    2940
agugcguucg augaacaaga aaagcaaaac auuuuaacua gaacuaaaga aaaaaugac    3000 uugcgaauua aaaagagca agaacucaau cagaaaauca aagaauugaa agaaaaagcu    3060
uuaagugaug gucagauuuc agaaaaugaa agaaagaaa uugaaaagcu ugaaaaucaa    3120
agacgugaca ucacuguuaa agaauugagu aagacugaaa agagcaagaa gcguauuuua    3180
guaagaaugc aaagaaacag aaauucuuau ucaauagacg aagcgagcaa agcaauuaaa    3240
gaagcagaaa agcaagaaa agcaaaaaaa aagaagugg acaagcaaua ugaagaugau    3300
gucauugcua uaaaaauaa cgucaaaccuu ucuaagucug aaaagauaa auuauuagcu    3360 auugcugauc aaagacauaa ggaugaagua agaaaggcaa aaucaaaaaa agaugcugua    3420
guagacguug uuaaaaagca aaauaaagau auugauaaag agauggauuu auccaguggu    3480
```

-continued

```
cguguauaua aaaauacuga aaaauggugg aauggccuua aaaguuggug gucuaacuuc    3540
agagaagacc aaaagaagaa aagugauaag uacgcuaaag aacaagaaga aacagcucgu    3600
agaaacagag aaaauauaaa gaaaugguuu ggaaaugcuu gggacggcgu aaaaaguaaa    3660
acuggcgaag ccuuuaguaa aaugggcaga aaugcuaauc auuuuggcgg cgaaaugaaa    3720
aaaaugugga guggaaucaa aggaauucca agcaaauuaa guucagguug gagcucagcc    3780
aaaaguucug uaggauauca cacuaaggcu auagcuaaua guacugguaa augguuugga    3840
aaagcuuggc aaucuguuaa aucgacuaca ggaaguauuu acaaucaaac uaagcaaaag    3900
uauucagaug cccucagauaa agcuugggcg cauucaaaau cuauuuggaa agggacauca    3960
aaaugguuua gcaaugcaua uaaaagugca aagggcuggc uaacggauau ggcuaauaaa    4020
ucgcgcucga aaugggauaa uauuucuagu acagcauggu cgaaugcaaa auccguuugg    4080
aaaggaacau cgaaaugguu uaguaacuca uacaaaucuu uaaaagguug acuggagau    4140 auguauucaa gagcccacga ucguuuugau gcaauuucaa guucggcaug gucuaacgcu    4200
aaaucaguau uuaaugguuu uagaaaaugg cuaucaagaa cauaugaaug gauuagagau    4260
auuuguaaag acaugggaag agcugcggcu gauuuaggua aaaauguugc uaauaaagcu    4320
auuggcgguu ugaauagcau gauuggcggu auuaauaaaa uaucuaaagc cauuacugau    4380
aaaaaucuca ucaagccaau accuacauug ucuacuggua cuuuagcagg aaagggugua    4440
gcuaccgaua auucgggagc auuaacgcaa ccgacauuug cuguauuaaa ugauagaggu    4500
ucuggaaacg ccccaggcgg uggaguucaa gaaguaauuc acagggcuga cggaacauuc    4560 caugcaccc aaggacgaga uguggguuguu ccacuaggag uuggagauag uguaauaaau    4620
gccaaugaca cucugaaguu acagcggaug gguguuuugc caaaauucca ugguggauacg    4680 aaaaagaaaa aauggaugga acaaguuacu gaaaaucuug uaaaaaagc aggggacuuc    4740 gguucuaaag cuaaaaacac agcucauaau aucaaaaaag gugcagaaga aaugguugaa    4800
gccgcaggcg auaaaaucaa agauggugca ucuugguuag gcgauaaaau cggcgaugug    4860
ugggauuaug uacaacaucc agggaaacua guaaauaaag uaaugucagg uuuaaauauu    4920
aauuuuggag gcggagcuaa cgcuacagua aaaauugcua aaggcgcgua ucauugcuc    4980 aaaaagaaau uaguagacaa aguaaaaucg ugguuugaag auuuuggugg uggaggcgau    5040
ggaagcuauc uauuugacca uccaauuugg caaaggguuu ggagcuacac agguggacuu    5100
aacuuuaaug gcggucguca cuaugguauc gacuuucaaa ugccuacugg aacgaacauu    5160
uaugcuguua aaggcgguau agcugauaaa guaggacug auuacggugg cgguaauucu    5220
auacaaauua agaccggugc uaacgaaugg aacugguaua ugcauuuauc uaagcaauua    5280
gcaagacaag gccaacguau uaaagcuggu caacugauag ggaaaucagg ugcuacaggu    5340
aauuucguua gaggagcaca cuuacauuuc caauugaugc aagggucgca uccagggaau    5400
gauacagcua aagauccaga aaaaugguug aagucacuua agguaguguu cguucgaagu    5460
gguucaggug uuaauaaggc ugcaucugcu ugggcaggcg auauacgucg ugcagcaaaa    5520
cgaaugggug uuaauguuac uucggugau guaggaaaua uuauuagcuu gauucaacac    5580
gaaucaggag gaaaugcagg uauaacucaa ucuagugcgc uuagagacau caacguuuua    5640
cagggcaauc cagcaaaagg auugcuucaa uauaucccac aaacauuuag acauuaugcu    5700
guuagagguc acaacaauau auauagguu uacgaucagu uauuagcguu cuuuaacaac    5760
agcuauuggc gcucacaguu uaacccaaga ggugguuggu cuccaagugg uccaagaaga    5820
```

| | |
|---|---|
| uaugcgaaug gugguuugau uacaaagcau caacuugcug aaguggguga aggagauaaa | 5880 |
| caggagaugg uuaucccuuu aacuagacgu aaacgagcaa uucaauuaac ugaacagguu | 5940 |
| augcgcauca ucgguaugga uggcaagcca aauaacauca cuguaaauaa ugauacuuca | 6000 |
| acaguugaaa aauuguugaa acaaauuguu auguuaagug auaaaggaaa uaaauuaaca | 6060 |
| gaugcauuga uucaaacugu uucuucagg auaauaacu uagguucuaa ugaugcaauu | 6120 |
| agagguuuag aaaaaauauu gucaaaacaa aguggcaua gagcaaaugc aaauaauuau | 6180 |
| augggagguu ugacuaauua a | 6201 |

<210> SEQ ID NO 44
<211> LENGTH: 1830
<212> TYPE: RNA
<213> ORGANISM: Staphylococcus aureus

<400> SEQUENCE: 44

| | |
|---|---|
| augaaaagc aaauaauuuc gcuaggcgca uuagcaguug caucuagcuu auuuacaugg | 60 |
| gauaacaaag cagaugcgau aguaacuaaa gauuauagua aagaaucaag agugaaugag | 120 |
| aacaguaaau acgauacacc aauuccagau gguaucuag guaguauuuu aaacagauua | 180 |
| ggggaucaaa uauacuacgc uaaggaauua acuaauaaau acgaauaugg ugagaaagag | 240 |
| uauaagcaag cgauagauaa auugaugacu agaguuuugg gagaagauca uuaucuauua | 300 |
| gaaaaaaga agcacaaua ugaagcauac aaaaaauggu uugaaaaaca uaaaagugaa | 360 |
| aauccacauu cuaguuuaaa aaagauuaaa uuugacgauu ugauuuuaua uagauuaacg | 420 |
| aagaaagau acaaugaguu acaucaauca uuaaagaag cuugaugaga guuuaauagu | 480 |
| gaagugaaaa auauucaauc uaaacaaaag gauuuauuac cuuaugauga agcaacugaa | 540 |
| aaucaguaa caaauggaau auaugauuuu guuugcgaga uugacacauu uacgcagca | 600 |
| uauuuuaauc uagccaaua uggucauaau gcuaaagaau uaagagcaaa gcuagauaua | 660 |
| auucuuggug augcuaaaga uccguuaga auuacgaaug aaagaauaag aaaagaaaug | 720 |
| auggaugauu uaaauucuau uauugaugau uucuuuaugg uacaaacau gaauagacca | 780 |
| uuaaacauaa cuaaauuuaa uccgaauauu caugacuaua cuauaagcc ugaaaauaga | 840 |
| gauaacuucg auaaauuagu caaagaaaca agagaagcaa ucgcaaacgc ugacgaaucu | 900 |
| uggaaaacaa gaaccgucaa aaauuacggu gaaucgaaa caaaaucucc uguuguaaaa | 960 |
| gaagagaaga aguugaaga accucaauua ccuaaaguug gaaaccagca agaggauaaa | 1020 |
| auuacaguug guacaacuga agaagcacca uuaccaauug cgcaaccacu aguuaaaauu | 1080 |
| ccacagggca caauucaagg ugaaauugua aaaggccgg aauaucuaac gauggaaaau | 1140 |
| aaaacguuac aaggugaaau cguucaaggu ccagauuucc caacaaugga acaaaacaga | 1200 |
| ccaucuuuaa gcgauaauua uacucaaccg acgacaccga accuauuuu aaaagguauu | 1260 |
| gaaggaaacu caacuaaacu ugaaauaaaa ccacaaggua cugaaucaac guuaaaggu | 1320 |
| acucaaggag aaucaaguga uauugaaguu aaaccucaag caacugaaac aacagaagca | 1380 |
| ucacauuauc cagcgagacc ucaauuuaac aaaacaccua aguaugugaa auauagagau | 1440 |
| gcugguacag guauccguga auacaacgau ggaacauuug gauaugaagc gagaccaaga | 1500 |
| uucaacaagc caagcgaaac aaaugcauac aacguaacga caaaucaaga uggcacagua | 1560 |
| ucauuggcg cucgcccgac acaaaacaag ccaagcgaaa caaacgcaua uaacguaaca | 1620 |
| acacaugcaa acggcaagu aucauacgga gcucgcccga cacaaaacaa gccaagcgaa | 1680 |
| acgaacgcau auaacguaac aacacaugca aacggucaag ugucauacgg agcucgccca | 1740 |

```
acacaaaaca agccaaguaa aacaaaugca uacaauguaa caacacaugc agauggugacu    1800 gcgacauaug guccuagagu aacaaaauaa                                      1830

<210> SEQ ID NO 45
<211> LENGTH: 435
<212> TYPE: RNA
<213> ORGANISM: Staphylococcus aureus

<400> SEQUENCE: 45
augaaaaaag uaaucggacu gcuacuagua aguacauuag cuuuaacagc uuguggugaa      60
aaagaaaaac caaaaaaaga agaaaauaaa aagucacaa cacaaaaaca caaagauagc      120
aaaccaaaaa cgcaacaaga aaaaaugaaa aaaguugaag auaaaaaucc accuaauaau     180
agcauacaaa auaauucaaa caaucaaaac caaucacaaa caaucaacu uaauaauaau     240 ucagauccau cuaauaauac uccugcaaau auaaauaaaa acgauucaca aaauacuaau     300
uuaaaugaug aguaugucgu ucgccuggc uggacaaaag augaacaggc uaaagcuuuu     360
gaagaguaca aaaaaggaaa agaagacgaa gcaagagcug gugcuagcgc aguaccagga     420
gccaauauua acuaa                                                      435

<210> SEQ ID NO 46
<211> LENGTH: 3774
<212> TYPE: RNA
<213> ORGANISM: Staphylococcus aureus

<400> SEQUENCE: 46
auggcgaaaa aauuuaauua caaacuacca ucaauggugu cauuaacgcu uguaggguuca     60 gcagucacug cacaucaagu ucaagcagcu gagacgacac aagaucaaac uacuaauaaa    120
aauguuuuag auaguaauaa aguuaaaagca acuacugaac aagcaaaagc ugagguaaaa    180
aauccaacgc aaaacauuuc uggcacucaa guauauaaag acccugcuau uguccaacca    240
aaagcagcga auaaaacagg caaugcucaa guaaaucaaa agguugauac uacacaagua    300
aauggugaca cucgugcgac ucaaucaacu acaucaaaua augcgaaacc uguuacaaag    360
ucaacaaaca caacagcacc uaaaacgaac aauaauguua caagugcugg auauaguuua    420
guugaugaug aagaugauaa uucagaaaau caaauuaauc cagaauuaau uaaaucagcu    480
gcuaaaccug cugcucuuga aacgcaauau aaagccgcag caccaaaagc aacaccuguu    540
gcaccuaaag cuaaaacuga agcuacacca aaaguaacua cuuuuagugc uucagcacaa    600
ccaagaucag ccgcugcagc accuaaaacg aguuugccaa auauaaaacc gcaaguaaac    660
ucaucaauua augauuacau ucguaaaaau aauuuaaaag caccuaagau agaggaagau    720
uauacaucuu acuuccccuaa aucgcauac cguaacgguga uaggucgucc ugaaggauac    780
guuguucaug auacagcuaa ugaucguucg acgauaaaug gcgaaauuag uuauaugaaa    840
aacaacuauc aaaacgcauu cguacaugca uuuguugaug gggaucgauu aaucgaaaca    900
gcaccaacgg auuacuuauc uuggggugu ggugcagucg guaacccuag auucaucaau    960
guugaaaucg ugcacacaca cgauuaugcu ucauuugcac guucaaugaa uaacuaaugcu   1020 gacuaugcag cuacacaauu acaauauuau gguuuaaaac cugauagcgc ugaauaugau   1080
ggaaauggua caguauggac ucacuacgcu guaaguaaau auuuagggg uacggaccau   1140 gccgauccac auggauauuu aagaagucau aauuauaguu augaucaacu auaugacuuua   1200 auuaaugaaa aauauuuaau aaaaaugggu aaaguggcgc caugggguac gcaaucuaca   1260
```

```
acuaccccua cuacaccauc aaaaccauca acaccgucga aaccaucaac accaucaacu    1320 ggaaauuaa caguugcugc uaauaauggu gucgcacaaa ucaaaccuac aaauaguggu    1380
uuauauacua cuguuuacga caaaacuggu aaagcaacua augaaguuca aaaaacauuu    1440
gcuguaucua aaacagcuac auuagguaau caaaaauucu aucuuguuca agauuacaau    1500
ucugguaaua aauuugguug gguuaaagaa ggcgaugugg uuuacaacac agcuaaauca    1560
ccuguaaaug uaaaucaauc auauucaauc aaaccuggua cgaaacuuua uacaguaccu    1620
ugggguacau cuaacaagu ugcugguagc gugucugguu cuggaaacca aacauuuaag    1680
gcuucaaagc aacaacaaau ugauaaauca auuuauuuau auggcucugu gaaugguaaa    1740
ucugguuggg uaaguaaagc auauuuaguu gauacugcua aaccuacgcc uacaccaaca    1800
ccuaagccau caacaccuac aacaaauauau aaauuaacag uuucaucauu aaacgguguu    1860
gcucaaauua augcuaaaaa caauggcuua uucacuacag uuuaugacaa aacugguaag    1920
ccaacgaaag aaguucaaaa aacauuugcu guaacaaaag aagcaagucu aggauggaaac    1980 aaauucuacu uaguuaaaga uuacaauagu ccaacuuuaa uggguuggu uaaacaaggu    2040 gacguuauuu auaacaaugc aaaaucaccu uaaauguaa ugcaaacuua uacaguaaaa    2100
ccaggcacua aauuauauc aguaccuugg gguacuaua aacaagaagc uggugcggua    2160 ucgguacag guaaccaaac uuuuaaagcg acuaagcaac aacaaauuga uaaaucuauc    2220
uauuuauaug aacguaaa ugguaaaucu gguggauua guaaagcaua uuuagcugua    2280
ccugcugcac cuaaaaaagc uguagcacaa ccaaaaacug cuguaaaagc uuaugcuguu    2340
acuaaaccuc aaacgacuca aacaguuagc aaaauugcuc aaguuaaacc aaacaacacu    2400
gguauucgug cuucuguuua ugaaaaaaca gcgaaaaacg gugcaaaaua ugcggaucgu    2460
acauucuaug uaacaaaaga acgugcacau gguaaugaaa cauacguauu auuaaauaau    2520
acaagucaua auauuccauu agguugguuc aauguaaaag acuuaaaugu caaaacuua    2580 ggcaaagaag uuaaaacgac ucaaaaauau acuguuaaca gaucaaauaa cggcuuauca    2640
augguuccuu gggguacuaa aaaccaaguc auuuuaacag gcaauaacau ugcucaaggu    2700
acauuuaaug caacgaaaca aguaucugua ggcaaagaug uuuauuuaua cgguacuauu    2760
aauaaccgca cugguugggu aaauucaaaa gauuuaacug caccaacugc uguuaaacca    2820
acuacaucag cugccaaaga uuauaacuac acuuauguaa uuaaaaaugg uaaugguuau    2880
uacuauguaa caccaaauuc ugauacagcu aaauacucau uaaaagcauu uaaugaacaa    2940
ccauucgcag uuguuaaaga acaagucauu aauggacaaa cuggguacua ugguaaauua    3000
ucuaacggua aauuagcaug gauuaaauca acugauuuag cuaaagaauu aauuaaguau    3060
aaucaaauag guaugacauu aaaccaaguu gcucaaauac aagcgguuu acaauauaaa    3120 ccacaaguac aacguguacc agguaagugg acagaugcua acuuuaauga uguuaagcau    3180
gcaauggaua cgaagcguuu agcucaagau ccagcauuaa aauaucaauu cuuacgcuua    3240
gaccaaccac aaaauauuuc uauugauaaa auuaaucaau cuuaaaaagg uaagguguaa    3300
uuagaaaacc aaggugcugc auuuaacaaa gcugcucaaa uguauggcau uaaugaaguu    3360
uaucuuaucu cacaugcccu auuagaaaca gguaacggua cuucucaauu agcaaaaggu    3420
gcagauguag ugaacaacaa aguuguaacu aacucuaaca cgaaauacca uaacguauuu    3480
gguauugcug cauaugauaa cgauccuuua cgugaaggua uuaaauagc uaaacaagcu    3540 gguugggaca caguaucaaa agcaaucguu gguggugcua aauucaucgg caacucauau    3600
guuaaagcug gucaaaauac gcuuuacaaa augagaugga auccugcaca uccaggaaca    3660
```

```
caccaauaug cuacagaugu agauugggcu aacaucaaug cuaaaaucau caaaggcuac    3720
uaugauaaaa uuggcgaagu cggcaaauac uucgacaucc cacaauauaa auaa          3774

<210> SEQ ID NO 47
<211> LENGTH: 1461
<212> TYPE: RNA
<213> ORGANISM: Staphylococcus aureus

<400> SEQUENCE: 47
augucuaaua auuuaaaga ugacuuugaa aaaaaucguc aaucgauaga cacaaauuca      60
caucaagacc auacggaaga uguugaaaaa gaccaaucag aauuagaaca ucaggauaca    120
auagagaaua cggagcaaca guuccgcca agaaaugccc aaagaagaaa aagacgccgu     180
gauuuagcaa cgaaucauaa uaaacaaguu cacaaugaau cacaaacauc ugaagacaau    240
guucaaaaug aggcuggcac aauagaugau cgucaagucg aaucaucaca caguacugaa    300
agucaagaac cuagccauca agacaguaca ccucaacaug aagagggaua uuauaauaag    360
aaugcuuuug caauggauaa aucacaucca gaaccaaucg aagacaauga uaaacacgag    420
acuauuaaag aagcagaaaa uaacacugag cauucaacag uuucugauaa gagugaagcu    480
gaacaaucuc agcaaccuaa accauauuuu gcaacaggug cuaaccaagc aaauacauca    540
aaagauaaac augaugaugu aacuguuaag caagacaaag augaaucuaa agaucaucau    600
aguguaaaaa aaggcgcagc aauuggugcu ggaacagcgg guguugcagg ugcagcuggu    660
gcaaugggug uuucuaaagc uaagaaacau ucaaaugacg cucaaaacaa aaguaauucu    720
ggcaagguga auaacucgac ugaggauaaa gcgucgaagg acaagucaaa agaacaucau    780
aaugguaaaa aaggugcagc aaucggugcu ggaacagcag guuuggcugg aggcgcagca    840
aguaauagug cuucugccgc uucaaaaacca caugccucua auaaugcaag ucaaaacaau    900
gaugaacaug accaucauga cagagauaaa gaacguaaaa aagguggcau ggccaaagua    960
uuguuaccau uaauugcagc uguacuaauu aucggugcau uagcgauauu uggaggcaug   1020
gcauuaaaca aucauaauaa ugguacaaaa gaaaauaaaa ucgcgaauac aaauaaaaau   1080
aaugcugaug aaaguaaaga uaagacaca ucuaagacg cuucuaaaga uaaaucaaaa     1140
ucuacagaca gugauaaauc aaaagaugau caagacaaag cgacuaaaga ugaaucugau   1200
aaugaucaaa acaacgcuaa ucaagcgaac aaucaagcac aaaauaauca aaaucaacaa   1260
caagcuaauc aaaaucaaca acagcaacaa caacgucaag gugguggcca aagacauaca   1320 gugaauggue aagaaaacuu uaccgguauc gcaauucaau acuacgguuc agguucaccg   1380
gaaaauguug aaaaaauuag acgugccaau gguuuaagug guaacaauau agaaacgguu   1440
caacaaaucg uuauuccaua a                                            1461

<210> SEQ ID NO 48
<211> LENGTH: 3825
<212> TYPE: RNA
<213> ORGANISM: Staphylococcus aureus

<400> SEQUENCE: 48
augagcuggu uugauaaauu auucggcgaa gauaaugauu caaaugauga cuugauucau     60
agaaagaaaa aaagacguca agaaucacaa aauauagaua acgaucauga cucauuacug    120
ccucaaaaua augauauuua uagcgucccg aggggaaaau uccguuuucc uaugagcgua    180
gcuuaugaaa augaaaaugu ugaacaaucu gcagauacua uuucagauga aaaagaacaa    240
```

```
uaccaucgag acuaucgcaa acaaagccac gauucucguu cacaaaaacg acaucgccgu    300
agaagaaauc aaacaacuga agaacaaaau uauagugaac aacgugggaa uucuaaaaua    360
ucacagcaaa guauaaaaua uaaagaucau ucacauuacc auacgaauaa gccagguaca    420
uauguuucug caauuaaugg uauugagaag gaaacgcaca agucaaaaac acacaauaua    480
uauucuaaua auacaaauca ucgugcuaaa gauucaacua cagauuauca caagaaagu     540 uucaagacuu cagagguacc gucagcuauu uuuggcacaa ugaaaccuaa aaaguuagaa    600
aauggucgua ucccuguaag uaaaucuuca gaaaaaguug agucagauaa acaaaaauau    660
gauaaauaug uagcuaagac gcaaacgucu caaauaaaac auuuagaaca agagaaacaa    720
aaagauagug uugucaagca aggaacugca ucuaaaucau cugaugaaaa uguaucauca    780
acaacaaaau caacaccuaa uuauucaaaa guugauaaua cuaucaaaau ugaaaacauu    840
uaugcuucac aaauuguuga agaaauuaga cgugaacgag aacguaaagu gcuucaaaag    900
cgucgauuua aaaagcguu gcaacaaaag cgugaagaac auaaaaacga agagcaagau     960
gcaauacaac gugcaauuga ugaaauguau gcuaacaaag cggaacgcua uguuggugau   1020
aguucauuaa augaugauag ugacuuaaca gauaauagua cagaggcuag ucagcuucau   1080
acaaugaaaa uagaggauga agcuguauca aaugaugaaa auaaaaaagc gucaauacaa   1140
aaugaagaca cugaugacac ucauguagau gaaaguccau acaauuauga ggaaguuagu   1200
uugaaucaag uaucgacaac aaaacaauug ucagaugaug aaguuacggu ucggaugua    1260 acgucucaac gucaaucagc acugcaacau aacguugaag uaauaauca agaugaacua    1320 aaaaaucaau ccagauuaau ugcugauuca gaagaagaug gagcaacgaa ugaagaagaa   1380
uauucaggaa gucaaaucga ugaugcagaa uuuuaugaau aaaugauac agaaguagau    1440 gaggauacua cuucaaauag cgaagauaau accaauagag acgcgucuga aaugcaugua   1500
gacgcuccua aaacgcaaga gcacgcagua acugaaucuc aaguuaauaa uaucgauaaa   1560
acgguugaua augaaauuga auuagcgcca cgucauaaaa aagaugacca aacaaacuua   1620
agugucaacu cauugaaaac gaaugaugug aaugaugguc auguugugga agauucaagc   1680
augaaugaaa uagaaaagca aaacgcagaa auuacagaaa augugcaaaa cgaagcagcu   1740
gaaaguaaac aaaaugucga agagaaaacu auugaaaacg uaaauccaaa gaaacagacu   1800
gaaaagguuu caacuuuaag uaaaagacca uuuaaguug ucaugacgcc aucugauaaa    1860
aagcguauga uggaucguaa aaagcauuca aaagucaaug ugccugaauu aaagccugua   1920
caaaguaaac aagcugcgag ugaaagcaag acugcgacuc aaaacacacc aucaucaagu   1980
acugauucac aagagucaaa cacgaaugca uauaaaacaa auaauaugac aucaaacaau   2040
guugagaaca aucaacuuau uggucaugca gcaacgaaaa augauuauca aaaugcacaa   2100
caauauucag agcagaaacc uucugcugau ucaacucaaa cggaaauauu ugaagaaagc   2160
caagaugaua aucaauugga aaaugagcaa uugaucaau caacuucguc uucaguuuca    2220
gaaguaagcg acauaacuga agaaagcgaa gaaacaacac aucaaaacaa uacuagugga   2280
caacaagaua augaugauca acaaaaagau uuacagcuuu cauuuucaaa ucaaaaugaa   2340
gauacagcua augaaaauag accucggacg aaucaaccag auguugcaac aaaucaagcu   2400
guacaaacuu cuaagccgau gauucguaaa ggcccaaaua uuaaauugcc aaguguuuca   2460
uuacuagaag aaccacaagu uauugagccg gacgaggacu ggauuacaga uaaaaagaaa   2520
gaacuuaaug acgcauuauu uuacuuuaau guaccugcag aaguacaaga uguaacugaa   2580
gguccaagug uuacaagauu ugaauuauca guugaaaaag guguuaaagu uucaagaauu   2640
```

| | |
|---|---|
| acggcauuac aagaugacau uaaaauggca uuggcagcga aagauauucg uauagaagcg | 2700 |
| ccaauuccag gaacuagucg uguugguauu gaaguuccga accaaaauuc aacgacgguc | 2760 |
| aacuuacguu cuauuauuga aucuccaagu uuuaaaaaug cugaaucuaa auuaacaguu | 2820 |
| gcgaugggu auagaauuaa uaaugaacca uuacuuaugg auauugcuaa aacgccacac | 2880 |
| gcacuaauug caggugcaac uggaucaggg aaaucaguuu guaucaauag uauuuugaug | 2940 |
| ucuuuacuau auaaaaauca uccgaggaa uuaagauuau acuuauuga uccaaaaaug | 3000 |
| guugaauuag ucccuuauaa ugguuugcca cauuuaguug caccgguaau uacagaugauc | 3060 |
| aaagcagcua cacagaguuu aaaaugggcc guagaagaaa uggaaagacg uuauaaguua | 3120 |
| uuugcacauu accauguacg uaauauaaca gcauuuaaca aaaaagcacc auaugaugaa | 3180 |
| agaaugccaa aaauugucau aguaauugau gaguuggcug auuuaaugau gauggcuccg | 3240 |
| caagaaguug agcagucuau ugcuagaauu gcucaaaaag cgagagcaug ugguauucau | 3300 |
| auguuggaug cuacgcaaag accaucuguc aauguaauua caggguuuaau uaaagccaac | 3360 |
| auaccaacaa gaauugcauu uaugguauca ucaaguguag auucaagaac gauauuagac | 3420 |
| agugguggag cagaacgcuu guaggauau ggcgauaugu uauaucuugg uagcgguaug | 3480 |
| aauaaaccga uuagaguuca agguacauuu guuucugaug acgaaauuga ugauguugu | 3540 |
| gauuuuauca acaacaaag agaaccggac uaccuauuug aagaaaaaga auuguugaaa | 3600 |
| aaaacacaaa cacaaucaca agaugaauua uuugaugaug uuugugcauu uaugguuaau | 3660 |
| gaaggacaua uuucaacauc auuaauccaa agacauuucc aaauuggcua uaauagagca | 3720 |
| gcaagaauua ucgaucaauu agagcaacuc gguuauguuu cgagugcuaa ugguucaaaa | 3780 |
| ccaagggaug uuuauguuac ggaagcagau uuaaauaaag aauaa | 3825 |

<210> SEQ ID NO 49
<211> LENGTH: 630
<212> TYPE: RNA
<213> ORGANISM: Staphylococcus aureus

<400> SEQUENCE: 49

| | |
|---|---|
| augucgaauc aaaauuacga cuacaauaaa aaugaagaug gaaguaagaa gaaaaugagu | 60 |
| acaacagcga aaguaguuag cauugcgacg guauugcuau uacucggagg auuaguauuu | 120 |
| gcaauuuuug cauauguaga ucauucgaau aaagcuaaag aacguauguu gaacgaacaa | 180 |
| aagcaggaac aaaagagaaa gcgucaaaaa gaaaaugcag aaaaagagag aaagaaaaag | 240 |
| caacaagagg aaaaagagca gaaugagcua gauucacaag caaccaauua ucagcaauug | 300 |
| ccacagcaga aucaauauca auaugugcca ccucagcaac aagcaccuac aaagcaacgu | 360 |
| ccugcuaaag aagagaauga ugauaaagca ucaaggaug agucgaaaga uaaggaugac | 420 |
| aaagcaucuc aagauaaauc agaugauaau cagaagaaaa cugaugauaa uaaacaacca | 480 |
| gcucagccua aaccacagcc gcaacaacca acaccaaagc caauaauaa ucaacaaaac | 540 |
| aaucaaucaa aucaacaagc gaaaccacaa gcaccacaac aaaauagcca aucaacaaca | 600 |
| aauaaacaaa auaaugcuaa ugauaaguag | 630 |

<210> SEQ ID NO 50
<211> LENGTH: 573
<212> TYPE: RNA
<213> ORGANISM: Staphylococcus aureus

<400> SEQUENCE: 50

| | |
|---|---:|
| augaaauuaa aaucauuagc aguguuauca augucagcgg uggugcuuac ugcaugaggc | 60 |
| aaugauacuc caaagauga aacaaaauca acagagucaa auacuaauca agacacuaau | 120 |
| acaacaaaag auguuauugc auuaaaagau guuaaaacaa gcccagaaga ugcugugaaa | 180 |
| aaagcugaag aaacuuacaa aggccaaaag uugaaaggaa uuucauuuga aaauucuaau | 240 |
| ggugaauggg cuuauaaagu gacacaacaa aaaucgggug aagagucaga aguacuuguu | 300 |
| gaugauaaaa auaaaaaagu gauuaacaaa aagacugaaa aagaagauac agugaaugaa | 360 |
| aaugauaacu uuaauauag cgaugcuaua gauuacaaaa aagccauuaa agaaggacaa | 420 |
| aaggaauuug auggugauau uaaggaaugg ucacuugaaa aagaugaugg uaaacuuguu | 480 |
| uacaauaucg auuugaaaaa agguaauaaa aaacaagaag uuacuguuga ugcuaagaac | 540 |
| gguaaaguau uaaagaguga gcaagaucaa uaa | 573 |

<210> SEQ ID NO 51
<211> LENGTH: 3030
<212> TYPE: RNA
<213> ORGANISM: Staphylococcus aureus

<400> SEQUENCE: 51

| | |
|---|---:|
| augaaaaaga aaaauuggau uuaugcauua auugucacuu uaauuauuau aauugccaua | 60 |
| guuaguauga uauuuuugu ucaaacaaaa uauggagauc aaucagaaaa aggaucccaa | 120 |
| aguguaagua auaaaaauaa uaaaauacau aucgcaauug uuaacgagga ucaaccaacg | 180 |
| acauauaacg guaaaaggu ugagcugggu caagcauuua uuaaaagguu agcaaaugag | 240 |
| aaaaacuaua aauuugaaac aguaacaaga aacguugcug agucuggauu gaaaaaauggc | 300 |
| ggauaccaag ucaugauugu uaucccagaa aacuuucaa aauuggcaau gcaauuagac | 360 |
| gcuaaaacac caucgaaaau aucacuacag uauaaaacag cuguaggaca aaagaagaa | 420 |
| guagcuaaaa acacagaaaa aguuguaagu aauguacuua cgacuuuaa caaaaacuug | 480 |
| gucgaaauuu auuuaacaag caucauugau aauuuacaua augcacaaaa aaauguuggc | 540 |
| gcuauuauga cgcgugaaca uggugugaau aguaaauucu cgaauuacuu auuaaauca | 600 |
| auuaacgacu ucccggaauu auuuacagau acgcuuguaa auucgauuuc ugcaaacaaa | 660 |
| gauauuacaa auggguucca acauacaau aaaucauuac ugagugcgaa uucagauaca | 720 |
| uucagaguga acacagauua uaauguuucg acuuuaauug aaaaacaaaa ucauuauuuu | 780 |
| gacgaacaca auacagcgau ggauaaaaug uuacaagauu auaaaucgca aaaagauagc | 840 |
| guggaacuug uaacuauau caaugcauua aaacagaugg acagccaaau ugaucaacaa | 900 |
| ucaaguaugc aagauacagg uaaagaagaa uauaaacaaa cuguuaaaga aaacuuagau | 960 |
| aaauuaagag aaaucauuca aucacaagag ucaccauuuu caaaagguau gauugaagac | 1020 |
| uaucguaagc aauuaacaga aucacuccaa gaugagcuug caaacaacaa agacuuacaa | 1080 |
| gaugcgcuaa auagcauuaa aaugaacaau gcucaauucg cugaaaacuu agagaaacaa | 1140 |
| cuucaugaug auauugucaa agaaccugau ucagauacaa cauuuaucua uaacaugucu | 1200 |
| aaacaagacu uuauagcugc agguuuaaau gaggaugaag cuauaaaua cgaagcaauu | 1260 |
| gucaagaag caaaacguua uaaaaacgaa uauaauuuga aaaaccguu agcagaacac | 1320 |
| auuauuuaa cagauuacga uaccaaguu gcgcaagaca caaguaguuu gauuaaugau | 1380 |
| ggugugaaag ugcaacguac ugaaacgauu aaaaguaaug auauuaauca auuaacuguu | 1440 |
| gcaacagauc cucauuuuaa uuugaaggc gacauuaaaa uuaauggua aaaauaugc | 1500 |
| auuaaggauc aaaguguuca acucgauaca ucuaacaagg aauauaaagu ugaagucauu | 1560 |

```
ggcguugcua aauugaaaaa ggaugcugag aaagauuucu uaaaagauaa aacaaugcau      1620
uuacaauugu uauuuggaca agcaaaucgu caagaugaac caaaugauaa gaaagcaacg      1680
aguguugugg auguaacauu gaaucauaac cuugaugguc gcuuaucgaa agaugcauua      1740
agccagcaau ugagugcauu aucuagguuu gaugcgcauu auaaaaugua cacagauaca      1800
aaaggcagag aagauaaacc auucgacaac aaacguuuaa uugauaugau gguugaccaa      1860
guuaucaaug cauggaaag uuucaaagac gauaaaguag cuguguuaca ucaaauugau       1920
ucaauggaag aaaacucaga caaacugauu gaugacauuu uaauaacaa aaagaauaca      1980 acaaaaaaua aagaagauau uucuaagcug auugaucagu uagaaaacgu uaaaaagacu      2040
uuugcugaag agccacaaga accaaaaauu gauaaaggca aaaaugauga auuuaauacg      2100
augucuucaa auuuagauaa agaaauuagu agaauuucug agaaaaguac gcaauugcua      2160
ucagauacac aagaaucaaa aacaauugca gauucaguua guggacaauu aaaucaauua      2220
gauaauaaug ugaauaaacu acaugcgaca ggucgagcau uaggcguaag agcgaaugau      2280
uugaaccguc aaauggcuaa aaacgauaaa gauaaugagu uauucgcuaa agaguuuaaa      2340
aaaguauuac aaaauucuaa agauggcgac agacaaaacc aagcauuaaa agcauuuaug      2400
aguaauccgg uucaaaagaa aaacuuagaa aauguuuuag cuaauaaugg uaauacagac      2460
gugauuucac cgacauuguu cguauuauug auguauuuac uaucaaugau uacagcauau      2520
auuuucuaua gcuaugaacg ugcuaaagga caaaugaauu caucaaaga ugauuauagu      2580 aguaaaaaca aucuuuggaa uaaugcgauu acgucgguug uuauuggugc aacugguuua      2640
guagaaggau uaauugucgg uuuaauugca augaauaagu uccauguauu agcuggcuau      2700
agagcgaaau ucaucuuaau ggugauuuua acuaugaugg ucuucguacu uauuaauacg      2760
uauuuacuaa gacagguaaa aucuaucggu auguucuuau ugauugcugc auugggucua      2820
uacuuuguag cuaugaauaa uuugaaagcg gcuggacaag guguugacuaa uaaaauuuca     2880 ccauuaucuu auaucgauaa caugucuuc aauuauuuaa augcagagca uccuauaggc      2940
uuggcgcuag uaauauuaac aguacuugug auuauuggcu uguacugaa caugucuuaua     3000 aaacacuuua agaaagagag auuaaucuaa                                     3030

<210> SEQ ID NO 52
<211> LENGTH: 1191
<212> TYPE: RNA
<213> ORGANISM: Staphylococcus aureus

<400> SEQUENCE: 52
augacgcaac aacaaaauaa uaaaagaaca uuaaaaaaua aacacacuua ucaaaaugaa       60
ccauuaccaa accguaaaga uuuguuguu aguuuuauaa cuggcgcgcu uguugguuca      120
gcuuuaggcu uauauuuuaa aaauaaaguu uaucaaaaag cagaugauuu aaaagucaaa     180
gaacaagaac ugucgcaaaa guugaagaa agaaaaacgc aacuugaaga aacguuugcc     240
uuuacaaaag aacguuuga aggauuuuua acaaaucua aaaaugaaca agcggcauug      300
aaggcacaac aagcagcaau aaaagaagaa gcaagugcaa auaauuuaag cgauacauca      360
caagaggcac aagagauuca agaagcuaaa agagaagcac aaacagaaac ggauaaaagu      420
gcggcuguau caaaugaaga gucaaaggca ucggcauuga aggcacaaca agcagcgaua      480
aaagaagaag caagugcaaa uaauuuaagu gauacaucac aagaagcaca agcgauucaa      540
gaagugaaga agaagcgca agcagaaaca gauaaaagug cagauguauc aaaugaagaa      600
```

| | |
|---|---|
| ucaaaagcau cgacauuaaa cguaucgaaa gaagagucac aagcugaaag auuagcaaac | 660 |
| gcugcaaaac agaagcaagc uaaauuaaca ccaggcucaa aagagaguca auuaacugaa | 720 |
| gcguuauuug cagaaaaacc aguugcuaaa aaugacuuga aagaaauucc ucauuaguu | 780 |
| acuaaaaaga augauguauc agaaacaguu aauacagaua auaaagacac uguuaaacaa | 840 |
| aaagaagcua auuugaaaa ugguguuauu acacguaaag cugaugaaaa aacaccuaau | 900 |
| aaucacgcug uugacaagaa aucagguaaa caaucaaaaa aaacaacacc uucaaauaaa | 960 |
| cgaaaugcau caaaagcauc gacaaauaaa acuucagguc agaaaaagca acauaauaag | 1020 |
| aaagcaucac aaggugcaaa agaaacaaagu aguucaagua acucaacgac aaagacuaau | 1080 |
| caaaaaauu caaaagcaac aaaugcuaaa ucauccaaug caucaaaaaa aucaaaugcu | 1140 |
| aaaguugaaa aagcuaaaag uaaaauagag aaacguacau uuaaugacua a | 1191 |

<210> SEQ ID NO 53
<211> LENGTH: 2310
<212> TYPE: RNA
<213> ORGANISM: Staphylococcus aureus

<400> SEQUENCE: 53

| | |
|---|---|
| guggauauug guaaaaaaca uguaauuccu aaaagucagu accgacguaa gcgucgugaa | 60 |
| uucuuccaca acgaagacag agaagaaaau uuaaaucaac aucaagauaa acaaaauaua | 120 |
| gauaauacaa caucaaaaaa agcagauaag caaauacaua aagauucaau ugauaagcac | 180 |
| gaacguuuua aaaauaguuu aucaucgcau uuagaacaga gaaaccguga ugugaaugag | 240 |
| aacaaagcug aagaaaguaa aaguaaucag gguaguaagu cagcauauaa caaagaucau | 300 |
| uauuuaacag acgauguauc uaaaaaacaa aauucauuag auucaguaga ccaagauaca | 360 |
| gagaaaucaa aauauuauga gcaaaauacu gaagcgacuu uaucaacuaa uucaaccgau | 420 |
| aaaguagaau caacugacau gagaaagcua aguucagaua aaaacaaagu ggucaugaa | 480 |
| gagcaacaug uacuuucuaa accuucagaa caugauaaag agacuagaau ugauuuugag | 540 |
| ucuucaagaa cugauucaga cagcucgaug cagacagaga aaauaaaaaa agacaguuca | 600 |
| gauggaaaua aaaguaguaa ucugaaaaucu gaaguaauau cagacaaauc aaauucagua | 660 |
| ccaauauugu cggaaucuga ugaugaagua aauaaucaga agccauuaac uuugccggaa | 720 |
| gaacagaaau ugaaaaggca gcaaagucaa auugagcaaa caaaaacuua uacauauggu | 780 |
| gauagcgaac aaaaugacaa gucuaaucau gaaaaugauu uaagucauca uacaccaucg | 840 |
| auaagugaug auaagauua cguuaugaga gaagaucaua uuguugacga uaauccugau | 900 |
| aaugauauca uacaccauc auuaucaaaa auagaugacg aucgaaaacu ugaugaaaaa | 960 |
| auucaugucg aagauaaaca uaaacaaaau gcagacucau cugaaacggu gggauaucaa | 1020 |
| agucagucaa gugcaucuca ucguagcacu gaaaaaagaa auauggcuau uaaugaccau | 1080 |
| gauaaauuaa acggucaaaa accaaauaca aagacaucgg caaauaauaa ucaaaaaaag | 1140 |
| gcuacaucaa aauugaacaa agggcgcgcu acaaauaaua auuauagcgc cauuuugaaa | 1200 |
| aaguuuugga ugauguauug gccuaaauua guuauucuaa ugggauuau uauucuaauu | 1260 |
| guuauuuga augccauuuu uaauaagug aacaaaaaug aucgcaugaa ugauaauaau | 1320 |
| gaugcagaug cucaaaaaua uacgacaacg augaaaaaug ccaauaacgc aguuaaaucg | 1380 |
| gucguuacag uugaaaauga aacaucaaaa gauucaucau uaccuaaaga uaaagcaucu | 1440 |
| caagacgaag uaggaucagg uguuguauau aaaaaaucug agaaucguu auauauugu | 1500 |
| acgaaugcac acguugucgg ugauaaagaa aaucaaaaaa uaacuuucuc gaauaauaaa | 1560 |

| | |
|---|---|
| aguguuguug ggaaagugcu ugguaaagau aaauggucag auuuagcugu uguuaaagca | 1620 |
| acuucuucag acaguucagu gaaagagaua gcuauuggag auucaaauaa uuuaguguua | 1680 |
| ggagagccaa auuagucgu agguaauuca cuuggguguag acuuuaaagg cacgugaca | 1740 |
| gaagguauua uuucaggucu gaacagaaau guuccaauug auuucgauaa agauaauaaa | 1800 |
| uaugauaugu ugaugaaagc uuccaaauu gaugcaucag uaaauccagg uaacucgggu | 1860 |
| ggugcugucg ucaauagaga aggaaaauua auuggguguau uugcagcuaa aauuaguaug | 1920 |
| ccaaacguug aaaauaguc auuugcaaua ccuguuaaug aaguacaaaa gauuguaaaa | 1980 |
| gaauuagaaa caaaagguaa aauugacuau cccgauguag uguuaaaau gaagaauauu | 2040 |
| gccagucuaa auaguuuga aagacaagca guuaaauugc uaggaaaagu uaagaacggu | 2100 |
| guuguuguag aucaaguuga caacaauggu uuagcagauc aaucggucu gaaaaaaggu | 2160 |
| gauguaauua cugaauuaga uggcaaacuu uuagaagaug auuuacgcuu uaggcagauu | 2220 |
| auauuuaguc auaaagauga cuugaaauca auuacagcga agauuuauag agaugguaaa | 2280 |
| gaaaaagaaa uuaauauuaa acuaaaauaa | 2310 |

<210> SEQ ID NO 54
<211> LENGTH: 627
<212> TYPE: RNA
<213> ORGANISM: Staphylococcus aureus

<400> SEQUENCE: 54

| | |
|---|---|
| augaaauuca aagcuaucgu ugcaaucaca uuaucauugu cacuauuaac cgccugguggu | 60 |
| gcuaaucaac auaaagaaaa uaguaguaaa ucaaaugaca cuaauaaaaa gacgcaacaa | 120 |
| acugauaaca cuacacaguc aaauacagaa aagcaaauga cuccacaaga agccgaagau | 180 |
| aucguucgaa acgauuacaa agcaagaggu gcuacgaaa aucaaacauu aaauuauaaa | 240 |
| acaaaucuug aacgaaguaa ugaacaugaa uauuaguuug aacaucuagu ccgcgaugca | 300 |
| guuggcacac cauuaaaacg uugcgcuauu guuaucgac acaaugguac gauuauuaau | 360 |
| auuuuugaug auaugucaga aaaagauaaa gaagaauuug aagcauuuaa aaagagaagc | 420 |
| ccuaaauaca acccagguau gaaugaucaa gcugaaaugg auaaugaguc ggaagacauu | 480 |
| caacaucaug auauugacaa uaacaaagcc auucaaaaug acuuaccaga ucaaaaaguc | 540 |
| gaugauaaaa acgauaaaaa ugcuguuaau aagaagaaa aacacgauaa ccgugaaaau | 600 |
| aauucagcag aaacuaaagu uaaauaa | 627 |

<210> SEQ ID NO 55
<211> LENGTH: 684
<212> TYPE: RNA
<213> ORGANISM: Staphylococcus aureus

<400> SEQUENCE: 55

| | |
|---|---|
| auggauaaga aaaagucau caaauuuaug auuaauguau uaccaauugu auugguaccg | 60 |
| uuaauuguug aacguaaacg uaucaaacaa cauccggacg uacaaaaagu uacagaugcu | 120 |
| acaaguaaag uugcuucaaa aacaucugca gcaaucagua acacagcgag ugauguuaaa | 180 |
| gaauaugucg gcgauaaaaa acaagauuuu gaaauaagc gugaacuuaa aaaguuugcu | 240 |
| agagaacaug auccugccua uuugagaaa aaggcgaaa auuagcuaa acaaaaucgu | 300 |
| aaagacgcug auaaaaugaa uaaaauacuu caaaaaaaua ucgaaaagcg ucauaaagaa | 360 |
| gagcaaaaag cccgcgaaaa gaaugaaaua caacguauua agauaugaa aaagucacaa | 420 |

| | |
|---|---:|
| aaaaucgaag uaaaagcagg cuuaacaccu aauaaauuag augagaaaac ugagaaaaaa | 480 |
| ggcgauaaac uagcugaaaa aaaucgcaaa gaaaucgcua aaaugaauaa aaaguuacaa | 540 |
| aaaaauauug aaaaacgaca caaagaagaa caaaaacgcc aacaagaagc ugauaaagca | 600 |
| cgcaucaagu cauuuaaaaa auauaaagau uauguugcca aaagcgccuc ucaacaaaau | 660 |
| aaagaaaaca auacagaggc auaa | 684 |

<210> SEQ ID NO 56
<211> LENGTH: 1215
<212> TYPE: RNA
<213> ORGANISM: Staphylococcus aureus

<400> SEQUENCE: 56

| | |
|---|---:|
| augucauauc auugguuuaa gaaaauguua cuuucaacaa guauguuaau uuuaaguagu | 60 |
| aguaguaguu uagggcuugc aacgcacaca guugaagcaa aggauaacuu aaauggagaa | 120 |
| aagccaacga cuaauuugaa ucauaaugua acuucaccau caguaaauag ugaaaugaau | 180 |
| aauaaugaga cugggacacc ucacgaauca aaucaagcug guaaugaagg aacugguucg | 240 |
| aauagucgug augcuaaucc ugauucgaau aaugugaagc cagacucaaa caaccaaaac | 300 |
| ccaaguccag auucaaaacc ugacccaaau aacccaaacc caggucccgaa uccgaagcca | 360 |
| gacccagaua agccgaaacc aaauccggaa ccaaagccag acccagauaa gccgaaacca | 420 |
| aauccggauc caaaaccaga uccagacaaa ccgaagccaa auccggaucc aaaaccagau | 480 |
| ccaaauccga auccgaaucc aaaaccagac ccuauaagc caauccaaa uccgucucca | 540 |
| aaucccaauc aaccugggga uuccaaucaa ucuggugcu cgaaaaaugg ggggacaugg | 600 |
| aacccaaaug cuucagaugg aucuaaucaa ggucaauggc aaccaaaugg aaaucaagga | 660 |
| aacucacaaa auccuacugg uaaugauuuu guacccaac gauuuuuagc cuuggcgaau | 720 |
| ggggcuuaca aguauaaucc guauauuuua aaucaaauua ucaauuggg gaaagaauau | 780 |
| ggugagguaa cugaugaaga uaucuacaau aucauccgua acaaaaacuu cagcggaaau | 840 |
| gcauauuuaa auggauuaca acagcaaucg aauuacuuua gauuccaaua uuucaaucca | 900 |
| uugaaaucag aaagguacua ucguaauuua gaugaacaag uacucgcauu aauuacuggc | 960 |
| gaaauuggau caaugccaga uuugaaaaag cccgaagaua agccggauuc aaaacaacgu | 1020 |
| ucauuugagc cucaugaaaa agaugauuuu acaguuguaa aaaacaaga gauaauaag | 1080 |
| aaaagugcgu caacugcaua aguaaaagu uggcuagcaa uuguauguuc uaugaugggug | 1140 |
| guauuuucaa ucaugcuauu cuuauuugua aagcgaaaua aaagaaaaa uaaaaacgaa | 1200 |
| ucacagcgac gauaa | 1215 |

<210> SEQ ID NO 57
<211> LENGTH: 696
<212> TYPE: RNA
<213> ORGANISM: Staphylococcus aureus

<400> SEQUENCE: 57

| | |
|---|---:|
| augaagaaaa cauuacucgc aucaucauua gcaguagguu uaggaaucgu agcaggaaau | 60 |
| gcaggucacg aagcccaagc aagugaagcg gacuuaaaua aagcaucuuu agcgcaaaug | 120 |
| gcgcaaucaa augaucaaac auuaaaucaa aaaccaauug aagcuggcgc uuauaauuau | 180 |
| acauuugacu augaagggu uacuauacac uuugaaucag augguacaca cuuugcuugg | 240 |
| aauuaccaug caacagggc uaauggagca gacaugagug cacaagcacc ugcaacuaau | 300 |
| aauguugcac caucagcuga ucaaucuaau caaguacaau cacaagaagu ugaagcacca | 360 |

```
caaaaugcuc aaacucaaca accacaagca ucaacaucaa acaauucaca aguuacugca    420
acaccaacug aaucaaaagc aucagaaggu ucaucaguaa augugaauga ucaucuaaaa    480
caaauugcuc aacgugaauc agguggcaau auucaugcug uaaauccaac aucaggugca    540
gcugguaagu aucaauucuu acaaucaacu ugggauucag uagcaccugc uaaauauaaa    600
gguguaucac cagcaaaugc uccugaaagu guucaagaug ccgcagcagu aaaacuauau    660
aacacuggug gcgcuggaca uuggguuacu gcauaa                              696
```

PROTEINS AND NUCLEIC ACIDS USEFUL IN VACCINES TARGETING *STAPHYLOCOCCUS AUREUS*

CROSS-REFERENCE TO RELATED APPLICATIONS

In accordance with 37 C.F.R. 1.76, a claim of priority is included in an Application Data Sheet filed concurrently herewith. Accordingly, the present invention claims priority as a continuation of U.S. patent application Ser. No. 14/802,602, entitled "PROTEINS AND NUCLEIC ACIDS USEFUL IN VACCINES TARGETING *STAPHYLOCOCCUS AUREUS*", filed Jul. 17, 2015, now U.S. Pat. No. 9,534,022, issued Jan. 3, 2017, which claims priority as a divisional of U.S. patent application Ser. No. 14/110,475, entitled "PROTEINS AND NUCLEIC ACIDS USEFUL IN VACCINES TARGETING *STAPHYLOCOCCUS AUREUS*", filed Nov. 25, 2013, now U.S. Pat. No. 9,085,631, issued Jul. 21, 2015, which is a § 371 national stage entry of International Application No. PCT/EP2012/056069, entitled "PROTEINS AND NUCLEIC ACIDS USEFUL IN VACCINES TARGETING *STAPHYLOCOCCUS AUREUS*", filed Apr. 3, 2012, which claims priority to Danish Patent Application No. PA 2011 70167, entitled "PROTEINS AND NUCLEIC ACIDS USEFUL IN VACCINES TARGETING *STAPHYLOCOCCUS AUREUS*", filed Apr. 8, 2011 and U.S. Provisional Application No. 61/473,376, entitled "PROTEINS AND NUCLEIC ACIDS USEFUL IN VACCINES TARGETING *STAPHYLOCOCCUS AUREUS*", filed Apr. 8, 2011, the entire contents of which are incorporated herein by reference.

FIELD OF THE INVENTION

The present invention relates to the field of antimicrobial prophylaxis and therapy. In particular the present invention relates to novel proteins and polynucleotides derived from *Staphylococcus aureus*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is *Staphyloccocus aureus*. In particular in hospitals this bacterium is of relevance. So-called Methicillin Resistant *S. Aureus* (MRSA) strains jeopardize patient's survival in hospitals, in particular after surgery.

Vaccination is considered to be a very effective method of preventing infectious diseases in human and veterinary health care. Vaccination is the administration of immunogenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immuno-protective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *S. aureus* derived antigenic polypeptides that may serve as constituents in vaccines against *S. aureus* infections and in diagnosis of *S. aureus* infections. It is also an object to provide nucleic acids, vectors, transformed cells, vaccine compositions, and other useful means for molecular cloning as well as for therapy and diagnosis with relevance for *S. aureus*.

SUMMARY OF THE INVENTION

It has been found by the present inventor(s) that *S. aureus*, in particular drug resistant *S. aureus*, expresses a number of hitherto unknown surface exposed proteins which are candidates as vaccine targets as well as candidates as immunizing agents for preparation of antibodies that target *S. aureus*.

So, in a first aspect the present invention relates to a polypeptide comprising a) an amino acid sequence selected from the group consisting of any one of SEQ ID NOs: 1-19, or b) an amino acid sequence consisting of at least 5 contiguous amino acid residues from any one of SEQ ID NOs: 1-19, or c) an amino acid sequence having a sequence identity of at least 60% with the amino acid sequence of a), d) an amino acid sequence having a sequence identity of at least 60% with the amino acid sequence of b), or e) an assembly of amino acids derived from any one of SEQ ID NOs: 1-19 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or ii) a nucleotide sequence consisting of any one of SEQ ID NOs: 20-57.

iii) a nucleotide sequence consisting of at least 10 consecutive nucleotides in any one of SEQ ID NOs: 20-57, iv) a nucleotide sequence having a sequence identity of at least 60% with the nucleotide sequence in i) or ii), v) a nucleotide sequence having a sequence identity of at least 60% with the nucleotide sequence in iii), vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *S. aureus* in the animal.

In a seventh and eighth aspect, the invention relates to 1) a polyclonal antibody in which the antibodies specifically bind to at least one polypeptide of the invention, and which is essentially free from antibodies binding specifically to other *S. aureus* polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with *S. aureus*, in particular infection with multi-resistant *S. aureus*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *S. aureus*, in particular the presence of multi-resistant *S. aureus*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *S. aureus*, in particular the presence of antibodies specific for multi-resistant *S. aureus*, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *S. aureus*, in particular the presence of a nucleic acid characteristic of multi-resistant *S. aureus*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a $15^{th}$ aspect, the invention relates to a method for determining whether a substance, such as an antibody, is potentially useful for treating infection with *S. aureus*, the method comprising contacting the polypeptide of the invention with the substance and subsequently establishing whether the substance has at least one of the following characteristics:

1) the ability to bind specifically to said polypeptide, 2) the ability to compete with said polypeptide for specific binding to a ligand/receptor, and 3) the ability to specifically inactivate said polypeptide.

Finally, in a $16^{th}$ aspect, the invention relates to a method for determining whether a substance, such as a nucleic acid, is potentially useful for treating infection with *S. aureus*, the method comprising contacting the substance with the nucleic acid fragment of claim of the invention and subsequently establishing whether the substance has either the ability to 1) bind specifically to the nucleic acid fragment, or 2) bind specifically to a nucleic acid that hybridizes specifically with the nucleic acid fragment.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" is the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAACC-3' (SEQ ID NO: 58) and 5'-ATACGGGACC-3' (SEQ ID NO: 58) will provide the sequence identity 80% ($N_{ref}=10$ and $N_{dif}=2$).

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immunogen by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule present.

An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce nor elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

Specific Embodiments of the Invention

The Polypeptides of the Invention

In some embodiments the at least 5 contiguous amino acids referred to in option b) in the definition of the first aspect of the invention constitute at least 6, such as at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 at least 28, at least 29, at least 30, at least 31, at least 32, at least 33, at least 34, and at least 35 contiguous amino acid residues. The number can be higher, for all of SEQ ID NOs: 1-19 at least 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, and at least 124 contiguous amino acid residues. Another way to phrase this is that for each of SEQ ID NOs: 1-19, the number of the contiguous amino acid residues is at least N−n, where N is the length of the sequence ID in question and n is any integer between 6 and N−1; that is, the at least 5 contiguous amino acids can be at least any number between 5 and the length of the reference sequence minus one, in increments of one.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, and 128 in any one of SEQ ID NOs: 1-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 126, 127, 128, 129, 130, 131, 132, 133, 134, 135, 136, 137, 138, 139, and 140 in any one of SEQ ID NOs: 1, 2, and 4-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 141, 142, 143, 144, 145, 146, 147, 148, 149, and 150 in any one of SEQ ID NOs: 1, 2, and 4-6, and 8-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 151, 152, 153, 154, 155, 156, 157, 158, 159, 160, 161, 162, 163, 164, 165, 166, 167, 168, 169, 170, 171, 172, 173, 174, 175, 176, 177, 178, 179, and 180 in any one of SEQ ID NOs: 2, 4-6, and 8-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 181, 182, 183, 184, 185, and 186 in any one of SEQ ID NOs: 4-6, and 8-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 187, 188, 189, 190, 191, 192, 193, 194, 195, 196, 197, 198, 199, 200, 201, 202, 203, and 204 in any one of SEQ ID NOs: 4-6, 8-11, 13-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to amino acid residue 205 in any one of SEQ ID NOs: 4-6, 8-11, 13-15, and 17-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 206, 207, 208, 209, 210, 211, 212, 213, 214, 215, 216, 217, 218, 219, 220, 221, 222, and 223 in any one of SEQ ID NOs: 4-6, 8-10, 13-15, and 17-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 224, 225, 226, and 227 in any one of SEQ ID NOs: 4-6, 8-10, 13-15, 18, and 19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, and 392 in any one of SEQ ID NOs: 4-6, 8-10, 13-15, and 18, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 393, 394, 395, 396, 397, 398, 399, and 400 in any one of SEQ ID NOs: 4-6, 8-10, 13, 15, and 18, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, and 482 in any one of SEQ ID NOs: SEQ ID NOs: 4-6, 8-10, 13, and 15, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, and 605 in any one of SEQ ID NOs: 4-6, 8, 10, 13, and 15, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, and 765 in any one of SEQ ID NOs: 4, 5, 8, 10, 13, and 15, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, and 989 in any one of SEQ ID NOs: 4, 5, 8, 10, and 13, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 990, 991, 992, 993, 994, 995, 996, 997, 998, 999, 1000, 1001, 1002, 1003, 1004, and 1005, in any one of SEQ ID NOs: 5, 8, 10, and 13, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, and 1253 in any one of SEQ ID NOs: 5, 8, and 10, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1254, 1255, 1256, 1257, 1258, 1259, 1260, 1261, 1262, 1263, 1264, 1265, 1266, 1267, 1268, 1269, and 1270 in SEQ ID NO: 5 or 10, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, and 2062 in SEQ ID NO: 5, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-19. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, diphtheria toxoid or a fragment thereof. Other suitable carrier molecules are discussed infra.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *S. aureus*, in particular multi-resistant *S. aureus*. The polypeptide may in these cases induce a humeral and/or a cellular immune response.

Epitopes

SEQ ID NOs: 1-19 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised against *S. aureus* or *S. aureus* derived proteins disclosed herein are tested for binding to overlapping oligomeric peptides derived from any one of SEQ ID NO: 1-19. Thereby, the regions of the *S. aureus* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-19 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 20-38) or an RNA fragment (such as SEQ ID NOs 29-58).

The nucleic acid fragment of the invention typically consists of at least 11, such as at least 12, at least 13, at least 14, at least 15, at least 16, at least 17 at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, at least 153, at least 154, at least 155, at least 156, at least 157, at least 158, at least 159, at least 160, at least 161, at least 162, at least 163, at least 164, at least 165, at least 166, at least 167, at least 168, at least 169, at least 170, at least 171, at least 172, at least 173, at least 174, at least 175, at least 176, at least 177, at least 178, at least 179, at least 180, at least 181, at least 182, at least 183, at least 184, at least 185, at least 186, at least 187, at least 188, at least 189, at least 190, at least 191, at least 192, at least 193, at least 194, at least 195, at least 196, at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217, at least 218, at least 219, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, at least 250, at least 251, at least 252, at least 253, at least 254, at least 255, at least 256, at least 257, at least 258, at least 259, at least 260, at least 261, at least 262, at least 263, at least 264, at least 265, at least 266, at least 267, at least 268, at least 269, at least 270, at least 271, at least 272, at least 273, at least 274, at least 275, at least 276, at least 277, at least 278, at least 279, at least 280, at least 281, at least 282, at least 283, at least 284, at least 285, at least 286, at least 287, at least 288, at least 289, at least 290, at least 291, at least 292, at least 293, at least 294, at least 295, at least 296, at least 297, at least 298, at least 299, at least 300, at least 301, at least 302, at least 303, at least 304, at least 305, at least 306, at least 307, at least 308, at least 309, at least 310, at least 311, at least 312, at least 313, at least 314, at least 315, at least 316, at least 317, at least 318, at least 319, at least 320, at least 321, at least 322, at least 323, at least 324, at least 325, at least 326, at least 327, at least 328, at least 329, at least 330, at least 331, at least 332, at least 333, at least 334, at least 335, at least 336, at least 337, at least 338, at least 339, at least 340, at least 341, at least 342, at least 343, at least 344, at least 345, at least 346, at least 347, at least 348, at least 349, at least 350, at least 351, at least 352, at least 353, at least 354, at least 355, at least 356, at least 357, at least 358, at least 359, at least 360, at least 361, at least 362, at least 363, at least 364, at least 365, at least 366, at least 367, at least 368, at least 369, at least 370, at least 371, at least 372, at least 373, at least 374, at least 375, at least 376, at least 377, at least 378, at least 379, at least 380, at least 381, at least 382, at least 383, at least 384, at least 385, at least 386, at least 387 consecutive nucleotides in any one of SEQ ID NOs: 20-57. Longer fragments are contemplated, i.e. fragments having at least 400, at least 500, at least 600, at least 700, at least 800, at least 900, at least 1000, at least 1500, at least 2000, and at least 2500 nucleotides from those of SEQ ID NOs: 20-57 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in *E coli*. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as an attenuated virus (which may in itself be useful as a vaccine agent), a bacteriophage, a plasmid, a minichromosome, and a cosmid.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain (Banerji et al, 1983; Gilles et al, 1983; Grosschedl et al, 1985; Atchinson et al, 1986, 1987; toiler et al, 1987; Weinberger et al, 1984; Kiledjian et al, 1988; Porton et al; 1990), Immunoglobulin Light Chain (Queen et al, 1983; Picard et al, 1984), T Cell Receptor (Luria et al, 1987; Winoto et al, 1989; Redondo et al; 1990), HLA DQα and/or DQβ (Sullivan et al, 1987), β-Interferon (Goodbourn et al, 1986; Fujita et al, 1987; Goodbourn et al, 1988), Interleukin-2 (Greene et al, 1989), Interleukin-2 Receptor (Greene et al, 1989; Lin et al, 1990), MHC Class II 5 (Koch et al, 1989), MHC Class II HLA-DRα (Sherman et al, 1989), β-Actin (Kawamoto et al, 1988; Ng et al; 1989), Muscle Creatine Kinase (MCK) (Jaynes et al, 1988; Horlick et al, 1989; Johnson et al, 1989), Prealbumin (Transthyretin) (Costa et al, 1988), Elastase I (Omitz et al, 1987), Metallothionein (MTII) (Karin et al, 1987; Culotta et al, 1989), Collagenase (Pinkert et al, 1987; Angel et al, 1987), Albumin (Pinkert et al, 1987; Tranche et al, 1989, 1990), α-Fetoprotein (Godbout et al, 1988; Campere et al, 1989), γ-Globin (Bodine et al, 1987; Perez-Stable et al, 1990), β-Globin (Trudel et al, 1987), c-fos (Cohen et al, 1987), c-HA-ras (Triesman, 1986; Deschamps et al, 1985), Insulin (Edlund et al, 1985), Neural Cell Adhesion Molecule (NCAM) (Hirsh et al, 1990), α1-Antitrypain (Larimer et al, 1990), H2B (TH2B) Histone (Hwang et al, 1990), Mouse and/or Type I Collagen (Ripe et al, 1989), Glucose-Regulated Proteins (GRP94 and GRP78) (Chang et al, 1989), Rat Growth Hormone (Larsen et al, 1986), Human Serum Amyloid A (SAA) (Edbrooke et al, 1989), Troponin I (TN I) (Yutzey et al, 1989), Platelet-Derived Growth Factor (PDGF) (Pech et al, 1989), Duchenne Muscular Dystrophy (Klamut et al, 1990), SV40 (Banerji et al, 1981; Moreau et al, 1981; Sleigh et al, 1985; Firak et al, 1986; Herr et al, 1986; Imbra et al, 1986; Kadesch et al, 1986; Wang et al, 1986; Ondek et al, 1987; Kuhl et al, 1987; Schaffner et al, 1988), Polyoma (Swartzendruber et al, 1975; Vasseur et al, 1980; Katinka et al, 1980, 1981; Tyndell et al, 1981; Dandolo et al, 1983; de Villiers et al, 1984; Hen et al, 1986; Satake et al, 1988; Campbell et al, 1988), Retroviruses (Kriegler et al, 1982, 1983; Levinson et al, 1982; Kriegler et al, 1983, 1984a, b, 1988; Bosze et al, 1986; Miksicek et al, 1986; Celander et al, 1987; Thiesen et al, 1988; Celander et al, 1988; Choi et al, 1988; Reisman et al, 1989), Papilloma Virus (Campo et al, 1983; Lusky et al, 1983; Spandidos and Wilkie, 1983; Spalholz et al, 1985; Lusky et al, 1986; Cripe et al, 1987; Gloss et al, 1987; Hirochika et al, 1987; Stephens et al, 1987), Hepatitis B Virus (Bulla et al, 1986; Jameel et al, 1986; Shaul et al, 1987; Spandau et al, 1988; Vannice et al, 1988), Human Immunodeficiency Virus (Muesing et al, 1987; Hauber et al, 1988; Jakobovits et al, 1988; Feng et al, 1988; Takebe et al, 1988; Rosen et al, 1988; Berkhout et al, 1989; Laspia et al, 1989; Sharp et al, 1989; Braddock et al, 1989), Cytomegalovirus (CMV) IE (Weber et al, 1984; Boshart et al, 1985; Foecking et al, 1986), Gibbon Ape Leukemia Virus (Holbrook et al, 1987; Quinn et al, 1989).

Inducible Elements include, but are not limited to MT II—Phorbol Ester (TFA)/Heavy metals (Palmiter et al, 1982; Haslinger et al, 1985; Searle et al, 1985; Stuart et al, 1985; Imagawa et al, 1987, Karin et al, 1987; Angel et al, 1987b; McNeall et al, 1989); MMTV (mouse mammary tumor virus)—Glucocorticoids (Huang et al, 1981; Lee et al, 1981; Majors et al, 1983; Chandler et al, 1983; Lee et al, 1984; Ponta et al, 1985; Sakai et al, 1988); β-Interferon—poly(rl) x/poly(rc) (Tavernier et al, 1983); Adenovirus 5 E2—EIA (Imperiale et al, 1984); Collagenase—Phorbol Ester (TPA) (Angel et al, 1987a); Stromelysin—Phorbol Ester (TPA) (Angel et al, 1987b); SV40—Phorbol Ester (TPA) (Angel et al, 1987b); Murine MX Gene—Interferon, Newcastle Disease Virus (Hug et al, 1988); GRP78 Gene—A23187 (Resendez et al, 1988); α-2-Macroglobulin—IL-6 (Kunz et al, 1989); Vimentin—Serum (Rittling et al, 1989); MHC Class I Gene H-2κb—Interferon (Blanar et al, 1989); HSP70—E1A/SV40 Large T Antigen (Taylor et al, 1989, 1990a, 1990b); Proliferin—Phorbol Ester/TPA (Mordacq et al, 1989); Tumor Necrosis Factor—PMA (Hensel et al, 1989); and Thyroid Stimulating Hormonea Gene—Thyroid Hormone (Chatterjee et al, 1989).

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells.

Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred— these inter alia (i.a.) allows that cell lines comprised of transformed cells as defined herein may be established— such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps.*

*fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5a, JMI 09, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by Agrobacterium mediated transformation (U.S. Pat. Nos. 5,591,616 and 5,563,055, each incorporated herein by reference); or by PEG mediated transformation of protoplasts (Omirulleh et al, 1993; U.S. Pat. Nos. 4,684,611 and 4,952,500, each incorporated herein by reference); by desiccation/inhibition mediated DNA uptake (Potrykus et al, 1985). Through the application of techniques such as these, organelle(s), cell(s), tissue(s) or organism(s) may be stably or transiently transformed.

The Antibodies of the Invention—and their Production/Isolation

Antibodies directed against the proteins of the invention are useful for affinity chromatography, immunoassays, and for distinguishing/identifying *staphylococcus* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4 C for 2-18 hours. The serum is recovered by centrifugation (e.g. 1,000 g for 10 minutes). About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (e.g. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 125I), electron-dense reagents, enzymes, and ligands having specific binding partners. Enzymes are typically detected by their activity. For example, horseradish peroxidase is usually detected by its ability to convert 3,3', 5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 1151 may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 125I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an F(ab')$_2$, an scFV; cf. also the definition of the term "antibody" presented above.

Compositions of the Invention; Vaccines

Pharmaceutical compositions, in particular vaccines, according to the invention may either be prophylactic (i.e. to prevent infection) or therapeutic (i.e. to treat disease after infection).

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+ CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc.), interferons (e.g. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (e.g. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 μg and 500 mg (however, often not higher than 5,000 μg), and very often in the range between 10 and 200 μg.

The immunogenic compositions are conventionally administered parenterally, e.g. by injection, either subcutaneously, intramuscularly, or transdermally/transcutaneously (e.g. WO98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [e.g. Robinson & Torres (1997) Seminars in Immunol 9: 271-283; Donnelly et al. (1997) Avnu Rev Immunol 15: 617-648; later herein].

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 µg of the polypeptide of the invention per administration.

In preferred embodiments of the sixth aspect, the immunization scheme includes that the animal (e.g. the human) receives a priming administration and one or more booster administrations.

Preferred embodiments of the $6^{th}$ aspect of the invention comprise that the administration is for the purpose of inducing protective immunity against S. aureus. In this embodiment it is particularly preferred that the protective immunity is effective in reducing the risk of attracting infection with S. aureus or is effective in treating or ameliorating infection with S. aureus.

As mention herein, the preferred vaccines of the invention induce humoral immunity, so it is preferred that the administration is for the purpose of inducing antibodies specific for S. aureus and wherein said antibodies or B-lymphocytes producing said antibodies are subsequently recovered from the animal.

But, as also mentioned the method of the $6^{th}$ aspect may also be useful in antibody production, so in other embodiments the administration is for the purpose of inducing antibodies specific for S. aureus and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claim, the invention also relates to related embodiments to the treatment and prophylaxis disclosed herein: the invention also includes embodiments where

- the polypeptide of the invention is for use as a pharmaceutical, in particular for use as a pharmaceutical in the treatment, prophylaxis or amelioration of infection with S. aureus;
- the nucleic acid fragment of the invention or the vector of the invention is for use as a pharmaceutical, in particular for use as a pharmaceutical in the treatment, prophylaxis or amelioration of infection with S. aureus;
- the transformed cell of the invention is for use as a pharmaceutical, in particular for use as a pharmaceutical in the treatment, prophylaxis or amelioration of infection with S. aureus.
- the antibody, antibody fragment or antibody analogue of the invention is for use as a pharmaceutical, in particular for use as a pharmaceutical in the treatment, prophylaxis or amelioration of infection with S. aureus.

EXAMPLE

Protocol for Testing S. aureus Derived Vaccines in Mice

Expression and Purification of S. aureus Genes

1. Gene fragments that encode the selected S. aureus polypeptides of the invention are prepared synthetically and are introduced into the pQE-1 vector (Qiagen) from Genscript. The fragments are inserted by blunt ended ligation into the PVU II site in the 5'-end, immediately following the vector's coding region for the 6 histidinyl residues. In the 3'-end, all inserted gene fragments include a stop codon.

2. The vectors from 1 are transfected into the E. Coli M15[pREP4] strain, which contains an expression as well as a repressor plasmid facilitating proper expression.

3. The vectors from 1 are further inserted into the E. coli XL1 Blue for long-time storage.

4. The transfected and selected clones are tested for expression in small scale whereby optimum conditions for expression in terms of the amount of IPTG, the density of cells and the time of expression induction are determined.

5. From the information obtained in 4, large scale cultures are established; subsequently the expression products are harvested and purified on a Ni-NTA column.

6. Purity and yield of the large-scale expression is investigated by means of SDS-PAGE and spectrophotometry, whereafter the proteins are aliquoted for use in immunization experiments and other experiments.

Immunization and *S. aureus* Challenge Infection in Mice (Zhou et al. 2006 Vaccine 24. 4830-4837)

1. 2 months old NMRI mice were used.
2. Groups of 8 mice (unless other numbers are indicated) were used for immunization. The mice were immunized 3 times (at day 0, 14, and 28) prior to challenge infection. A control group of 8 mice was treated according to an identical protocol with the exception that an irrelevant protein antigen was used for immunization.

1st Immunization:

50 µg protein (per mice) was mixed with 100 µl aluminum hydroxide (Alhydrogel 2.0%, Brenntag) per 125 µg protein and incubated with end-over-end rotation for 15 min. Freund's incomplete adjuvant (sigma) was added in the volume 1:1 and the mixture was vortexed thoroughly for 1 hour. This mixture was injected subcutaneously 2nd and 3rd Immunization The mice were booster injected intraperitoneally with 2 weeks interval, using the same amount of protein mixed with aluminum hydroxide and physiological saline solution.

3. One week after the last immunization 250 µl blood is drawn from the mice in order to determine the antibody titer.
4. 14 days after the last immunization, a number of bacteria ($2 \times 10^9$ cells) corresponding to a predetermined $LD_{90}$ in the control group of mice was administered intraperitoneally to all mice.

The cells were handled cold and kept on ice until use. The stock solution of MRSA cells were thawed on ice and then the appropriate amount of cells in sterile physiological saline (total volume per mouse 500 µl).

The survival was surveilled twice daily in the first 48 hours after challenge and once daily in the subsequent 7 days. The mice were sacrificed if they showed signs of suffering. The mice were monitored with respect to loss of weight and body temperature using an implanted chip. The organs of the mice were used for determination of CFU counts.

Test of Antibody Titer

Maxisorp microtiter plates (Nunc, Roskilde, Denmark) were coated overnight with 1 µg/ml recombinant peptide (His-tagged SAR-protein), 100 µl/well.

The next day the plates were emptied and washed 3 times in PBS-Tw. After the last wash the plates were allowed to stand in PBS-Tw for a minimum of 15 minutes (blocking step).

EDTA plasma was diluted 1:100 in PBS-Tw and 200 µl was added to the first well. 100 µl of washing buffer was added to all of the other wells.

A 2-fold dilution was made by transferring 100 ml from the first well to the next, and so on. The plates were incubated at room temperature for 2 hours with shaking.

The plates were washed and 100 µl of secondary antibody was added per well (e.g. HRP conjugated polyclonal rabbit anti-mouse immunoglobulin) and then incubated for 1 hour at room temperature with shaking.

The plates were washed and the ELISA developed.

The optical density value was used to calculate the antibody titer: [1/Dilution at ½ max absorbance].

Buffers used were:
Coating buffer: 15 mM $Na_2CO_3$, 35 mM $NaHCO_3$
PBS-Tw: PBS, 0.05% Tween-20 pH 7.4
Coloring buffer for developing the ELISA: 7.3 g citric add, 11.86 g $NaHPO_4$ pH 5.0 at 1 L. OPD tablets (KemEn-Tec, Diagnostic) were added, 2 mg per 5 ml coloring buffer. Immediately before use, 2 ml of 35% $H_2O_2$ was added per tablet. 100 ml of the mixed coloring substrate was added to each well. The reaction was stopped with 100 ml 1M $H_2SO_4$.

Result of Challenge Studies

The polypeptides used in the challenge studies described are in the following section setting forth the results provided with identification numbers in the format "SARXXXX". For easy reference, these polypeptides relate to the SEQ ID NOs used herein according to the following table:

| SEQ ID 1: | SAR2104 | SEQ ID 2: | SAR1879 |
|---|---|---|---|
| SEQ ID 3: | SAR0730 | SEQ ID 4: | SAR2722 |
| SEQ ID 5: | SAR1507 | SEQ ID 6: | SAR0222 |
| SEQ ID 7: | SAR1558 | SEQ ID 8: | SAR1026 |
| SEQ ID 9: | SAR1489 | SEQ ID 10: | SAR1819 |
| SEQ ID 11: | SAR0826 | SEQ ID 12: | SAR0390 |
| SEQ ID 13: | SAR0280 | SEQ ID 14: | SAR1816 |
| SEQ ID 15: | SAR0992 | SEQ ID 16: | SAR1881 |
| SEQ ID 17: | SAR0735 | SEQ ID 18: | SAR2119 |
| SEQ ID 19: | SAR2184 | | |

The challenge study gave the following results in term of overall survival in the vaccinated groups vs. the control groups:

| Vaccine protein | Percentage of mice surviving at end of experiment | |
|---|---|---|
| | Vaccinated mice | Control control group |
| SAR2104-20-154 | 50% | 0% |
| SAR0280-28-820 | 75% | 0% |
| SAR0390-21-190 | 0% | 0% |
| SAR2104-20-154 | 25% | 0%* |
| SAR1879-24-184 | 14%* | 0%* |
| SAR0222-27-609 | 13% | 0%* |
| SAR1881-25-208 | 13% | 0%* |
| SAR2119-34-370 | 25% | 0%* |
| SAR0872-27-273 | 29%* | 0%* |
| SAR2718-24-157 | 17%** | 0%* |
| SAR1816-1-27 | 67%** | 0% (50%) |
| SAR0735-26-227 | 88% | 0% (50%) |
| SAR0992-428-769 | 29%* | 0% (50%) |
| SAR1816-46-396 | 63% | 0% (50%) |
| 1:1:1 Mixture of SAR2104-20-154 SAR0280-28-820 SAR0872-27-273 | 88%# | 0%# |
| SAR0826-42-209 | 0% | (13%) |
| SAR0992-1-409 | 100% | (13%) |
| SAR1489-343-486 | 75% | (13%) |
| SAR1507-1-652 | 88% | (13%) |
| SAR1558-21-144 | 38% | (10%) |
| SAR0730-22-129 | 100%* | (13%) |
| SAR1819-1-1274 | 88% | (13%) |
| SAR2722-920-948 | 63% | (13%) |
| SAR1972-23-91 | 50% | (13%) |
| SAR2104-20-154_nativ | 63% | (13%) |
| SAR0280-28-820_nativ | 63% | (13%) |

*7 mice in group
**6 mice in group
16 mice in group

Percentages in parentheses in control group column indicate survival rate in control group, where mice received injection with adjuvant mixture. Percentages without parentheses in control group column indicate survival rate in control group, where mice received saline only.

Results of ELISA Tests

The tables set forth on the following pages show the OD measurements and, where applicable, in vaccinated mice from the different treatment groups:

Test protein: SAR 2104-20-154

| ELISA Plate ID | Mouse No | Bleed Bleed # | \multicolumn{12}{c}{Sera dilution (OD490 nm)} | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| Juni 2104 | 18 | 3 | 4 | 4 | 4 | 3.777 | 3.441 | 2.735 | 1.958 | 1.293 | 0.733 | 0.428 | 0.246 | 0.12 |
| Juni 2104 | 20 | 3 | 4 | 4 | 4 | 4 | 3.789 | 3.282 | 2.436 | 1.6 | 0.979 | 0.547 | 0.262 | 0.121 |
| Juni 2104 | 22 | 3 | 3.894 | 3.892 | 3.897 | 3.871 | 3.544 | 3.122 | 2.573 | 2.006 | 1.383 | 0.841 | 0.481 | 0.252 |
| Juni 2104 | 24 | 3 | 4 | 4 | 4 | 4 | 3.719 | 3.025 | 2.07 | 1.357 | 0.825 | 0.487 | 0.265 | 0.138 |
| Juni 2104 | 25 | 3 | 4 | 4 | 4 | 3.86 | 3.453 | 2.824 | 2.089 | 1.497 | 0.896 | 0.516 | 0.29 | 0.156 |
| Juni 2104 | 27 | 3 | 4 | 4 | 3.875 | 3.667 | 3.181 | 2.445 | 1.644 | 1.037 | 0.598 | 0.332 | 0.175 | 0.095 |
| Juni 2104 | 29 | 3 | 4 | 4 | 4 | 4 | 3.588 | 2.656 | 1.765 | 1.049 | 0.588 | 0.319 | 0.176 | 0.089 |
| Juni 2104 | 31 | 3 | 4 | 4 | 3.894 | 3.689 | 3.043 | 2.225 | 1.52 | 1.034 | 0.614 | 0.347 | 0.193 | 0.101 |

Test protein: SAR 0280-28-820

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| juni 280 | 60 | 3 | 4 | 4 | 4 | 3.777 | 3.441 | 2.735 | 1.958 | 1.293 | 0.733 | 0.428 | 0.246 | 0.12 |
| juni 280 | 61 | 3 | 4 | 4 | 4 | 4 | 3.789 | 3.282 | 2.436 | 1.6 | 0.979 | 0.547 | 0.262 | 0.121 |
| juni 280 | 62 | 3 | 3.894 | 3.892 | 3.897 | 3.871 | 3.544 | 3.122 | 2.573 | 2.006 | 1.383 | 0.841 | 0.481 | 0.252 |
| juni 280 | 63 | 3 | 4 | 4 | 4 | 4 | 3.719 | 3.025 | 2.07 | 1.357 | 0.825 | 0.487 | 0.265 | 0.138 |
| juni 280 | 64 | 3 | 4 | 4 | 4 | 3.86 | 3.453 | 2.824 | 2.089 | 1.497 | 0.896 | 0.516 | 0.29 | 0.156 |
| juni 280 | 65 | 3 | 4 | 4 | 3.875 | 3.667 | 3.181 | 2.445 | 1.644 | 1.037 | 0.598 | 0.332 | 0.175 | 0.095 |
| juni 280 | 66 | 3 | 4 | 4 | 4 | 4 | 3.588 | 2.656 | 1.765 | 1.049 | 0.588 | 0.319 | 0.176 | 0.089 |
| juni 280 | 67 | 3 | 4 | 4 | 3.894 | 3.689 | 3.043 | 2.225 | 1.52 | 1.034 | 0.614 | 0.347 | 0.193 | 0.101 |

Test protein: SAR 0390-21-190

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| juni 0390* | 50 | 3 | 4 | 4 | 4 | 4 | 3.593 | 2.83 | 1.979 | 1.253 | 0.714 | 0.389 | 0.208 | 0.121 |
| juni 0390** | 51 | 3 | 4 | 4 | 4 | 3.925 | 3.627 | 2.731 | 1.785 | 1.053 | 0.574 | 0.296 | 0.155 | 0.081 |
| juni 0390 | 52 | 3 | 4 | 4 | 4 | 4 | 3.516 | 2.709 | 1.86 | 1.11 | 0.627 | 0.333 | 0.182 | 0.095 |
| juni 0390 | 53 | 3 | 4 | 4 | 4 | 4 | 3.753 | 3.297 | 2.379 | 1.538 | 0.917 | 0.502 | 0.278 | 0.15 |
| juni 0390 | 54 | 3 | 4 | 4 | 4 | 4 | 3.865 | 3.446 | 2.648 | 1.799 | 1.077 | 0.6 | 0.337 | 0.163 |
| juni 0390 | 55 | 3 | 4 | 4 | 4 | 4 | 3.931 | 3.907 | 3.544 | 2.769 | 1.844 | 1.107 | 0.612 | 0.316 |
| juni 0390 | 56 | 3 | 4 | 4 | 4 | 3.864 | 3.396 | 2.59 | 1.715 | 1.043 | 0.584 | 0.317 | 0.173 | 0.093 |
| juni 0390 | 57 | 3 | 4 | 3.931 | 4 | 3.841 | 3.233 | 2.309 | 1.443 | 0.83 | 0.45 | 0.234 | 0.123 | 0.067 |

Test protein: SAR0222-27-609

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| 222 | 0Ø | 3 | 3.899 | 3.646 | 3.306 | 2.755 | 2.035 | 1.351 | 0.806 | 0.485 | 0.289 | 0.177 | 0.098 | 0.06 |
| 222 | BØ | 3 | 3.011 | 2.854 | 2.518 | 1.964 | 1.485 | 0.969 | 0.607 | 0.375 | 0.243 | 0.128 | 0.077 | 0.04 |
| 222 | VØ | 3 | 3.669 | 3.294 | 2.737 | 1.98 | 1.314 | 0.784 | 0.451 | 0.268 | 0.175 | 0.098 | 0.063 | 0.034 |
| 222 | HØ | 3 | 3.535 | 3.375 | 3.24 | 2.814 | 2.317 | 1.824 | 1.466 | 1.166 | 0.889 | 0.576 | 0.344 | 0.185 |
| 222 | 20Ø | 3 | 3.055 | 2.927 | 2.803 | 2.498 | 1.949 | 1.513 | 1.087 | 0.756 | 0.481 | 0.283 | 0.157 | 0.086 |

-continued

| | | | Test protein: SAR0222-27-609 | | | | | | | | | | |
|---|---|---|---|---|---|---|---|---|---|---|---|---|---|
| ELISA | Mouse | Bleed | Sera dilution (OD490 nm) | | | | | | | | | | |
| Plate ID | No | Bleed # | 100 | 200 | 400 | 800 | 1600 | 3200 | 6400 | 12800 | 25600 | 51200 | 102400 | 204800 |
| 222 | 2BØ | 3 | 2.568 | 2.281 | 1.871 | 1.331 | 0.84 | 0.471 | 0.267 | 0.145 | 0.084 | 0.049 | 0.029 | 0.017 |
| 222 | 2HØ | 3 | 4 | 3.816 | 3.646 | 3.093 | 2.389 | 1.66 | 1.033 | 0.628 | 0.415 | 0.25 | 0.143 | 0.077 |
| 222 | 2VØ | 3 | 4 | 3.827 | 3.552 | 3.05 | 2.385 | 1.665 | 1.065 | 0.642 | 0.365 | 0.203 | 0.127 | 0.062 |

| | | | Test protein: SAR0872-27-273 | | | | | | | | | | |
|---|---|---|---|---|---|---|---|---|---|---|---|---|---|
| ELISA | Mouse | Bleed | Sera dilution (OD490 nm) | | | | | | | | | | |
| Plate ID | No | Bleed # | 100 | 200 | 400 | 800 | 1600 | 3200 | 6400 | 12800 | 25600 | 51200 | 102400 | 204800 |
| 0872 | 2 | 3 | 4 | 4 | 4 | 4 | 4 | 4 | 4 | 4 | 4 | 3.564 | 2.528 | 1.57 |
| 0872 | 4 | 3 | 4 | 4 | 4 | 4 | 4 | 4 | 4 | 3.944 | 3.476 | 2.441 | 1.561 | 0.917 |
| 0872 | 6 | 3 | 4 | 4 | 4 | 4 | 4 | 4 | 4 | 4 | 3.931 | 3.367 | 2.446 | 1.57 |
| 0872 | 8 | 3 | 4 | 4 | 4 | 4 | 4 | 4 | 4 | 4 | 4 | 3.777 | 2.732 | 1.739 |
| 0872 | 17 | 3 | 4 | 4 | 4 | 4 | 4 | 4 | 4 | 4 | 3.724 | 2.838 | 1.913 | 1.158 |
| 0872 | 19 | 3 | 4 | 4 | 4 | 4 | 4 | 4 | 4 | 3.786 | 3.121 | 2.237 | 1.409 | 0.811 |
| 0872 | 21 | 3 | 4 | 4 | 4 | 4 | 4 | 4 | 4 | 4 | 3.566 | 2.552 | 1.615 | 0.901 |
| 0872 | 23 | 3 | 4 | 4 | 4 | 4 | 4 | 4 | 4 | 4 | 3.887 | 3.269 | 2.251 | 1.404 |

| | | | Test protein: SAR1879-24-184 | | | | | | | | | | |
|---|---|---|---|---|---|---|---|---|---|---|---|---|---|
| ELISA | Mouse | Bleed | Sera dilution (OD490 nm) | | | | | | | | | | |
| Plate ID | No | Bleed # | 100 | 200 | 400 | 800 | 1600 | 3200 | 6400 | 12800 | 25600 | 51200 | 102400 | 204800 |
| 1879 | 0Ø | 3 | 4 | 4 | 4 | 4 | 4 | 4 | 4 | 3.871 | 3.028 | 2.038 | 1.228 | 0.662 |
| 1879 | VØ | 3 | 4 | 4 | 4 | 4 | 4 | 4 | 3.508 | 2.428 | 1.548 | 0.881 | 0.478 | 0.242 |
| 1879 | HØ | 3 | 4 | 4 | 4 | 4 | 4 | 4 | 3.665 | 2.686 | 1.778 | 1.041 | 0.577 | 0.301 |
| 1879 | 20Ø | 3 | 4 | 4 | 4 | 4 | 4 | 4 | 3.501 | 2.468 | 1.548 | 0.856 | 0.474 | 0.244 |
| 1879 | 2BØ | 3 | 4 | 4 | 4 | 4 | 4 | 3.872 | 3.175 | 2.12 | 1.333 | 0.747 | 0.406 | 0.213 |
| 1879 | 2VØ | 3 | 4 | 4 | 4 | 4 | 4 | 4 | 3.52 | 2.453 | 1.483 | 0.821 | 0.428 |
| 1879 | 2HØ | 3 | 4 | 4 | 4 | 4 | 4 | 3.885 | 3.363 | 2.325 | 1.452 | 0.826 | 0.448 | 0.224 |

| | | | Test protein: SAR1881-25-208 | | | | | | | | | | |
|---|---|---|---|---|---|---|---|---|---|---|---|---|---|
| ELISA | Mouse | Bleed | Sera dilution (OD490 nm) | | | | | | | | | | |
| Plate ID | No | Bleed # | 100 | 200 | 400 | 800 | 1600 | 3200 | 6400 | 12800 | 25600 | 51200 | 102400 | 204800 |
| 1881 | 0Ø | 3 | 4 | 4 | 3.66 | 3.06 | 2.238 | 1.454 | 0.848 | 0.47 | 0.251 | 0.135 | 0.078 | 0.047 |
| 1881 | BØ | 3 | 4 | 4 | 3.558 | 2.546 | 1.551 | 0.884 | 0.481 | 0.26 | 0.137 | 0.075 | 0.048 | 0.032 |
| 1881 | VØ | 3 | 4 | 4 | 3.78 | 2.952 | 1.888 | 1.105 | 0.617 | 0.335 | 0.181 | 0.102 | 0.058 | 0.039 |
| 1881 | HØ | 3 | 4 | 3.595 | 2.644 | 1.678 | 0.983 | 0.546 | 0.3 | 0.162 | 0.091 | 0.053 | 0.035 | 0.026 |
| 1881 | 20Ø | 3 | 4 | 4 | 4 | 4 | 3.583 | 3.018 | 2.231 | 1.454 | 0.866 | 0.478 | 0.258 | 0.141 |
| 1881 | 2BØ | 3 | 1.195 | 0.577 | 0.316 | 0.171 | 0.101 | 0.064 | 0.044 | 0.032 | 0.027 | 0.022 | 0.022 | 0.019 |
| 1881 | 2VØ | 3 | 4 | 3.792 | 3.313 | 2.508 | 1.716 | 1.024 | 0.598 | 0.333 | 0.181 | 0.1 | 0.06 | 0.039 |
| 1881 | 2HØ | 3 | 0.995 | 0.559 | 0.3 | 0.165 | 0.097 | 0.061 | 0.043 | 0.033 | 0.026 | 0.02 | 0.019 | 0.02 |

| | | | Test protein: SAR2104-20-154 | | | | | | | | | | |
|---|---|---|---|---|---|---|---|---|---|---|---|---|---|
| ELISA | Mouse | Bleed | Sera dilution (OD490 nm) | | | | | | | | | | |
| Plate ID | No | Bleed # | 100 | 200 | 400 | 800 | 1600 | 3200 | 6400 | 12800 | 25600 | 51200 | 102400 | 204800 |
| 2104 | 0Ø | 3 | 4 | 4 | 4 | 4 | 4 | 4 | 3.841 | 3.033 | 2.031 | 1.197 | 0.674 | 0.371 |
| 2104 | BØ | 3 | 0.67 | 0.377 | 0.22 | 0.138 | 0.089 | 0.067 | 0.052 | 0.048 | 0.044 | 0.042 | 0.041 | 0.04 |
| 2104 | VØ | 3 | 0.276 | 0.165 | 0.099 | 0.073 | 0.057 | 0.053 | 0.047 | 0.045 | 0.043 | 0.042 | 0.041 | 0.039 |

-continued

Test protein: SAR2104-20-154

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| 2104 | 2OØ | 3 | 0.153 | 0.099 | 0.071 | 0.057 | 0.048 | 0.047 | 0.043 | 0.043 | 0.044 | 0.042 | 0.041 | 0.039 |
| 2104 | 2BØ | 3 | 0.458 | 0.378 | 0.285 | 0.244 | 0.2 | 0.169 | 0.135 | 0.099 | 0.07 | 0.052 | 0.047 | 0.043 |
| 2104 | 2VØ | 3 | 0.349 | 0.25 | 0.178 | 0.133 | 0.098 | 0.09 | 0.067 | 0.041 | 0.046 | 0.043 | 0.042 | 0.039 |
| 2104 | 2HØ | 3 | 0.345 | 0.221 | 0.142 | 0.103 | 0.074 | 0.06 | 0.051 | 0.047 | 0.044 | 0.041 | 0.042 | 0.037 |

Test protein: SAR2119-34-370

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| 2119 | OØ | 3 | 4 | 4 | 4 | 3.857 | 4 | 4 | 3.689 | 3.27 | 1.839 | 1.121 | 0.597 | 0.311 |
| 2119 | BØ | 3 | 4 | 4 | 4 | 4 | 4 | 4 | 3.872 | 3.379 | 2.373 | 1.49 | 0.827 | 0.434 |
| 2119 | VØ | 3 | 4 | 4 | 3.949 | 4 | 4 | 4 | 3.892 | 3.218 | 2.22 | 1.339 | 0.751 | 0.381 |
| 2119 | HØ | 3 | 0.187 | 0.101 | 0.168 | 0.102 | 0.062 | 0.041 | 0.03 | 0.022 | 0.017 | 0.017 | 0.015 | 0.011 |
| 2119 | 2OØ | 3 | 4 | 4 | 4 | 4 | 3.421 | 2.446 | 1.457 | 0.819 | 0.439 | 0.228 | 0.122 | 0.063 |
| 2119 | 2BØ | 3 | 4 | 4 | 4 | 4 | 4 | 4 | 4 | 3.594 | 2.695 | 1.747 | 1.026 | 0.547 |
| 2119 | 2VØ | 3 | 4 | 4 | 4 | 4 | 3.577 | 2.731 | 1.734 | 1.012 | 0.552 | 0.285 | 0.146 | 0.076 |
| 2119 | 2HØ | 3 | 4 | 4 | 4 | 4 | 3.498 | 2.52 | 1.521 | 0.874 | 0.466 | 0.244 | 0.128 | 0.066 |

Test protein: SAR2718-24-157

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| 2718 | OØ | 3 | 4 | 4 | 4 | 4 | 4 | 3.906 | 3.27 | 2.491 | 1.673 | 1.062 | 0.616 | 0.323 |
| 2718 | VØ | 3 | 3.923 | 4 | 4 | 3.786 | 3.09 | 2.101 | 1.238 | 0.682 | 0.366 | 0.19 | 0.105 | 0.057 |
| 2718 | HØ | 3 | 4 | 4 | 4 | 4 | 4 | 3.944 | 3.498 | 2.547 | 1.622 | 0.963 | 0.514 | 0.27 |
| 2718 | 2OØ | 3 | 4 | 4 | 4 | 4 | 3.944 | 2.971 | 1.885 | 0.966 | 0.449 | 0.187 | 0.086 | 0.047 |
| 2718 | 2BØ | 3 | 4 | 4 | 3.885 | 3.344 | 3.204 | 1.371 | 0.773 | 0.402 | 0.216 | 0.115 | 0.06 | 0.037 |
| 2718 | 2VØ | 3 | 4 | 4 | 4 | 4 | 3.801 | 2.893 | 1.911 | 1.17 | 0.632 | 0.349 | 0.174 | 0.091 |
| 2718 | 2HØ | 3 | 4 | 4 | 4 | 3.726 | 3.229 | 1.844 | 1.104 | 0.595 | 0.324 | 0.174 | 0.093 | 0.051 |

Test protein: SAR0826-42-209

| ELISA Plate ID | Mouse No | Bleed Bleed # | Sera dilution (OD490 nm) | | | | | | | | | | | |
|---|---|---|---|---|---|---|---|---|---|---|---|---|---|---|
| | | | 100 | 200 | 400 | 800 | 1600 | 3200 | 6400 | 12800 | 25600 | 51200 | 102400 | 204800 |
| 0826 | 1 | 3 | −0.0058 | −0.0288 | −0.0138 | −0.0258 | −0.0128 | −0.0288 | 0.0132 | 0.0062 | −0.0688 | −0.0098 | −0.0398 | −0.0178 |
| 0826 | 2 | 3 | 0.2672 | −0.0188 | −0.0668 | −0.0888 | −0.1188 | −0.1038 | −0.1288 | −0.1168 | −0.1188 | −0.1068 | −0.0698 | 0.3492 |
| 0826 | 3 | 3 | −0.0828 | −0.1518 | −0.1278 | −0.1308 | −0.1268 | −0.1168 | −0.1288 | −0.1338 | −0.0558 | −0.1118 | −0.0968 | −0.0378 |
| 0826 | 4 | 3 | −0.0918 | −0.1458 | −0.1308 | −0.1448 | −0.1408 | −0.1318 | −0.1518 | −0.1398 | −0.1328 | −0.1168 | −0.1068 | −0.0588 |
| 0826 | 5 | 3 | 0.0922 | −0.1228 | −0.1448 | −0.1438 | −0.1168 | −0.1198 | −0.0918 | −0.1388 | −0.1288 | −0.1138 | −0.1228 | −0.0908 |
| 0826 | 6 | 3 | 1.1902 | 0.4132 | 0.0792 | −0.0518 | −0.1048 | −0.1448 | −0.1378 | −0.1568 | −0.1378 | −0.1168 | −0.1168 | −0.0678 |
| 0826 | 7 | 3 | 3.1572 | 2.6172 | 1.6322 | 0.8702 | 0.3652 | 0.1352 | −0.0218 | −0.0928 | −0.0928 | −0.0988 | −0.0948 | −0.0718 |
| 0826 | 8 | 3 | −0.1568 | −0.1638 | −0.1168 | −0.1198 | −0.0238 | 0.0102 | −0.0388 | −0.0828 | −0.0818 | −0.0618 | −0.0368 | −0.0038 |

Immune Fluorescence/FACS Analyses of Plasma Samples from Immunized Mice

1. Groups of mice will be immunized three times with intervals of 14 days with antigen coupled onto carrier-proteins, diphtheria-toxoid and/or secreted mycobacterial proteins (PPD). All immunizations are carried out subcutaneously with the antigen adsorbed onto Al(OH)$_3$ and with Freunds incomplete adjuvant, cf. above.

2. A control group of mice are immunized with diphtheria-toxoid without antigen.

3. Mice are bled after the second and the third immunization.

4. The serum bleeds are tested for their reactivity against the immunizing antigen.

5. The following methods will be used:

Direct measurement of antibodies to the immunizing antigen

Analysis for agglutinating power when antibodies are incubated with the bacteria Analysis for killing effect on bacteria after incubation of bacteria with antiserum+fresh serum (complement)

Proteins of the Invention

The *S. aureus* proteins of the present invention are set forth in the sequence listing together with their related nucleic acid sequences. For easy reference, the one letter amino acid sequences of the *S. aureus* proteins are provided in the following:

```
SEQ ID NO: 1:
MKRLLGLLLVSTLVLSACGNDENQEESKKEVKSKEKKIEKEKENKSKKDKEKEVATQQQPDNQTVEQPQ

SQEQSVQQPQQQIPQNSVPQQNVQVQQNKKQKVDLNNMPPTDFSTEGMSEQAQKQIEELSMQKDYHG

LSQREYNDRVSEIINNDN

SEQ ID NO: 2:
MLKGCGGCLISFIILIILLSACSMMFSNNDNSTSNQSSKTQLTQKDEDKSENMPEEKSESETDKDLQSTE

EVPANENTENNQHEIDEITTTDQSDDEINTPNVAEEESQDDLKDDLKEKQQPSDHHQSTQPKTSPSTETN

KQQSFANCKQLRQVYPNGVTADHPAYRPHLDRDKDKRACEPDKY

SEQ ID NO: 3:
MKKLIISIMAIMLFLTGCGKSQEKATLEKDIDNLQKENKELKDKKEKLQQEKEKLADKQKDLEKEVKDLKP

SKEDNKDDKKDEDKNKDKDKEASQDKQSKDQTKSSDKDNHKKPTSTDKDQKANDKHQS

SEQ ID NO: 4:
MKNAFKLFKMDLKKVAKTPAVWIILAGLAILPSFYAWFNLWAMWDPYGNTGHIKVAVVNEDKGDTIRGK

KVNVGNTMVNTLKKNKSFDWQFVSREKADHEIKMGKYFAGIYIPSKFTHEITGTLRKQPQKADVEFKVNQ

KINAVASKLTDTGSSVVVEKANEQFNKTVTRALLEEANKAGLTIEENVPTINKIKNAVYSADKALPKINDFA

NKIVYLNNHQADLDKYANDFRKLGNYKGDILDAQKKLNEVNGAIPQLNEKAKLILALNNYMPKIEKALNFA

ADDVPAQFPKINQGLNIASQGIDQANGQLNDAKGFVTQVRSRVGDYQEAIRRAQDLNRRNQQQIPQNS

AANNETSNSAPAAGNGVTSTPPSAPNGNTIPNNNVTQNTAPNSNNAPVSTTPQSTSGKKDGQSFADITT

TQVSTANENTQNITDKDVKSMEAALTGSLLSLSNNLDTQAKAAQKDSQALRNISYGILASDKPSDFRESL

DNVKSGLEYTTQYNQQFIDTLKEIEKNENVDLSKEIDKVKTANNRINESLRLVNQLSNALKNGSSGTAEAT

KLLDQLSKLDSSLSSFRDYVKKDLNSSLVSISQRIMDELNKGQTALSNVQSKLNTIDQVINSGQSILKNG

KTRIDRLQTVLPSIEQQYISAIKNAQANFPKVKSDVAKAANFVRNDLPQLEQRLTNATASVNKNLPTLLNG

YDQAVGLLNKNQPQAKKALSDLADFAQNKLPDVEKDLKKANKIFKKLDKDDAVDKLIDTLKNDLKKQAGI

IANPINKKTVDVFPVKDYGSGMTPFYTALSVWVGALLMVSLLTVDNKHKSLEPVLTTRQVFLGKAGFFIML

GMLQALIVSVGDLLILKAGVESPVLFVLITIFCSIIFNSIVYTCVSLLGNPGKAIAIVLLVLQIAGGGGTFPIQT

TPQFFQNISPYLPFTYAIDSLRETVGGIVPEILITKLIILTLFGIGFFVVGLILKPVTDPLMKRVSEKVDQSNVT

E

SEQ ID NO: 5:
MNEKVEGMTLELKLDHLGVQEGMKGLKRQLGVVNSEMKANLSAFDKSEKSMEKYQARIKGLNDRLKVQ

KKMYSQVEDELKQVNANYQKAKSSVKDVEKAYLKLVEANKKEKLALDKSKEALKSSNTELKKAENQYKR

TNQRKQDAYQKLKQLRDAEQKLKNSNQATTAQLKRASDAVQKQSAKHKALVEQYKQEGNQVQKLKVQ

NDNLSKSNDKIESSYAKTNTKLKQTEKEFNDLNNTIKNHSANVAKAETAVNKEKAALNNLERSIDKASSE

MKTFNKEQMIAQSHFGKLASQADVMSKKFSSIGDKMTSLGRTMTMGVSTPITLGLGAALKTSADFEGQM

SRVGAIAQASSKDLKSMSNQAVDLGAKTSKSANEVAKGMEELAALGFNAKQTMEAMPGVISAAEASGAE

MATTATVMASAINSFGLKASDANHVADLLARSANDSAADIQYMGDALKYAGTPAKALGVSIEDTSAAIEV

LSNSGLEGSQAGTALRASFIRLANPSKNTAKEMKKLGIHLSDAKGFVGMGELIRQFQDNMKGMTREQK

LATVATIVGTEAASGFLALIEAGPDKINSYSKSLKNSNGESKKAADLMKDNLKGALEQLGGAFESLAIEVG

KDLTPMIRAGAEGLTKLVDGFTHLPGWVRKASVGLALFGASIGPAVLAGGLLIRAVGSAAKGYASLNRRIA
```

-continued

ENTILSNTNSKAMKSLGLQTLFLGSTTGKTSKGFKGLAGAMLFNLKPINVLKNSAKLAILPFKLLKNGLGLA

AKSLFAVSGGARFAGVALKFLTGPIGATITAITIAYKVFKTAYDRVEWFRNGINGLGETIKFFGGKIIGGAV

RKLGEFKNYLGSIGKSFKEKFSKDMKDGYKSLSDDDLLKVGVNKFKGFMQTMGTASKKASDTVKVLGKG

VSKETEKALEKYVHYSEENNRIMEKVRLNSGQITEDKAKKLLKIEADLSNNLIAEIEKRNKKELEKTQELID

KYSAFDEQEKQNILTRTKEKNDLRIKKEQELNQKIKELKEKALSDGQISENERKEIEKLENQRRDITVKELS

KTEKEQERILVRMQRNRNSYSIDEASKAIKEAEKARKAKKKEVDKQYEDDVIAIKNNVNLSKSEKDKLLAI

ADQRHKDEVRKAKSKKDAVVDVVKKQNKDIDKEMDLSSGRVYKNTEKWWNGLKSWWSNFREDQKKK

SDKYAKEQEETARRNRENIKKWFGNAWDGVKSKTGEAFSKMGRNANHFGGEMKKMWSGIKGIPSKLS

SGWSSAKSSVGYHTKAIANSTGKWFGKAWQSVKSTTGSIYNQTKQKYSDASDKAWAHSKSIWKGTSK

WFSNAYKSAKGWLTDMANKSRSKWDNISSTAWSNAKSVWKGTSKWFSNSYKSLKGWTGDMYSRAH

DRFDAISSSAWSNAKSVFNGFRKWLSRTYEWIRDIGKDMGRAAADLGKNVANKAIGGLNSMIGGINKIS

KAITDKNLIKPIPTLSTGTLAGKGVATDNSGALTQPTFAVLNDRGSGNAPGGGVQEVIHRADGTFHAPQG

RDVVVPLGVGDSVINANDTLKLQRMGVLPKFHGGTKKKKWMEQVTENLGKKAGDFGSKAKNTAHNIKK

GAEEMVEAAGDKIKDGASWLGDKIGDVWDYVQHPGKLVNKVMSGLNINFGGGANATVKIAKGAYSLLK

KKLVDKVKSWFEDFGGGGDGSYLFDHPIWQRFGSYTGGLNFNGGRHYGIDFQMPTGTNIYAVKGGIAD

KVWTDYGGGNSIQIKTGANEWNWYMHLSKQLARQGQRIKAGQLIGKSGATGNFVRGAHLHFQLMQGS

HPGNDTAKDPEKWLKSLKGSGVRSGSGVNKAASAWAGDIRRAAKRMGVNVTSGDVGNIISLIQHESGG

NAGITQSSALRDINVLQGNPAKGLLQYIPQTFRHYAVRGHNNIYSGYDQLLAFFNNSYWRSQFNPRGGW

SPSGPRRYANGGLITKHQLAEVGEGDKQEMVIPLTRRKRAIQLTEQVMRIIGMDGKPNNITVNNDTSTVE

KLLKQIVMLSDKGNKLTDALIQTVSSQDNNLGSNDAIRGLEKILSKQSGHRANANNYMGGLTN

SEQ ID NO: 6:
MKKQIISLGALAVASSLFTWDNKADAIVTKDYSKESRVNENSKYDTPIPDWYLGSILNRLGDQIYYAKELT

NKYEYGEKEYKQAIDKLMTRVLGEDHYLLEKKKAQYEAYKKWFEKHKSENPHSSLKKIKFDDFDLYRLTK

KEYNELHQSLKEAVDEFNSEVKNIQSKQKDLLPYDEATENRVTNGIYDFVCEIDTLYAAYFNHSQYGHNA

KELRAKLDIILGDAKDPVRITNERIRKEMMDDLNSIIDDFFMDTNMNRPLNITKFNPNIHDYTNKPENRDN

FDKLVKETREAIANADESWKTRTVKNYGESETKSPVVKEEKKVEEPQLPKVGNQQEDKITVGTTEEAPLPI

AQPLVKIPQGTIQQEIVKGPEYLTMENKTLQGEIVQGPDFPTMEQNRPSLSDNYTQPTTPNPILKGIEGNST

KLEIKPQGTESTLKGTQGESSDIEVKPQATETTEASHYPARPQFNKTPKYVKYRDAGTGIREYNDGTFGYE

ARPRFNKPSETNAYNVTTNQDGTVSYGARPTQNKPSETNAYNVTTHANGQVSYGARPTQNKPSETNAYN

VTTHANGQVSYGARPTQNKPSKTNAYNVTTHADGTATYGPRVTK

SEQ ID NO: 7:
MKKVIGLLLVSTLALTACGEKEKPKKEENKKSQTQKHKDSKPKTQQEKMKKVEDKNPPNNSIQNNSNNQ

NQSQNNQLNNNSDPSNNTPANINKNDSQNTNLNDEYVVSPGWTKDEQAKAFEEYKKGKEDEARAGAS

AVPGANIN

SEQ ID NO: 8:
MAKKFNYKLPSMVALTLVGSAVTAHQVQAAETTQDQTTNKNVLDSNKVKATTEQAKAEVKNPTQNISGT

QVYQDPAIVQPKAANKTGNAQVNQKVDTTQVNGDTRATQSTTSNNAKPVTKSTNTTAPKTNNNVTSAG

YSLVDDEDDNSENQINPELIKSAAKPAALETQYKAAAPKATPVAPKAKTEATPKVTTFSASAQPRSAAAP

KTSLPKYKPQVNSSINDYIRKNNLKAPKIEEDYTSYFPKYAYRNGVGRPEGIVVHDTANDRSTINGEISYM

KNNYQNAFVHAFVDGDRIIETAPTDYLSWGVGAVGNPRFINVEIVHTHDYASFARSMNNYADYAATQLQ

YYGLKPDSAEYDGNGTVWTHYAVSKYLGGTDHADPHGYLRSHNYSYDQLYDLINEKYLIKMGKVAPWGT

QSTTTPTTPSKPSTPSKPSTPSTGKLTVAANNGVAQIKPTNSGLYTTVYDKTGKATNEVQKTFAVSKTATL

-continued

GNQKFYLVQDYNSGNKFGWVKEGDVVYNTAKSPVNVNQSYSIKPGTKLYTVPWGTSKQVAGSVSGSGN

QTFKASKQQQIDKSIYLYGSVNGKSGWVSKAYLVDTAKPTPTPTPKPSTPTTNNKLTVSSLNGVAQINAK

NNGLFTTVYDKTGKPTKEVQKTFAVTKEASLGGNKFYLVKDYNSPTLIGWVKQGDVIYNNAKSPVNVMQ

TYTVKPGTKLYSVPWGTYKQEAGAVSGTGNQTFKATKQQQIDKSIYLYGTVNGKSGWISKAYLAVPAAPK

KAVAQPKTAVKAYAVTKPQTTQTVSKIAQVKPNNTGIRASVYEKTAKNGAKYADRTFYVTKERAHGNETY

VLLNNTSHNIPLGWFNVKDLNVQNLGKEVKTTQKYTVNRSNNGLSMVPWGTKNQVILTGNNIAQGTFNA

TKQVSVGKDVYLYGTINNRTGWVNSKDLTAPTAVKPTTSAAKDYNYTYVIKNGNGYYYVTPNSDTAKYSL

KAFNEQPFAVVKEQVINGQTWYYGKLSNGKLAWIKSTDLAKELIKYNQIGMTLNQVAQIQAGLQYKPQV

QRVPGKWTDANFNDVKHAMDTKRLAQDPALKYQFLRLDQPQNISIDKINQFLKGKGVLENQGAAFNKAA

QMYGINEVYLISHALLETGNGTSQLAKGADVVNNKVVTNSNTKYHNVFGIAAYDNDPLREGIKYAKQAG

WDTVSKAIVGGAKFIGNSYVKAGQNTLYKMRWNPAHPGTHQYATDVDWANINAKIIKGYYDKIGEVGKY

FDIPQYK

SEQ ID NO: 9:
MSNNFKDDFEKNRQSIDTNSHQDHTEDVEKDQSELEHQDTIENTEQQFPPRNAQRRKRRRDLATNHNK

QVHNESQTSEDNVQNEAGTIDDRQVESSHSTESQEPSHQDSTPQHEEGYYNKNAFAMDKSHPEPIEDN

DKHETIKEAENNTEHSTVSDKSEAEQSQQPKPYFATGANQANTSKDKHDDVTVKQDKDESKDHHSGKK

GAAIGAGTAGVAGAAGAMGVSKAKKHSNDAQNKSNSGKVNNSTEDKASEDKSKEHHNGKKGAAIGAG

TAGLAGGAASNSASAASKPHASNNASQNNDEHDHHDRDKERKKGGMAKVLLPLIAAVLIIGALAIFGGM

ALNNHNNGTKENKIANTNKNNADESKDKDTSKDASKDKSKSTDSDKSKDDQDKATKDESDNDQNNAN

QANNQAQNNQNQQQANQNQQQQQQRQGGGQRHTVNGQENLYRIAIQYYGSGSPENVEKIRRANGLS

GNNIRNGQQIVIP

SEQ ID NO: 10:
MSWFDKLFGEDNDSNDDLIHRKKKRRQESQNIDNDHDSLLPQNNDIYSRPRGKFRFPMSVAYENENVE

QSADTISDEKEQYHRDYRKQSHDSRSQKRHRRRRNQTTEEQNYSEQRGNSKISQQSIKYKDHSHYHTN

KPGTYVSAINGIEKETHKSKTHNIYSNNTNHRAKDSTTDYHKESFKTSEVPSAIFGTMKPKKLENGRIPVS

KSSEKVESDKQKYDKYVAKTQTSQNKHLEQEKQKDSVVKQGTASKSSDENVSSTTKSTPNYSKVDNTIK

IENIYASQIVEEIRRERERKVLQKRRFKKALQQKREEHKNEEQDAIQRAIDEMYAKQAERYVGDSSLNDD

SDLTDNSTEASQLHTNEIEDEAVSNDENKKASIQNEDTDDTHVDESPYNYEEVSLNQVSTTKQLSDDEV

TVSDVTSQRQSALQHNVEVNNQDELKNQSRLIADSEEDGATNEEEYSGSQIDDAEFYELNDTEVDEDTT

SNSEDNTNRDASEMHVDAPKTQEHAVTESQVNNIDKTVDNEIELAPRHKKDDQTNLSVNSLKTNDVND

GHVVEDSSMNEIEKQNAEITENVQNEAAESKQNVEEKTIENVNPKKQTEKVSTLSKRPFNVVMTPSDKKR

MMDRKKHSKVNVPELKPVQSKQAASESKTATQNTPSSSTDSQESNTNAYKTNNMTSNNVENNQLIGHA

ATENDYQNAQQYSEQKPSADSTQTEIFEESQDDNQLENEQVDQSTSSSVSEVSDITEESEETTHQNNTS

GQQDNDDQQKDLQLSFSNQNEDTANENRPRTNQPDVATNQAVQTSKPMIRKGPNIKLPSVSLLEEPQVI

EPDEDWITDKKKELNDALFYFNVPAEVQDVTEGPSVTRFELSVEKGVKVSRITALQDDIKMALAAKDIRIE

APIPGTSRVGIEVPNQNPTTVNLRSIIESPSFKNAESKLTVAMGYRINNEPLLMDIAKTPHALIAGATGSGK

SVCINSILMSLLYKNHPEELRLLLIDPKMVELAPYNGLPHLVAPVITDVKAATQSLKWAVEEMERRYKLFAH

YHVRNITAFNKKAPYDERMPKIVIVIDELADLMMMAPQEVEQSIARIAQKARACGIHMLVATQRPSVNVIT

GLIKANIPTRIAFMVSSSVDSRTILDSGGAERLLGYGDMLYLGSGMNKPIRVQGTFVSDDEIDDVVDFIKQ

QREPDYLFEEKELLKKTQTQSQDELFDDVCAFMVNEGHISTSLIQRHFQIGYNRAARIIDQLEQLGYVSSA

NGSKPRDVYVTEADLNKE

SEQ ID NO: 11:
MSNQNYDYNKNEDGSKKKMSTTAKVVSIATVLLLLGGLVFAIFAYVDHSNKAKERMLNEQKQEQKEKRQ

KENAEKERKKKQQEEKEQNELDSQANQYQQLPQQNQYQYVPPQQQAPTKQRPAKEENDDKASKDESK

DKDDKASQDKSDDNQKKTDDNKQPAQPKPQPQQPTPKPNNNQQNNQSNQQAKPQAPQQNSQSTTNK

QNNANDK

SEQ ID NO: 12:
MKLKSLAVLSMSAVVLTACGNDTPKDETKSTESNTNQDTNTTKDVIALKDVKTSPEDAVKKAEETYKGQK

LKGISFENSNGEWAYKVTQQKSGEESEVLVDDKNKKVINKKTEKEDTVNENDNFKYSDAIDYKKAIKEG

QKEFDGDIKEWSLEKDDGKLVYNIDLKKGNKKQEVTVDAKNGKVLKSEQDQ

SEQ ID NO: 13:
MKKKNWIYALIVTLIIIIAIVSMIFFVQTKYGDQSEKGSQSVSNKNNKIHIAIVNEDQPTTYNGKKVELGQA

FIKRLANEKNYKFETVTRNVAESGLKNGGYQVMIVIPENFSKLAMQLDAKTPSKISLQYKTAVGQKEEVAK

NTEKVVSNVLNDFNKNLVEIYLTSIIDNLHNAQKNVGAIMTREHGVNSKFSNYLLNPINDFPELFTDTLVNS

ISANKDITKWFQTYNKSLLSANSDTFRVNTDYNVSTLIEKQNSLFDEHNTAMDKMLQDYKSQKDSVELD

NYINALKQMDSQIDQQSSMQDTGKEEYKQTVKENLDKLREIIQSQESPFSKGMIEDYRKQLTESLQDELA

NNKDLQDALNSIKMNNAQFAENLEKQLHDDIVKEPDSDTTFIYNMSKQDFIAAGLNEDEANKYEAIVKEA

KRYKNEYNLKKPLAEHINLTDYDNQVAQDTSSLINDGVKVQRTETIKSNDINQLTVATDPHFNFEGDIKIN

GKKYDIKDQSVQLDTSNKEYKVEVNGVAKLKKDAEKDFLKDKTMHLQLLFGQANRQDEPNDKKATSVV

DVTLNHNLDGRLSKDALSQQLSALSRFDAHYKMYTDTKGREDKPFDNKRLIDMMVDQVINDMESFKDD

KVAVLHQIDSMEENSDKLIDDILNNKKNTTKNKEDISKLIDQLENVKKTFAEEPQEPKIDKGKNDEFNTMS

SNLDKEISRISEKSTQLLSDTQESKTIADSVSGQLNQLDNNVNKLHATGRALGVRANDLNRQMAKNDKD

NELFAKEFKKVLQNSKDGDRQNQALKAFMSNPVQKKNLENVLANNGNTDVISPTLFVLLMYLLSMITAYIF

YSYERAKGQMNFIKDDYSSKNNLWNNAITSGVIGATGLVEGLIVGLIAMNKFHVLAGYRAKFILMVILTM

MVFVLINTYLLRQVKSIGMFLMIAALGLYFVAMNNLKAAGQGVTNKISPLSYIDNMFFNYLNAEHPIGLALV

ILTVLVIIGFVLNMFIKHFKKERLI

SEQ ID NO: 14:
MTQQQNNKRTLKNKHTYQNEPLPNRKDFVVSFITGALVGSALGLYFKNKVYQKADDLKVKEQELSQKFEE

RKTQLEETVAFTKERVEGFLNKSKNEQAALKAQQAAIKEEASANNLSDTSQEAQEIQEAKREAQTETDKS

AAVSNEESKASALKAQQAAIKEEASANNLSDTSQEAQAIQEVKKEAQAETDKSADVSNEESKASTLNVS

KEESQAERLANAAKQKQAKLTPGSKESQLTEALFAEKPVAKNDLKEIPLLVTKKNDVSETVNTDNKDTVK

QKEAKFENGVITRKADEKTPNNTAVDKKSGKQSKKTTPSNKRNASKASTNKTSGQKKQHNKKASQGAK

KQSSSSNSTTKTNQKNSKATNAKSSNASKKSNAKVEKAKSKIEKRTFND

SEQ ID NO: 15:
MDIGKKHVIPKSQYRRKRREFFHNEDREENLNQHQDKQNIDNTTSKKADKQIHKDSIDKHERFKNSLSS

HLEQRNRDVNENKAEESKSNQGSKSAYNKDHYLTDDVSKKQNSLDSVDQDTEKSKYYEQNTEATLSTN

STDKVESTDMRKLSSDKNKVGHEEQHVLSKPSEHDKETRIDFESSRTDSDSSMQTEKIKKDSSDGNKS

SNLKSEVISDKSNSVPILSESDDEVNNQKPLTLPEEQKLKRQQSQNEQTKTYTYGDSEQNDKSNHENDL

SHHTPSISDDKDYVMREDHIVDDNPDNDINTPSLSKIDDDRKLDEKIHVEDKHKQNADSSETVGYQSQS

SASHRSTEKRNMAINDHDKLNGQKPNTKTSANNNQKKATSKLNKGRAINNNYSAILKKFWMMYWPKLV

ILMGIIILIVILNAIFNNVNKNDRMNDNNDADAQKYTTTMKNANNAVKSVVTVENETSKDSSLPKDKASQ

DEVGSGVVYKKSGDTLYIVTNAHVVGDKENQKITFSNNKSVVGKVLGKDKWSDLAVVKATSSDSSVKEI

AIGDSNNLVLGEPILVVGNPLGVDFKGTVTEGIISGLNRNVPIDFDKDNKYDMLMKAFQIDASVNPGNSG

-continued

GAVVNREGKLIGVVAAKISMPNVENMSFAIPVNEVQKIVKELETKGKIDYPDVGVKMKNIASLNSFERQA

VKLLGKVKNGVVVDQVDNNGLADQSGLKKGDVITELDGKLLEDDLRFRQIIFSHKDDLKSITAKIYRDGK

EKEINIKLK

SEQ ID NO: 16:
MKFKAIVAITLSLSLLTACGANQHKENSSKSNDTNKKTQQTDNTTQSNTEKQMTPQEAEDIVRNDYKAR

GANENQTLNYKTNLERSNEHEYYVEHLVRDAVGTPLKRCAIVNRHNGTIINIFDDMSEKDKEEFEAFKKRS

PKYNPGMNDQAEMDNESEDIQHHDIDNNKAIQNDLPDQKVDDKNDKNAVNKEEKHDNRENNSAETKV

K

SEQ ID NO: 17:
MDKKKVIKFMINVLPIVLVPLIVERKRIKQHPDVQKVTDATSKVASKTSAAISNTASDVKEYVGDKKQDFE

NKRELKKFAREHDPAYIEKKGEKLAKQNRKDADKMNKILQKNIEKRHKEEQKAREKNEIQRIKDMKKSQK

YEVKAGLTPNKLDEKTEKKGDKLAEKNRKEIAKMNKKLQKNIEKRHKEEQKRQQEADKARIKSFKKYKDY

VAKSASQQNKENNTEA

SEQ ID NO: 18:
MSYHWFKKMLLSTSMLILSSSSSLGLATHTVEAKDNLNGEKPTTNLHNVTSPSVNSEMNNNETGTPHE

SNQAGNEGTGSNSRDANPDSNNVKPDSNNQNPSPDSKPDPNNPNPGPNPKPDPDKPKPNPEPKPDPDK

PKPNPDPKPDPDKPKPNPDPKPDPNPNPNPKPDPNKPNPNPSPNPNQPGDSNQSGGSKNGGTWNPNAS

DGSNQGQWQPNGNQGNSQNPTGNDFVSQRFLALANGAYKYNPYILNQINQLGKEYGEVTDEDIYNIIRK

QNFSGNAYLNGLQQQSNYFRFQYFNPLKSERYYRNLDEQVLALITGEIGSMPDLKKPEDKPDSKQRSFEP

HEKDDFTVVKKQEDNKKSASTAYSKSWLAIVCSMMVVFSIMLFLFVKRNKKKNKNESQRR

SEQ ID NO: 19:
MKKTLLASSLAVGLGIVAGNAGHEAQASEADLNKASLAQMAQSNDQTLNQKPIEAGAYNYTFDYEGFTY

HFESDGTHFAWNYHATGANGADMSAQAPATNNVAPSADQSNQVQSQEVEAPQNAQTQQPQASTSNN

SQVTATPTESKASEGSSVNVNDHLKQIAQRESGGNIHAVNPTSGAAGKYQFLQSTWDSVAPAKYKGVSP

ANAPESVQDAAAVKLYNTGGAGHWVTA

---

The invention claimed is:

1. A pharmaceutical composition consisting of at least one polypeptide and a pharmaceutically acceptable carrier, vehicle or diluent, and an immunological adjuvant, wherein the at least one polypeptide consists of 35-144 contiguous amino acid residues from amino acid residues 343-486 of SEQ ID NO: 9.

2. The pharmaceutical composition according to claim 1, wherein the at least one polypeptides consists of amino acid residues 343-452 of SEQ ID NO: 9.

3. A pharmaceutical composition consisting of
at least one polypeptide, and
a pharmaceutically acceptable carrier, vehicle or diluent, and an immunological adjuvant, wherein the at least one polypeptide consists of an amino acid sequence that has at least 80% sequence identity with 35-144 contiguous amino acids from amino acid residues 343-486 of SEQ ID NO: 9.

4. The pharmaceutical composition according to claim 1, wherein said at least one polypeptide is a single polypeptide.

5. The pharmaceutical composition according to claim 3, wherein said at least one polypeptide is a single polypeptide.

6. The pharmaceutical composition according to claim 3, wherein said at least one polypeptide consists of an amino acid sequence that has at least 80% sequence identity with 35-144 contiguous amino acids from amino acid residues 343-452 of SEQ ID NO: 9.

7. The pharmaceutical composition according to claim 1, wherein the immunological adjuvant is an aluminium based adjuvant.

8. The pharmaceutical composition according to claim 2, wherein the immunological adjuvant is an aluminium based adjuvant.

9. The pharmaceutical composition according to claim 3, wherein the immunological adjuvant is an aluminium based adjuvant.

* * * * *